(12) United States Patent
Brown

(10) Patent No.: US 11,214,798 B2
(45) Date of Patent: Jan. 4, 2022

(54) METHODS AND COMPOSITIONS FOR RAPID NUCLEIC ACID LIBRARY PREPARATION

(71) Applicant: iGenomX International Genomics Corporation, Carlsbad, CA (US)

(72) Inventor: Keith Brown, Carlsbad, CA (US)

(73) Assignee: iGenomX International Genomics Corporation, Carlsbad, CA (US)

( * ) Notice: Subject to any disclaimer, the term of this patent is extended or adjusted under 35 U.S.C. 154(b) by 0 days.

(21) Appl. No.: 16/563,233

(22) Filed: Sep. 6, 2019

(65) Prior Publication Data

US 2019/0390192 A1    Dec. 26, 2019

Related U.S. Application Data

(63) Continuation of application No. 15/509,747, filed as application No. PCT/US2015/049249 on Sep. 6, 2015, now Pat. No. 10,450,562.

(60) Provisional application No. 62/048,136, filed on Sep. 9, 2014, provisional application No. 62/048,138, filed on Sep. 9, 2014, provisional application No. 62/051,480, filed on Sep. 17, 2014, provisional application No. 62/104,431, filed on Jan. 16, 2015.

(51) Int. Cl.

| | |
|---|---|
| *C12N 15/10* | (2006.01) |
| *C12Q 1/6806* | (2018.01) |
| *C12Q 1/6874* | (2018.01) |
| *C12Q 1/6844* | (2018.01) |
| *C12Q 1/686* | (2018.01) |
| *C40B 40/06* | (2006.01) |
| *G16B 30/00* | (2019.01) |
| *G16B 30/20* | (2019.01) |

(52) U.S. Cl.
CPC ....... *C12N 15/1093* (2013.01); *C12Q 1/6806* (2013.01); *C12Q 1/6874* (2013.01); *G16B 30/00* (2019.02); *C12Q 1/686* (2013.01); *C12Q 1/6844* (2013.01); *C40B 40/06* (2013.01); *G16B 30/20* (2019.02)

(58) Field of Classification Search
None
See application file for complete search history.

(56) References Cited

U.S. PATENT DOCUMENTS

| | | |
|---|---|---|
| 4,318,846 A | 3/1982 | Khanna et al. |
| 4,437,975 A | 3/1984 | Gillespie et al. |
| 4,683,195 A | 7/1987 | Mullis et al. |
| 4,683,202 A | 7/1987 | Mullis |
| 4,757,141 A | 7/1988 | Fung et al. |
| 4,988,617 A | 1/1991 | Landegren et al. |
| 5,066,580 A | 11/1991 | Lee |
| 5,091,519 A | 2/1992 | Cruickshank |
| 5,151,507 A | 9/1992 | Hobbs, Jr. et al. |
| 5,188,934 A | 2/1993 | Menchen et al. |
| 5,242,794 A | 9/1993 | Whiteley et al. |
| 5,270,184 A | 12/1993 | Walker et al. |
| 5,366,860 A | 11/1994 | Bergot et al. |
| 5,399,491 A | 3/1995 | Kacian et al. |
| 5,405,746 A | 4/1995 | Uhlen |
| 5,409,818 A | 4/1995 | Davey et al. |
| 5,413,909 A | 5/1995 | Bassam et al. |
| 5,422,252 A | 6/1995 | Walker et al. |
| 5,494,810 A | 2/1996 | Barany et al. |
| 5,500,356 A | 3/1996 | Li et al. |
| 5,554,517 A | 9/1996 | Davey et al. |
| 5,648,245 A | 7/1997 | Fire et al. |
| 5,688,648 A | 11/1997 | Mathies et al. |
| 5,759,778 A | 6/1998 | Li et al. |
| 5,800,996 A | 9/1998 | Lee et al. |
| 5,847,162 A | 12/1998 | Lee et al. |
| 5,861,245 A | 1/1999 | McClelland et al. |
| 5,990,479 A | 11/1999 | Weiss et al. |
| 6,027,923 A | 2/2000 | Wallace |
| 6,063,603 A | 5/2000 | Davey et al. |
| 6,207,392 B1 | 3/2001 | Weiss et al. |
| 6,210,891 B1 | 4/2001 | Nyren et al. |
| 6,251,303 B1 | 6/2001 | Bawendi et al. |
| 6,309,824 B1 | 10/2001 | Drmanac |
| 6,319,426 B1 | 11/2001 | Bawendi et al. |
| 6,322,901 B1 | 11/2001 | Bawendi et al. |

(Continued)

FOREIGN PATENT DOCUMENTS

| | | |
|---|---|---|
| CN | 102439177 A | 5/2012 |
| WO | WO-8706270 A1 | 10/1987 |

(Continued)

OTHER PUBLICATIONS

Ciprianay, B. et al. Real-Time Analysis and Selection of Methylated DNA by Flourescence-Activated Single Molecule Sorting in a Nanofluidic Channel. Proceedings of the National Acadamy of Sciences. May 29, 2012 (published online before print May 14, 2012), vol. 109, No. 22, pp. 8477-8482.

(Continued)

*Primary Examiner* — Kaijiang Zhang

(74) *Attorney, Agent, or Firm* — Wilson Sonsini Goodrich & Rosati

(57) ABSTRACT

Rapid nucleic acid libraries, methods of generation, kits, and compositions relating to library synthesis, including reagents, intermediaries and final products are disclosed herein. The disclosure enables rapid synthesis of libraries that allow independent verification of sequence information and rapid identification of sequence information with template of origin.

20 Claims, 27 Drawing Sheets

Specification includes a Sequence Listing.

(56) References Cited

U.S. PATENT DOCUMENTS

| | | |
|---|---|---|
| 6,401,267 B1 | 6/2002 | Drmanac |
| 6,410,276 B1 | 6/2002 | Burg et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,576,291 B2 | 6/2003 | Bawendi et al. |
| 6,582,938 B1 | 6/2003 | Su et al. |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,911,345 B2 | 6/2005 | Quake et al. |
| 7,232,656 B2 | 6/2007 | Balasubramanian et al. |
| 7,459,311 B2 | 12/2008 | Nyren et al. |
| 7,648,824 B2 | 1/2010 | Nyren et al. |
| 7,670,810 B2 | 3/2010 | Gunderson et al. |
| 8,114,978 B2 | 2/2012 | Jones et al. |
| 8,168,385 B2 | 5/2012 | Brenner |
| 9,968,901 B2 | 5/2018 | Head |
| 2002/0045045 A1 | 4/2002 | Adams et al. |
| 2003/0017264 A1 | 1/2003 | Treadway et al. |
| 2003/0143599 A1 | 7/2003 | Makarov et al. |
| 2005/0191656 A1 | 9/2005 | Drmanac et al. |
| 2006/0252060 A1 | 11/2006 | Willis et al. |
| 2007/0207482 A1 | 9/2007 | Church et al. |
| 2007/0264642 A1 | 11/2007 | Willis et al. |
| 2009/0018024 A1 | 1/2009 | Church et al. |
| 2009/0036325 A1 | 2/2009 | McKernan et al. |
| 2009/0118128 A1* | 5/2009 | Liu et al. ............. C12Q 1/6874 506/2 |
| 2010/0105052 A1 | 4/2010 | Drmanac et al. |
| 2010/0222238 A1 | 9/2010 | Smith et al. |
| 2010/0273219 A1 | 10/2010 | May et al. |
| 2010/0311064 A1* | 12/2010 | Oliphant et al. ...... C12Q 1/6834 435/6.11 |

FOREIGN PATENT DOCUMENTS

| | | |
|---|---|---|
| WO | WO-9006995 A1 | 6/1990 |
| WO | WO-2006137733 A1 | 12/2006 |
| WO | WO-2007073171 A2 | 6/2007 |
| WO | WO-2011142836 A9 | 1/2012 |
| WO | WO-2013010062 A2 | 1/2013 |
| WO | WO-2016040524 A1 | 3/2016 |

OTHER PUBLICATIONS

Drmanac et al. Human genome sequencing using unchained base reads on self-assembling DNA nanoarrays. Science. 327: 78-81 (2010).

European Application No. 13793337.0 Partial Supplementary European Search Report dated Apr. 11, 2016.

Grillo et al.,CLEANUP: a fast computer program for removing redundancies from nucleotide sequence databases. Bioinformatics. 12(1): 1—(1996).

Guatelli et al. Isothermal, in vitro amplification of nucleic acids by a multienzyme reaction modeled after retroviral replication. PNAS USA 87(5):1874-1878 (1990).

Hamady, M. et al. Error-Correcting Barcoded Primer for Pyrosequencing Hundreds of Samples in Multiplex. Nat. Methods. 5(3): 235-237 (2008).

PCT/US2015/049249 International Search Report and Written Opinion dated Feb. 3, 2016.

Emmersen et al., Discarding duplicate ditags in LongSAGE analysis may introduce significant error. BMC Bioinformatics. 8:92 (2007). 12 pages.

Kienzler, R. et al. Large-Scale DNA Sequence Analysis in the Cloud: A Stream-Based Approach. Euro-Par 20122: Parallel Processing Workshops Lecture Notes in Computer Science. 7156: 467-476 (2012).

Kim S., et al. Solid phase capturable dideoxynucleotides for multiplex genotyping using mass spectrometry. Nucleic Acids Research 30(16); e85 (2002).

Landegren et al., A ligase-mediated gene detection technique. Science 241(4869): 1077-1080 (1988).

Li et al., A photocleavable fluorescent nucleotide for DNA sequencing and analysis. Proc. Natl. Acad. Sci., 100: 414-419 (2003).

Makrigiorgos, et al., A PCR-Based amplification method retaining quantitative difference between two complex genomes. Nature Biotech 20(9): 936-939 (2002).

Meyer, M. et al. Targeted High-Throughput Sequencing of Tagged Nucleic Acid Samples. Nucleic Acids Research. 35(15): e97 (2007). 5 pages.

Nunez et al. Application of Circular Ligase to Provide Template for Rolling Circle Amplification of Low Amounts of Fragmented DNA. FBI Publication (2008).

Orsouw, Nathalie J. et al. Complexity Reduction of Polymorphic Sequences (CRoPS): A Novel Approach for Large-Scale Polymorphism Discovery in Complex Genomes. PLoS One, 2(11): e1172 (2007). 10 pages.

PCT/US2013/042106 International Preliminary Report on Patentability dated Nov. 25, 2014.

PCT/US2013/042106 International Search Report and Written Opinion dated Oct. 17, 2013.

Qiu, Chunmei et al. Design and synthesis of cleavable biotinylated dideoxynucleotides for DNA sequencing by matrix-assisted laser desorption/ionization time-of-flight mass spectrometry. Analytical Biochemistry. 427(2): 193-201 (2012).

Supplementary European search report and opinion dated Sep. 5, 2016 for EP Application No. 13793337.

Tong, AK., et al. Single nucleotide polymorphism detection by combinatorial fluorescence energy transfer tags and biotinylated dideoxynucleotides. Nucleic Acids Research 30(5): e19 (2002).

U.S. Appl. No. 15/509,747 Office Action dated Jan. 10, 2019.

Van Dijk, Erwin L., et al. Library preparation methods for next-generation sequencing: tone down the bias. Experimental Cell Research, 322(1): 12-20 (2014).

Wachter A., et al. A 50 SNP-multiplex mass spectrometry assay for human identification. Forensic Science International: Genetics Supplemental Series, 1(1): 487-489 (2008).

Walker et al., SEALS: a system for easy analysis of lots of sequences. International Conference on Intelligent Systems for Molecular. XP055295893 (1997). 8 pages.

Walker et al., Strand displacement amplification—an isothermal, in vitro DNA amplification technique. Nucleic Acids Res. 20(7):1691-6 (1992).

Wetmur, James G., DNA Probes: Applications of the Principles of Nucleic Acid Hybridization. Critical Reviews in Biochemistry and Molecular Biology 26(3/4): 227-259 (1991).

Wilhelm, B. et al. RNA-Seq-quantitative measurement of expression through massively parallel RNA-sequencing. Methods 48(3): 249-257 (2009).

Wu & Wallace, The ligation amplification reaction (LAR)—Amplification of specific DNA sequences using sequential rounds of template-dependent ligation. (Ligase Chain Reaction (LR)) Genomics 4(4): 560-569 (1989).

* cited by examiner

RLP

R_RLP

L_RLP

T_RLP

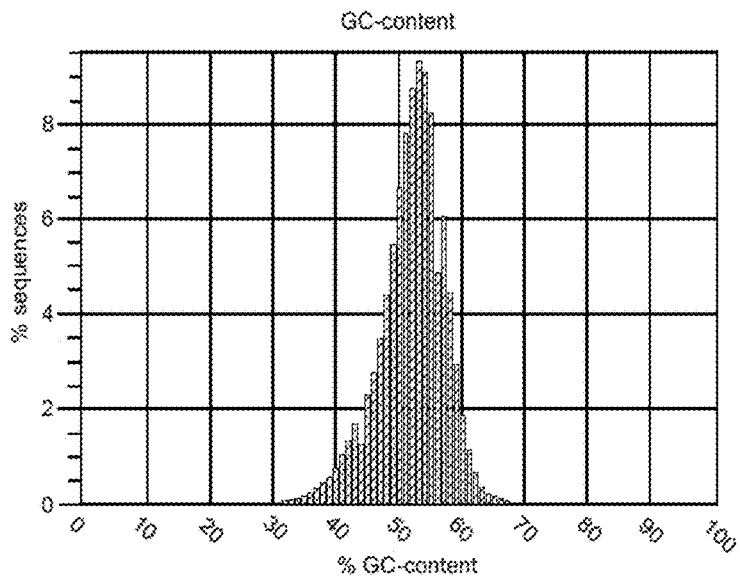

Distribution of GC-contents. The GC-content of a sequence is calculated as the number of GC-cases compared to all bases (including ambiguous bases).
x: relative GC-content of a sequence in percent
y: number of sequences featuring particular GC-percentage normalized to the total number of sequences

FIG. 7A

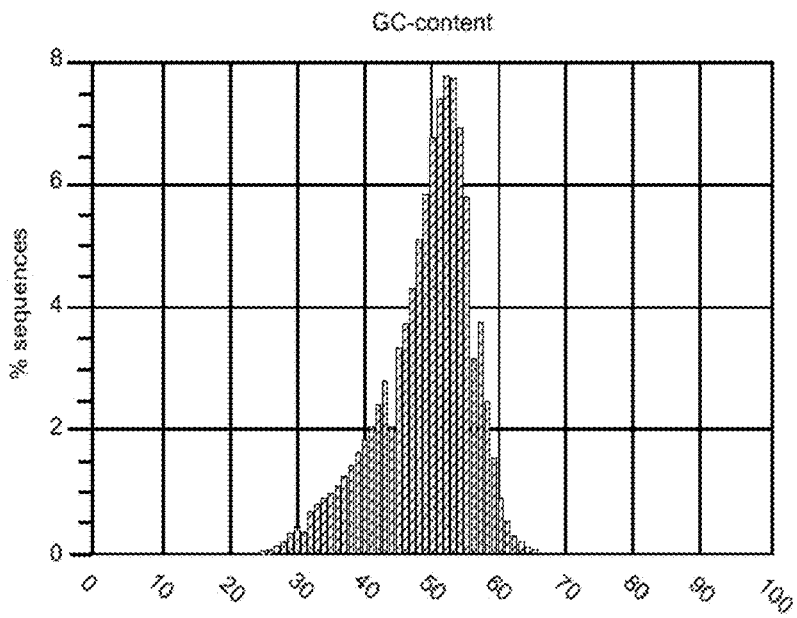

Distribution of GC-contents. The GC-content of a sequence is calculated as the number of GC-cases compared to all bases (including ambiguous bases).
x: relative GC-content of a sequence in percent
y: number of sequences featuring particular GC-percentage normalized to the total number of sequences

FIG. 7B 50 ng input DNA
6 PCR cycles 50 ng input DNA
9 PCR cycles 50 ng input DNA
12 PCR cycles 50 ng input DNA
15 PCR cycles

| AIP | CYLD | FANCI | NF1 | SDHAF2 |
|---|---|---|---|---|
| ALK | DDB2 | FANCL | NF2 | SDHB |
| APC | DICER1 | FANCM | NSD1 | SDHC |
| ATM | DIS3L2 | FH | PALB2 | SDHD |
| AXIN1 | EGFR | FLCN | PHOX2B | SLX4 |
| BAP1 | EPCAM | GATA2 | PMS1 | SMAD4 |
| BLM | ERCC2 | GPC3 | PMS2 | SMARCB1 |
| BMPR1A | ERCC3 | HNF1A | PRF1 | SMARCE1 |
| BRCA1 | ERCC4 | HRAS | PRKAR1A | STK11 |
| BRCA2 | ERCC5 | KCNJ5 | PTCH1 | SUFU |
| BRIP1 | EXT1 | KIT | PTEN | TERT |
| BUB1B | EXT2 | MAX | RAD51C | TMEM127 |
| CDC73 | EZH2 | MEN1 | RAD51D | TP53 |
| CDH1 | FANCA | MET | RB1 | TSC1 |
| CDK4 | FANCB | MLH1 | RECQL4 | TSC2 |
| CDKN1C | FANCC | MPL | RET | TSHR |
| CDKN2A | FANCD2 | MSH2 | RHBDF2 | VHL |
| CEBPA | FANCE | MSH6 | SDH5 (RP11-286N22.8) | WRN |
| CEP57 | FANCF | MUTYH | RUNX1 | WT1 |
| CHEK2 | FANCG | NBN | SBDS | XPA |
| | | | | XHNF1A |

FIG. 19

METHODS AND COMPOSITIONS FOR RAPID NUCLEIC ACID LIBRARY PREPARATION

This application is a continuation of U.S. application Ser. No. 15/509,747, filed Mar. 8, 2017, now U.S. Pat. No. 10,450,562, issued Oct. 22, 2019, which is a National Stage Entry of PCT/US2015/049249, filed Sep. 9, 2015, which claims the benefit to U.S. Provisional Application No. 62/048,136, filed on Sep. 9, 2014, U.S. Provisional Application No. 62/048,138, filed on Sep. 9, 2014, U.S. Provisional Application No. 62/051,480, filed Sep. 17, 2014, and U.S. Provisional Application No. 62/104,431, filed Jan. 16, 2015, the content each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 6, 2019, is named 44013-708.301_SL.txt and is 1,037 bytes in size. No new matter is introduced through incorporation of the sequence listing.

BACKGROUND OF THE INVENTION

Background

A critical component in making use of sequence information is isolating and amplifying genes that cause disease. However, these disease-causing genes is "complex" and include large insertions/deletions, translocations, or other length-altering chromosomal changes that cannot be detected by PCR or captured without prior knowledge (e.g., a reference genome). Several biological applications involve nucleic acid sequencing, including next-generation sequencing. Next-generation sequencing can amplify clonal errors, leading to the inability to distinguish between natural abundance of a molecule and abundance resulting from differential clonal amplification.

SUMMARY OF THE INVENTION

Processes and compositions for adding synthetic codes to existing sample-derived sequence without changing the function of the code are disclosed. This "Molecular Refactoring" functions similar to code refactoring in software and, via the synthetic codes, makes a sample-derived code more easily analyzed.

Through the methods and compositions herein, a nucleic acid sample is used to generate a sequencing library comprising tagged, overlapping, fragment molecules each of which is unique in the library. As a result, the libraries generated hereby are not vulnerable to the error propagation that results from generating unfiltered libraries from exponential amplification of sample fragments and library intermediates. Each library constituent is uniquely identifiable by its insert length, random 5' tag and random 3' tag. Duplicates having identical tags at each end, and identical insert sequence as judged by start point, end point and content, are readily identified and removed, so as to eliminate the risk of amplification bias influencing library analysis. Mutations in library generation are easily identified as rare and unique to single library constituents, while mutations that distinguish various alleles in a diploid sample are easily identified by the fact that they show up repeatedly in independently generated and independently tagged library constituents. The result is a library that allows easy recognition and elimination of artefactual errors in library generation, facilitating substantially more accurate nucleic acid sequencing.

A beneficial element of some methods and compositions herein is the use of dideoxynucleotides in library first strand chain termination. Dideoxynucleotides do not support DNA polymerase-driven chain extension. As a result, library intermediates incorporating a dideoxy nucleotide at their 3' end are unable to serve as primers for further chain extension in subsequent rounds of library generation. This beneficial trait prevents the generation of chimeric library constituents through the annealing of a library intermediate to a random or repeated region of a genome and polymerase-directed extension from that region resulting in a chimeric library constituent. As a result, the methods disclosed herein are far more able than many techniques in the art at accurately generating libraries from nucleic acid samples having repeat regions, such as those known to be so common in the human genome.

Thus, sequencing libraries generated hereby, and the sequence generated therefrom, are better than some comparable libraries in at least two aspects. First, through the use of triple-tagging of library components, duplicate library molecules that share all three tags are easily identified and discarded, and thus mutations introduced in the library generation process that led to the duplicates are easily distinguished from mutations that reflect the underlying sample. This is because mutations that reflect the underlying sample will occur multiple times independently in the generated library, while artefacts are more likely to be unique to a given library molecule and its duplicates. If one is unable to identify duplicates, then artefactual mutations, due to amplification bias, may become abundant enough to confuse downstream analysis.

Second, though the use of dideoxynucleotides in library generation, there is a much reduced chance of generating chimeric library molecule that could be confused with translocation or insertion events in library sequence analysis. Chimeric library molecule generation is a major obstacle for sequence analysis or contig assembly, particularly when analyzing a heterogeneous sample that may comprise rare translocation or transposition events such as a cancer DNA sample. By minimizing the possibility of artefactual chimera formation, libraries generated hereby are easier to sequence and assemble.

Another benefit of some library generation methods herein is the ease with which they are executed. In particular, multiple steps are performed in a single tube, or in a sing well or in a single chamber, without size fractionation or column or gel purification, such that libraries are generated with a minimum of time or processing.

Some embodiments relate to methods of generating a population of non-identical, tagged nucleic acid molecules each comprising a subset of sequence from a target nucleic acid sample. Some aspects of these embodiments relate to methods of generating a population of non-identical, tagged nucleic acid molecules each comprising a subset of sequence from a target nucleic acid sample, the methods comprising obtaining a first nucleic acid molecule comprising a first molecular tag sequence and a first target sequence having a first length from said target nucleic acid sample; annealing an oligonucleotide comprising a second molecular tag sequence to said first nucleic acid molecule; extending said oligonucleotide to obtain a first double-stranded nucleic acid molecule comprising a first molecular tag sequence, a first target sequence having a first length, and a second molecular tag sequence; obtaining a second double-stranded nucleic acid molecule comprising a third molecular tag sequence, a second target sequence having a second length, and a fourth molecular tag sequence; and discarding said second double-stranded nucleic acid molecule if said third molecular tag sequence is identical to said first molecular tag sequence; said fourth molecular tag sequence is identical to said second molecular tag sequence; said second target sequence is identical to said first target sequence; and said second target sequence length is identical to said first target sequence length. Some aspects of these embodiments relate to methods of generating a population of non-identical, tagged nucleic acid molecules each comprising a subset of sequence from a target nucleic acid sample, the methods comprising obtaining a first nucleic acid molecule comprising a first molecular tag sequence and a first target sequence having a first length from said target nucleic acid sample; annealing an oligonucleotide comprising a second molecular tag sequence to said first nucleic acid molecule; extending said oligonucleotide to obtain a first double-stranded nucleic acid molecule comprising a first molecular tag sequence, a first target sequence having a first length, and a second molecular tag sequence; obtaining a second double-stranded nucleic acid molecule comprising a third molecular tag sequence, a second target sequence having a second length, and a fourth molecular tag sequence; discarding said second double-stranded nucleic acid molecule if said third molecular tag sequence is identical to said first molecular tag sequence; said fourth molecular tag sequence is identical to said second molecular tag sequence; said second target sequence is identical to said first target sequence; and said second target sequence length is identical to said first target sequence length; and retaining said second double-stranded nucleic acid molecule if said third molecular tag sequence is different from said first molecular tag sequence; said fourth molecular tag sequence is different from said second molecular tag sequence; said second target sequence is different from said first target sequence; or said second target sequence length is different from said first target sequence length, thereby generating a population of non-identical, tagged nucleic acid molecules each comprising a subset of sequence from a target nucleic acid sample. In some aspects, said first nucleic acid molecule is obtained through contacting a first primer comprising a first random oligonucleotide sequence to a target nucleic acid sample. In some aspects, said contacting a first primer comprises annealing said first primer to a nucleic acid of said target nucleic acid sample. In some aspects, said first nucleic acid molecule comprises a molecular ligand. In some aspects, said molecular ligand comprises biotin. In some aspects, said second nucleic acid molecule is generated through contacting a second primer comprising a second random oligonucleotide sequence to said first nucleic acid molecule. In some aspects, said first random oligonucleotide sequence of said first nucleic acid molecule consists of a number of nucleic acid bases selected from the list consisting of 6, 7, 8, 9, and 10 nucleotide bases. In some aspects, said first nucleic acid molecule comprises an adapter sequence positioned 5' to said first random oligonucleotide sequence. In some aspects, said methods comprise contacting said first nucleic acid and said first primer to a nucleic acid polymerase and a nucleotide triphosphate. In some aspects, said nucleotide triphosphate is selected by said nucleic acid polymerase from a pool comprising deoxynucleotide triphosphates and dideoxynucleotide triphosphates. In some aspects, said pool comprises dideoxynucleotide triphosphates in an amount ranging from 0.01% to 5%. In some aspects, said pool comprises dideoxynucleotide triphosphates in an amount ranging from 0.05% and 1.0%. In some aspects, said nucleotide is added by a nucleic acid polymerase enzyme having strand displacement activity. In some aspects, said pool comprises at least one of said dideoxynucleotide triphosphates bound to a molecular ligand. In some aspects, said molecular ligand comprises biotin. In some aspects, said methods comprise contacting a molecule comprising said oligonucleotide comprising a second molecular tag sequence annealed to said first nucleic acid molecule to a ligand binding agent. In some aspects, said ligand binding agent is avidin. In some aspects, said ligand binding agent is streptavidin. In some aspects, each of said first random oligonucleotide sequence and said second random oligonucleotide sequence is selected to reflect the GC content of the first target sequence. In some aspects, at least one of said nucleic acids is a deoxyribonucleic acid. In some aspects, at least one of said nucleic acids is a ribonucleic acid. In some aspects, said target nucleic acid sample is ribonucleic acid. In some aspects, said first nucleic acid molecule is a complementary deoxyribonucleic acid molecule generated from said ribonucleic acid. In some aspects, said nucleic acid polymerase is an RNA-dependent DNA polymerase. In some aspects, said nucleotide is added by a nucleic acid polymerase enzyme lacking strand displacement activity. In some aspects, said first nucleic acid molecule is a complementary deoxyribonucleic acid molecule generated through contacting a first primer comprising an oligo(dT) sequence to said target nucleic acid sample. In some aspects, said deoxyribonucleic acid is fragmented into fragments greater than 10 kilobases. In some aspects, said methods comprise assigning all sequences from a given contig having the same molecular tag to a specific homologous chromosome. In some aspects, said second nucleic acid molecule is generated through contacting a second primer comprising a locus-specific oligonucleotide sequence and a second molecular tag sequence to said first nucleic acid molecule.

Some embodiments relate to compositions. Some aspects of these embodiments relate to compositions comprising: a first nucleic acid molecule comprising a first molecular tag sequence and a first target sequence having a first length; and an oligonucleotide comprising a second molecular tag sequence. In some aspects, said first nucleic acid molecule comprises a 3' deoxynucleotide. In some aspects, said 3' deoxynucleotide is a dideoxynucleotide. In some aspects, said first nucleic acid molecule comprises an adapter sequence positioned 5' to said first molecular tag sequence. In some aspects, said first adapter comprises SEQ ID NO: 1. In some aspects, said first nucleic acid molecule comprises a molecular ligand. In some aspects, said molecular ligand comprises biotin. In some aspects, said composition comprises a ligand binding agent. In some aspects, said ligand binding agent comprises avidin. In some aspects, said ligand binding agent comprises streptavidin. In some aspects, said compositions comprise unincorporated nucleotides. In some aspects, said compositions comprise unincorporated deoxynucleotides. In some aspects, said compositions comprise unincorporated dideoxynucleotides. In some aspects, said first nucleic acid molecule is hybridized to said oligonucleotide comprising a second molecular tag sequence. In some aspects, said first nucleic acid molecule is completely hybridized to said second molecular tag sequence of said oligonucleotide. In some aspects, said first nucleic acid molecule is incompletely hybridized to said second molecular tag sequence of said oligonucleotide. In some aspects, said compositions comprise a ligand-ligand binding agent wash buffer. In some aspects, said compositions comprise a biotin wash buffer.

Some embodiments relate to compositions comprising a population of nucleic acid molecules. Some aspects of these embodiments relate to compositions comprising a population of nucleic acid molecules, wherein each molecule of said population independently comprises: a first strand comprising a first adapter sequence, a molecular tag sequence, and an independent target sequence, wherein said each independent target sequence comprises a subset of a sample nucleic acid sequence, and wherein at least a first molecule of said population comprises an independent target sequence comprising a first subset of said sample nucleic acid sequence, and wherein at least a second molecule of said population comprises an independent target sequence that comprises a second subset of said sample nucleic acid sequence. In some aspects, said adapter of each first strand of said population is identical. In some aspects, said molecular tag sequence of each molecule of said population comprises at least 6 nucleotide bases. In some aspects, a first member of said population and a second member of said population comprise non-identical molecular tag sequences. In some aspects, each first strand comprises a 3'-deoxynucleotide base at its 3' end. In some aspects, each first strand comprises a molecular ligand at its 5' end. In some aspects, each first strand comprises a molecular ligand attached at a non-terminal position. In some aspects, each first strand comprises a molecular ligand at its 3' end. In some aspects, said molecular ligand is biotin. In some aspects, each molecule of said population comprises a second strand comprising: a second adapter sequence, and a second molecular tag sequence. In some aspects, said second strand of at least one molecule of said population is annealed to a first strand via at least partial base pairing of a second molecular tag sequence of said second strand to the independent target sequence of said first strand. In some aspects, said adapter of each second strand of said population is identical. In some aspects, at least one molecule of said population is bound to a molecular ligand binder. In some aspects, said molecular ligand binder comprises avidin. In some aspects, said molecular ligand binder comprises streptavidin. In some aspects, said composition comprises unincorporated nucleic acid triphosphates. In some aspects, said composition comprises molecular ligand binder wash buffer. In some aspects, said composition comprises polymerase extension buffer. In some aspects, said composition comprises nucleic acid polymerase. In some aspects, said composition comprises nucleic acid polymerase possessing nucleic acid helicase activity. In some aspects, said composition comprises nucleic acid polymerase possessing nucleic acid strand displacement activity. In some aspects, said composition comprises nucleic acid comprising SEQ ID NO: 1 and SEQ ID NO: 2.

Some embodiments relate to oligonucleotide libraries. Some aspects of these embodiments relate to oligonucleotide libraries comprising a plurality of oligonucleotide molecules, wherein each oligonucleotide molecule comprises a donor primer binding site positioned 5' to a random oligonucleotide sequence, and wherein said random oligonucleotide sequence is positioned 3' to all other sequence of said oligonucleotide molecule. In some aspects, said random oligonucleotide sequence consists of 6 nucleotide bases. In some aspects, said random oligonucleotide sequence consists of 7 nucleotide bases. In some aspects, said random oligonucleotide sequence consists of 8 nucleotide bases. In some aspects, said random oligonucleotide sequence consists of 9 nucleotide bases. In some aspects, said random oligonucleotide sequence consists of 10 nucleotide bases. In some aspects, said donor primer binding site and said random oligonucleotide sequence are separated by an oligonucleotide sequence comprising a molecular label. In some aspects, said plurality of oligonucleotide molecules comprises a first oligonucleotide molecule having a first random oligonucleotide sequence and second oligonucleotide molecule having a second random oligonucleotide sequence. In some aspects, for each random oligonucleotide sequence comprising at least one category of bases selected from the list of the nucleic acid bases A, T, G and C, said plurality of oligonucleotide molecules comprises at least one oligonucleotide molecule having a said random 8-mer. In some aspects, all random sequences are represented by at least one oligonucleotide molecule. In some aspects, said library comprises oligonucleotides. In some aspects, each oligonucleotide molecule comprises a molecular label sequence. In some aspects, said molecular label sequence is positioned between said donor primer binding site and said random oligonucleotide sequence.

Some embodiments relate to polynucleotide molecules. Some aspects of these embodiments relate to polynucleotide molecules comprising a donor primer binding site, a random oligonucleotide sequence, and a polynucleotide sequence that is reverse-complementary to a template sequence. In some aspects, said template sequence is a sequencing target sequence. In some aspects, said template sequence is a human sample sequence. In some aspects, said polynucleotide molecule is not hybridized to said template sequence. In some aspects, said random oligonucleotide sequence consists of 6 nucleotide bases. In some aspects, said random oligonucleotide sequence consists of 7 nucleotide bases. In some aspects, said random oligonucleotide sequence consists of 8 nucleotide bases. In some aspects, said random oligonucleotide sequence consists of 9 nucleotide bases. In some aspects, said random oligonucleotide sequence consists of 10 nucleotide bases. In some aspects, said polynucleotide sequence that is reverse-complementary to a template sequence comprises a 3' di-deoxy nucleotide ribose moiety at its terminal 3' position. In some aspects, said terminal 3' position comprises a biotin tag. In some aspects, said polynucleotide sequence that is reverse-complementary to a template sequence comprises a biotin tag. In some aspects, said biotin tag is positioned at the 3' end of said molecule. In some aspects, said molecule is bound to streptavidin. In some aspects, said polynucleotide sequence that is reverse-complementary to a template sequence comprises at least 500 bases. In some aspects, said polynucleotide sequence that is reverse-complementary to a template sequence comprises at least 100 bases. In some aspects, said polynucleotide is suspended in biotin-streptavidin elution buffer.

Some embodiments relate to nucleic acid molecules. Some aspects of these embodiments relate to nucleic acid molecules comprising, from 5' to 3', a first sequencer-specific adapter sequence, a random oligonucleotide sequence, a target sequence, a first molecular barcode sequence, and a second sequencer-specific adapter sequence. In some aspects, said molecules comprise a second molecular barcode sequence. In some aspects, said random oligonucleotide sequence consists of 6 nucleotide bases. In some aspects, said random oligonucleotide sequence consists of 7 nucleotide bases. In some aspects, said random oligonucleotide sequence consists of 8 nucleotide bases. In some aspects, said random oligonucleotide sequence consists of 9 nucleotide bases. In some aspects, said random oligonucleotide sequence consists of 10 nucleotide bases. In some aspects, said first sequencer-specific adapter sequence and said second sequencer-specific adapter sequence are compatible with pyrosequencing. In some aspects, said first sequencer-specific adapter sequence and said second sequencer-specific adapter sequence are compatible with sequencing by ligation. In some aspects, said first sequencer-specific adapter sequence and said second sequencer-specific adapter sequence are compatible with synthesis using modified nucleotides. In some aspects, said first sequencer-specific adapter sequence and said second sequencer-specific adapter sequence are compatible with sequencing by ion detection technology. In some aspects, said first sequencer-specific adapter sequence and said second sequencer-specific adapter sequence are compatible with sequencing by DNA nanoball technology. In some aspects, said first sequencer-specific adapter sequence and said second sequencer-specific adapter sequence are compatible with nanopore-based sequencing technology.

Some embodiments relate to methods of identifying clonally amplified nucleic acid sequences. Some aspects of these embodiments relate to methods of identifying clonally amplified nucleic acid sequences, comprising the steps of obtaining a first nucleic acid sequence comprising a first molecular tag sequence and a first target sequence having a first length; obtaining a second nucleic acid sequence comprising a second molecular tag sequence and a second target sequence having a second length; and discarding said second nucleic acid sequence if said second nucleic acid sequence comprises a second molecular tag sequence that is identical to said first molecular tag sequence, said second target sequence is identical to said first target sequence, and said second target sequence length is identical to said first target sequence length. In some aspects, said second nucleic acid sequence comprises a second molecular tag sequence that is identical to said first molecular tag sequence, said second target sequence is identical to said first target sequence, and said second target sequence length is identical to said first target sequence length, then said second nucleic acid sequence and said first nucleic acid sequence are related by clonal amplification. In some aspects, said first nucleic acid sequence is generated through the annealing of a first primer comprising a first random oligonucleotide sequence. In some aspects, said second nucleic acid sequence is generated through the annealing of a second primer comprising a second random oligonucleotide sequence. In some aspects, each of said first random oligonucleotide sequence and said second random oligonucleotide sequence consist of 6 nucleotide bases. In some aspects, each of said first random oligonucleotide sequence and said second random oligonucleotide sequence consist of 7 nucleotide bases. In some aspects, each of said first random oligonucleotide sequence and said second random oligonucleotide sequence consist of 8 nucleotide bases. In some aspects, each of said first random oligonucleotide sequence and said second random oligonucleotide sequence consist of 9 nucleotide bases. In some aspects, each of said first random oligonucleotide sequence and said second random oligonucleotide sequence consist of 10 nucleotide bases. In some aspects, said first target sequence is generated through a process that results in a sequence of variable length. In some aspects, said first target sequence is generated through addition of at least one nucleotide to said first random oligonucleotide sequence. In some aspects, said nucleotide is selected from a pool comprising deoxynucleotide triphosphates and di-deoxynucleotide triphosphates. In some aspects, said nucleotide is added by a DNA polymerase enzyme that lacks strand displacement activity.

Some embodiments relate to oligonucleotide libraries. Some aspects of these embodiments relate to oligonucleotide libraries comprising a plurality of oligonucleotide molecules, wherein each oligonucleotide molecule comprises a donor primer binding site positioned 5' to a random oligonucleotide sequence, and wherein said random oligonucleotide sequence is positioned 3' to all other sequence of said oligonucleotide molecule. In some aspects, said random oligonucleotide sequence consists of 6 nucleotide bases. In some aspects, said random oligonucleotide sequence consists of 7 nucleotide bases. In some aspects, said random oligonucleotide sequence consists of 8 nucleotide bases. In some aspects, said random oligonucleotide sequence consists of 9 nucleotide bases. In some aspects, said random oligonucleotide sequence consists of 10 nucleotide bases. In some aspects, said donor primer binding site and said random oligonucleotide sequence are separated by an oligonucleotide sequence comprising a molecular label. In some aspects, said plurality of oligonucleotide molecules comprises a first oligonucleotide molecule having a first random oligonucleotide sequence and second oligonucleotide molecule having a second random oligonucleotide sequence. In some aspects, for each random oligonucleotide sequence comprising at least one category of bases selected from the list of the nucleic acid bases A, T, G and C, said plurality of oligonucleotide molecules comprises at least one oligonucleotide molecule having a said random 8-mer. In some aspects, all random sequences are represented by at least one oligonucleotide molecule. In some aspects, said library comprises oligonucleotides. In some aspects, each oligonucleotide molecule comprises a molecular label sequence. In some aspects, said molecular label sequence is positioned between said donor primer binding site and said random oligonucleotide sequence.

Some embodiments relate to polynucleotide molecules. Some aspects of these embodiments relate to polynucleotide molecules comprising a donor primer binding site, a random oligonucleotide sequence, and a polynucleotide sequence that is reverse-complementary to a template sequence. In some aspects, said template sequence is a sequencing target sequence. In some aspects, said template sequence is a human sample sequence. In some aspects, said polynucleotide molecule is not hybridized to said template sequence. In some aspects, said random oligonucleotide sequence consists of 6 nucleotide bases. In some aspects, said random oligonucleotide sequence consists of 7 nucleotide bases. In some aspects, said random oligonucleotide sequence consists of 8 nucleotide bases. In some aspects, said random oligonucleotide sequence consists of 9 nucleotide bases. In some aspects, said random oligonucleotide sequence consists of 10 nucleotide bases. In some aspects, said polynucleotide sequence that is reverse-complementary to a template sequence comprises a 3' di-deoxy nucleotide ribose moiety at its terminal 3' position. In some aspects, said terminal 3' position comprises a biotin tag. In some aspects, said polynucleotide sequence that is reverse-complementary to a template sequence comprises a biotin tag. In some aspects, said biotin tag is positioned at the 3' end of said molecule. In some aspects, said molecule is bound to streptavidin. In some aspects, said polynucleotide sequence that is reverse-complementary to a template sequence comprises at least 500 bases. In some aspects, said polynucleotide sequence that is reverse-complementary to a template sequence comprises at least 100 bases. In some aspects, said polynucleotide is suspended in biotin-streptavidin elution buffer.

Some embodiments relate to nucleic acid molecules. Some aspects of these embodiments relate to nucleic acid molecules comprising, from 5' to 3', a first sequencer-specific adapter sequence, a random oligonucleotide sequence, a target sequence, a first molecular barcode sequence, and a second sequencer-specific adapter sequence. In some aspects, said molecules comprise a second molecular barcode sequence. In some aspects, said random oligonucleotide sequence consists of 6 nucleotide bases. In some aspects, said random oligonucleotide sequence consists of 7 nucleotide bases. In some aspects, said random oligonucleotide sequence consists of 8 nucleotide bases. In some aspects, said random oligonucleotide sequence consists of 9 nucleotide bases. In some aspects, said random oligonucleotide sequence consists of 10 nucleotide bases. In some aspects, said first sequencer-specific adapter sequence and said second sequencer-specific adapter sequence are compatible with pyrosequencing. In some aspects, said first sequencer-specific adapter sequence and said second sequencer-specific adapter sequence are compatible with sequencing by ligation. In some aspects, said first sequencer-specific adapter sequence and said second sequencer-specific adapter sequence are compatible with synthesis using modified nucleotides. In some aspects, said first sequencer-specific adapter sequence and said second sequencer-specific adapter sequence are compatible with sequencing by ion detection technology. In some aspects, said first sequencer-specific adapter sequence and said second sequencer-specific adapter sequence are compatible with sequencing by DNA nanoball technology. In some aspects, said first sequencer-specific adapter sequence and said second sequencer-specific adapter sequence are compatible with nanopore-based sequencing technology.

Some embodiments relate to methods of identifying a clonally amplified nucleic acid sequence. Some aspects of these embodiments relate to methods of identifying a clonally amplified nucleic acid sequence, comprising the steps of obtaining a first nucleic acid sequence comprising a first molecular tag sequence and a first target sequence having a first length; obtaining a second nucleic acid sequence comprising a second molecular tag sequence and a second target sequence having a second length; and discarding said second nucleic acid sequence if said second nucleic acid sequence comprises a second molecular tag sequence that is identical to said first molecular tag sequence, said second target sequence is identical to said first target sequence, and said second target sequence length is identical to said first target sequence length. In some aspects, if said second nucleic acid sequence comprises a second molecular tag sequence that is identical to said first molecular tag sequence, said second target sequence is identical to said first target sequence, and said second target sequence length is identical to said first target sequence length, then said second nucleic acid sequence and said first nucleic acid sequence are related by clonal amplification. In some aspects, said first nucleic acid sequence is generated through the annealing of a first primer comprising a first random oligonucleotide sequence. In some aspects, said second nucleic acid sequence is generated through the annealing of a second primer comprising a second random oligonucleotide sequence. In some aspects, each of said first random oligonucleotide sequence and said second random oligonucleotide sequence consist of 6 nucleotide bases. In some aspects, each of said first random oligonucleotide sequence and said second random oligonucleotide sequence consist of 7 nucleotide bases. In some aspects, each of said first random oligonucleotide sequence and said second random oligonucleotide sequence consist of 8 nucleotide bases. In some aspects, each of said first random oligonucleotide sequence and said second random oligonucleotide sequence consist of 9 nucleotide bases. In some aspects, each of said first random oligonucleotide sequence and said second random oligonucleotide sequence consist of 10 nucleotide bases. In some aspects, said first target sequence is generated through a process that results in a sequence of variable length. In some aspects, said first target sequence is generated through addition of at least one nucleotide to said first random oligonucleotide sequence. In some aspects, said nucleotide is selected from a pool comprising deoxynucleotide triphosphates and di-deoxynucleotide triphosphates. In some aspects, said nucleotide is added by a DNA polymerase enzyme that lacks strand displacement activity.

Some embodiments disclosed herein comprise a nucleic acid library. In some cases, a nucleic acid library comprises at least 100 library nucleic acids, each library nucleic acid comprising a first marker region comprising a first marker sequence identical to a first sequence in a marker sequence oligonucleotide population, a sample insert region having an independently determined length and a sample insert sequence corresponding to a contiguous subset of a sample nucleic acid sequence; a second marker region comprising a second marker sequence identical to a second sequence in a marker sequence oligonucleotide population, wherein the first marker sequence, the sample insert region length, and the second marker sequence independently vary among each library nucleic acid of said library. In some cases, each first marker region comprises at least 6, 7, 8, 9, or 10 nucleic acids. In some cases, each second marker region comprises at least 6, 7, 8, 9, or 10 nucleic acids. In some cases, each library nucleic acid comprises a first sequencing adapter and a second sequencing adapter. In some embodiments, the sample nucleic acid sequence comprises human, eukaryotic, prokaryotic, or viral genomic sequence. In some cases, the sample nucleic acid sequence comprises cDNA transcript sequence. In some cases, the sample nucleic acid sequence comprises genomic sequence from a patient suspected of harboring a genomic encoded illness, such as a genomic encoded illness associated with genomic repeat region length variation, a genomic encoded illness associated with duplication of a genomic region, a genomic encoded illness associated with deletion of a genomic region, a genomic encoded illness associated with a point mutation, or a genomic encoded illness associated with genomic repeat region length variation. In some cases, the nucleic acid library comprises at least 1,000 library nucleic acids, at least 10,000 library nucleic acids, at least 100,000 library nucleic acids, or at least 1,000,000 library nucleic acids. In some cases, the nucleic acid library comprises 100%, 99%, 98%, 97%, 96%, 95%, 94%, 93%, 92%, 91%, 90%, 85%, 80%, or 75% of a sample nucleic acid sequence distributed throughout the sample insertion sequence of the library nucleic acids of the library. In some cases, the nucleic acid library is sequenced. In some cases, the library is contained in a single volume, contained in a single tube, or contained in a single well.

Some embodiments disclosed herein comprise a nucleic acid library representative of a sample nucleic acid sequence. In some cases, this nucleic acid library representative of a sample nucleic acid sequence is a library comprising a plurality of library nucleic acids, each library nucleic acid comprising a first marker region comprising a first marker sequence, a sample insert region having an independently determined length and a sample insert sequence corresponding to a fragment of a sample nucleic acid sequence, and a second marker region comprising a second marker sequence, wherein the first marker sequence and the sample insert region length independently vary among said library nucleic acids, and wherein the first marker sequence does not occur adjacent to the sample insert region in the target sample sequence. In some cases, the second marker sequence does not occur adjacent to the target sequence region in the target sample sequence. In some cases, the second marker sequence independently varies among said library nucleic acids. In some cases, the second marker sequence comprises nucleic acid sequence adjacent to a region of interest. In some cases, each second marker region comprises at least 20 bases. In some cases, each second marker region comprises at least 225 bases. In some cases, each first marker region comprises at least 6, 7, 8, 9, or 10 nucleic acids. In some cases, each second marker region comprises at least 6, 7, 8, 9, or 10 nucleic acids. In some cases, each library nucleic acid comprises a first sequencing adapter and a second sequencing adapter. In some embodiments, the sample nucleic acid sequence comprises human, eukaryotic, prokaryotic, or viral genomic sequence. In some cases, the sample nucleic acid sequence comprises cDNA transcript sequence. In some cases, the sample nucleic acid sequence comprises genomic sequence from a patient suspected of harboring a genomic encoded illness, such as a genomic encoded illness associated with genomic repeat region length variation, a genomic encoded illness associated with duplication of a genomic region, a genomic encoded illness associated with deletion of a genomic region, a genomic encoded illness associated with a point mutation, or a genomic encoded illness associated with genomic repeat region length variation. In some cases, the nucleic acid library comprises at least 1,000 library nucleic acids, at least 10,000 library nucleic acids, at least 100,000 library nucleic acids, or at least 1,000,000 library nucleic acids. In some cases, the nucleic acid library comprises 100%, 99%, 98%, 97%, 96%, 95%, 94%, 93%, 92%, 91%, 90%, 85%, 80%, or 75% of a sample nucleic acid sequence distributed throughout the sample insertion sequence of the library nucleic acids of the library. In some cases, the nucleic acid library is sequenced. In some cases, the library is contained in a single volume, contained in a single tube, or contained in a single well.

Some embodiments disclosed herein comprise a composition comprising a first nucleic acid strand comprising a 5'sequence comprising at least 6 bases of indeterminate sequence, a 3' sequence comprising a fragment of a nucleic acid sample sequence, a 3' terminal end that cannot support strand extension, and at least one affinity tag, a second nucleic acid strand comprising a second strand oligo of intermediate sequence, wherein the second nucleic acid strand is annealed to the first nucleic acid strand. In some cases, the sequence of the first nucleic strand is not present in the nucleic acid sample sequence. In some cases, the sequence of the first nucleic acid strand comprises a 5' sequence of at least 8 bases of indeterminate sequence. In some cases the sequence of the second nucleic acid strand is not present in the nucleic acid sample sequence. In some cases, the sequence of the second nucleic acid strand is present in the nucleic acid sample sequence. In some cases, the affinity tag is bound at the 3' terminal position of the first nucleic acid strand. In some cases, the affinity tag comprises biotin. In some cases, the affinity tag comprises biotin and the affinity tag is bound at the 3' terminal position of the first nucleic acid strand. In some cases, the first nucleic acid strand comprises a 3' di-deoxy nucleoside. In some cases, the first nucleic acid strand is terminated by incorporation of a ddNTP at the 3' terminal position such as a biotin-tagged ddNTP at the 3' terminal position. In some cases, the composition comprises a binding agent bound to the affinity tag. In some cases, the composition comprises a streptavidin moiety bound to the affinity tag. In some cases, the affinity tag comprises biotin bound to a dideoxy moiety at the 3' end of the first nucleic acid strand, wherein the biotin is bound to a streptavidin moiety. In some cases, the composition comprises a nucleic acid extension mixture. In some cases, the composition comprises a DNA polymerase having strand-displacement activity, a DNA polymerase having thermostable activity up to at least 95° C., or a DNA polymerase capable of incorporating a biotin-labeled ddNTP at the 3' end of an extending nucleic acid. In some cases, the composition comprises SEQUENASE (Amersham Biosciences) or THERMOSEQUENASE (Amersham Biosciences).

A tagged nucleic acid library may be obtained by methods consistent with the disclosure. In some cases, a method of generating a tagged nucleic acid library comprises the steps of annealing a first oligo population to a library template, performing library template-directed nucleic acid extension from the annealed first oligo population, affinity tagging the first extension products, terminating the library template-directed nucleic acid extension to produce a population of first extension products of indeterminate length, adding a second oligo sequence near the 3' end of the first extension product, such that a tagged library of nucleic acid molecules is generated comprising nucleic acids each independently comprising a first oligo sequence, a template derived nucleic acid sequence of indeterminate length, and a second oligo sequence. In some cases, the first oligo originates from a first random oligo population. In some cases, the second oligo originates from a second random oligo population. In some cases, the library template-directed nucleic acid extension comprises incorporation of an affinity tag into said first extension product. In some cases, terminating the library template-directed nucleic acid extension comprises incorporation of a ddNTP, incorporation of a ddNTP comprising an affinity tag, or incorporation of a biotin tagged ddNTP. In some cases, the first extension product is affinity purified. In some cases, adding a second oligo sequence near the 3' end of the first extension product comprises annealing a population of oligos comprising said second oligo sequence to said first extension product, and contacting the composition to a nucleic acid extension cocktail comprising a DNA polymerase having strand-displacement activity to form a second extension product annealed to the first extension product. In some cases, the DNA polymerase has thermostable activity up to at least 95° C. In some cases, adding a second oligo sequence extension is performed on a first extension product bound to an affinity tag to form a second extension product. In some cases, the methods comprise washing the affinity-tag bound complex comprising the first extension product and second extension product. In some cases, the method is performed in a single tube and completed within 7 hours, within 2 hours, or within 1 hour. In some cases, the methods comprise sequencing at least one member of the labeled library. In some cases, the library template comprises genomic DNA or messenger RNA. In some cases, the methods comprise sequencing the library.

A labeled nucleic acid library may be obtained by methods consistent with the disclosure. In some cases, a method of generating a labeled nucleic acid library comprises the steps of contacting a denatured library template to a first oligo population, an extension mix comprising dNTP and biotin-labeled ddNTP, and a low-processivity thermostable DNA polymerase to form a first strand composition, incubating the first strand composition in a temperature gradient incubator such that said first strand composition is subjected to a temperature ramp from a first oligo population annealing temperature to a denaturing temperature, contacting said first strand composition to at least one streptavidin moiety, contacting said bound first strand composition to a second oligo population, an extension mix comprising dNTP and a strand-displacing DNA polymerase, to form a second strand composition, incubating said second strand composition at an annealing temperature, incubating said second strand composition at an extension temperature, contacting said second strand composition to a PCR amplification composition comprising a first primer comprising a first sequencing adapter sequence and sequence complementary to a region of said first random oligo population, a second primer comprising a second sequencing adapter sequence and sequence complementary to a region of said second random oligo population to form a PCR composition, and subjecting the PCR amplification composition and second strand composition to PCR amplification thermocycling conditions. In some cases, the DNA polymerase is capable of incorporating a biotin-labeled ddNTP at the 3' end of an extending nucleic acid. In some cases, the annealing temperature and the extension temperature are different. In some cases, the annealing temperature and the extension temperature are the same. In some cases, the first oligo population comprises oligonucleotides having randomly determined sequences. In some cases, the second oligo population comprises oligonucleotides having randomly determined sequences. In some cases, the second oligo population comprises oligonucleotides having determined sequences selected to anneal to a target sequence. In some cases, the method is performed in a single tube. In some cases, the method is completed within 7 hours, within 2 hours, or within 1 hour. In some cases, the method comprises sequencing at least one member of the labeled nucleic acid library.

A nucleic acid sample may be fragmented into library constituents by methods consistent with this disclosure. In some cases, a method of fragmenting a nucleic acid sample into library constituents suitable for sequencing comprises the steps of contacting the nucleic acid sample to a population of oligonucleotides, a DNA polymerase, dNTPs, a buffer suitable for nucleic acid extension, an affinity tag and a nucleic acid chain extension terminating moiety, providing conditions suitable for annealing and nucleic acid extension, contacting the nucleic acid sample to an affinity-tag binding moiety, and separating bound from unbound components, wherein the bound components comprise library constituents suitable for sequencing. In some cases, the affinity tag is a biotin-tagged NTP, a biotin-tagged dNTP, or a biotin-tagged ddNTP. In some cases, the nucleic acid chain extension terminating moiety is a biotin-tagged ddNTP. In some cases, the DNA polymerase has strand-displacement activity. In some cases, the DNA polymerase has thermostable activity up to at least 95° C. In some cases, the DNA polymerase is capable of incorporating a biotin-labeled ddNTP at the 3' end of an extending nucleic acid. In some cases, the DNA polymerase is SEQUENASE (Amersham Biosciences) or THERMOSEQUENASE (Amersham Biosciences). In some cases, the nucleic acid sample is not subjected to conditions sufficient to break a substantial amount of covalent bonds in the sample. In some cases, the library constituents are isolated without size fractionation, electrophoresis, or column purification. In some cases, the nucleic acid extension comprises incorporation of at least 100 bases or at least 200 bases. In some cases, the nucleic acid extension comprises incorporation of up to 4 kb or up to 5 kb. In some cases the method is completed in a single tube. In some cases, the method is completed within 7 hours, within 2 hours, or within 1 hour. In some cases, 100% of the nucleic acid sample is represented in the sequence of the library constituents. In some cases, 99%, 98%, 97%, 96%, 95%, 94%, 93%, 92%, 91%, 90%, 85%, 80%, or 75% of the nucleic acid sample is represented in the sequence of the library constituents. In some cases, the method comprises sequencing at least one of the library constituents.

Tagged fragments of a nucleic acid sample may be generated consistent with the methods disclosed. In some cases, a method of generating tagged fragments of a nucleic acid sample comprises the steps of contacting the nucleic acid sample to an oligonucleotide library comprising an oligonucleotide having a sequence not identical to any sequence of the nucleic acid sample and a nucleic acid extension composition comprising dNTP, an affinity tag, and a DNA polymerase, to form affinity-tagged, oligo-tagged fragments of the nucleic acid sample and affinity purifying the affinity-tagged, oligo-tagged fragments of the nucleic acid sample. In some cases, substantially no covalent bonds of the nucleic acid sample are disrupted. In some cases, the affinity-tagged, oligo-tagged fragments of the nucleic acid sample are not subjected to column purification. In some cases, the extension composition comprises at least one species of ddNTP. In some cases the composition comprises only one species of ddNTP, such as only ddATP, only ddGTP, only ddCTP or only ddGTP. Alternately, in some cases the composition comprises a combination of two, three, or four ddNTP species. In some cases the composition comprises a ddNTP comprising a base other than A, T, G, or C, such as ddUTP (uracil), ddITP (inosine), or another base. In some cases, the extension composition comprises an affinity-tagged dNTP or an affinity-tagged ddNTP. In some cases, the method comprises contacting the affinity-tagged, oligo-tagged fragments of the nucleic acid sample to at least one streptavidin bead. In some cases, the DNA polymerase has strand-displacement, thermostable activity up to at least 95° C., or is capable of incorporating a biotin-labeled ddNTP at the 3' end of an extending nucleic acid. In some cases, the DNA polymerase is SEQUENASE (Amersham Biosciences) or THERMOSEQUENASE (Amersham Biosciences). In some cases, the nucleic acid extension comprises incorporation of at least 100 bases or at least 200 bases. In some cases, the nucleic acid extension comprises incorporation of up to 4 kb or up to 5 kb. In some cases the method is completed in a single tube. In some cases, the method is completed within 7 hours, within 2 hours, or within 1 hour. In some cases, 100% of the nucleic acid sample is represented in the sequence of the library constituents. In some cases, 99%, 98%, 97%, 96%, 95%, 94%, 93%, 92%, 91%, 90%, 85%, 80%, or 75% of the nucleic acid sample is represented in the sequence of the library constituents. In some cases, the method comprises sequencing at least one of the tagged fragments.

A data set comprising non-identical, tagged nucleic acid molecule sequences each comprising a subset of sequence from a nucleic acid sample may be generated consistent with the methods disclosed. In some cases, a method of generating a computer-stored data set comprising at least 1000, 2000, 3000, 4000, 5000, 6000, 7000, 8000, 9000, 10,000, 20,000, 30,000, 40,000, 50,000, 60,000, 70,000, 80,000, 90,000, 100,000 or more than 100,000 non-identical, tagged nucleic acid molecule sequences each comprising a subset of sequence from a nucleic acid sample comprises storing on a computer a first nucleic acid molecule sequence comprising a first 5' molecular tag sequence, a first insertion sequence having a first length from said nucleic acid sample, and a first 3' molecular tag sequence, storing on a computer a second nucleic acid molecule sequence comprising a second 5' molecular tag sequence, a second insertion sequence having a second length, and a second 3' molecular tag sequence, and excluding from said dataset said second double-stranded nucleic acid molecule sequence if: said first 5' molecular tag sequence is identical to said second 5' molecular tag sequence; said first 3' molecular tag sequence is identical to said second 3' molecular tag sequence; said second insertion sequence is identical to said first insertion sequence; and said second target sequence length is identical to said first target sequence length. In some cases, the method comprises discarding the second double-stranded nucleic acid molecule if the second target sequence differs from the first sequence by not more than five bases. In some cases, the method comprises discarding the second double-stranded nucleic acid molecule if the second target sequence differs from the first sequence by not more than one base per hundred bases of insertion. In some cases, the method comprises discarding the second double-stranded nucleic acid molecule if the second target sequence differs from the first sequence by presence of a deletion, and the second target sequence is shorter than the first target sequence length by the length of the deletion. In some cases, the method comprises discarding the second double-stranded nucleic acid molecule if the second target sequence differs from the first sequence by presence of an insertion, and the second target sequence is longer than the first target sequence by the length of the insertion.

A nucleic acid sample may be library-packaged consistent with the methods disclosed. In some cases, a method of library-packaging a nucleic acid sample comprises the steps of contacting a first oligo population to the nucleic acid sample under conditions sufficient to allow annealing of at least some members of the first oligo population to the nucleic acid sample, performing a nucleic acid sample-directed first nucleic acid extension from annealed members of the first oligo population to produce a population of first extension products having an undetermined number of bases complementary to said template incorporated therein, affinity tagging the population of first extension products, terminating the sample template-directed nucleic acid extension to form a first strand library, and affinity purifying the first strand library. In some cases, the conditions sufficient to allow annealing of at least some members of the first oligo population to the nucleic acid sample are sufficient to allow substantial nonspecific annealing. In some cases, the conditions sufficient to allow annealing of at least some members of the first oligo population to the nucleic acid sample are sufficient to prohibit substantial nonspecific annealing. In some cases, performing a nucleic acid sample-directed first nucleic acid extension comprises contacting with a nucleotide polymerizing enzyme capable of incorporating ddNTP or an affinity-tagged ddNTP into an extending nucleic acid chain. In some cases, the affinity tag is biotin. In some cases, performing a nucleic acid sample-directed first nucleic acid extension comprises contacting with a nucleotide polymerizing enzyme capable of incorporating an affinity-tagged ddNTP into an extending nucleic acid chain. In some cases, performing a nucleic acid sample-directed first nucleic acid extension comprises contacting with a nucleotide polymerizing enzyme capable of incorporating a biotin-tagged ddNTP into an extending nucleic acid chain. In some cases, the method comprises contacting the first strand library to a second oligo population under conditions sufficient to allow random annealing of at least some members of the second oligo population to the first strand library, and performing a first-strand directed second nucleic acid extension from annealed members of the second oligo population to produce a library of nucleic acid molecules comprising a first oligo region, a region of indeterminate length comprising sequence of the nucleic acid sample, and a second oligo region. In some cases, the method comprises adding a sequencing primer to each end of at least some molecules of the library of nucleic acid molecules. In some cases, the method comprises sequencing the library of nucleic acid molecules to form a library sequence data set. In some cases, the method comprises excluding from the data set any one sequence of a pair of library molecule sequences that share an identical first oligo sequence, an identical second oligo sequence and a nucleic acid sample sequence of identical length. In some cases, the number of sequenced library molecules having a first nucleic acid sample sequence corresponds to the number of molecules having the first nucleic acid sequence in the nucleic acid sample. In some cases, the nucleic acid sample comprises RNA sequence or messenger RNA sequence. In some cases, the nucleic acid sample is obtained from a population of 100 cells, 50 cells, 20 cells, 10 cells, 5 cells, or a single cell. In some cases, the nucleic acid sample comprises repetitive sequence. In some cases, the method comprises contacting the first strand library to a second oligo population under conditions sufficient to allow annealing of any members of the second oligo population to the first strand library only if the oligos are reverse complements of the first strand library at the annealed bases, and performing a first-strand directed second nucleic acid extension from annealed members of the second oligo population to produce a first library of nucleic acid molecules comprising a first oligo region and a region of indeterminate length comprising sequence of the nucleic acid sample. In some cases, the method comprises contacting the first library of nucleic acid molecules with a third oligo population comprising sequence identical to a 3' adapter region of the first oligo population, and a fourth oligo population comprising sequence that is identical to first library sequence interior to a second primer annealing site, under conditions sufficient to allow annealing of any members of the fourth oligo population to the first strand library only if the oligos are reverse complements of the first strand library at the annealed bases. In some cases, the method comprises subjecting the third oligonucleotide population, fourth oligonucleotide population and first library to polymerase chain reaction amplification to form a second library. In some cases, the method comprises sequencing the second library.

INCORPORATION BY REFERENCE

All publications, patents, and patent applications mentioned in this specification are herein incorporated by reference to the same extent as if each individual publication, patent, or patent application was specifically and individually indicated to be incorporated by reference. In particular, the contents of International Publication No. WO 2013/177220 A2, published Nov. 28, 2013, are hereby incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A depicts Step 1, FIG. 1B depicts Step 2, FIG. 1C depicts Step 3, FIG. 1D and FIG. 1E depicts Step 4, FIG. 1F depicts Step 5, and FIG. 1G depicts the resulting library molecule ready for sequencing.

FIG. 3A illustrates Rapid Library Prep (RLP), FIG. 3B illustrates RNA Rapid Library Prep (R_RLP), FIG. 3C illustrates Long Read Rapid Library Prep (L_RLP), and FIG. 3D illustrates Targeted Rapid Library Prep (T_RLP).

FIG. 4A depicts Rapid Library Prep (RLP), FIG. 4B depicts RNA Rapid Library Prep (R_RLP), FIG. 4C depicts Long Read Rapid Library Prep (L_RLP), and FIG. 4D depicts Targeted Rapid Library Prep (T_RLP).

FIG. 5A shows a NEXTERA library (left side) and FIG. 5B shows a Rapid Library Prep library (right side).

FIG. 6A shows a NEXTERA library (left side) and FIG. 6B shows a Rapid Library Prep library (right side). Input was 1 ng of DNA with 12 cycles of PCR for NEXTERA and 15 cycles for the Rapid Library Prep.

FIG. 7A-7B illustrate a comparison of the guanine-cytosine (GC) content for two libraries. FIG. 7A shows a NEXTERA library (left side) and FIG. 7B shows a Rapid Library Prep library (right side). Input was 1 ng of DNA with 12 cycles of PCR for NEXTERA and 15 cycles for the Rapid Library Prep.

FIG. 8A shows a NEXTERA library (left side) and FIG. 8B shows a Rapid Library Prep library (right side). Input was 1 ng of DNA with 12 cycles of PCR for NEXTERA and 15 cycles for the Rapid Library Prep.

FIG. 9A shows an increase of number of small fragments as the number of cycles increases to 15 PCR cycles. FIG. 9B shows the amount of high quality amplification product after 6 PCR cycles. FIG. 9C shows the amount of high quality amplification product after 9 PCR cycles. FIG. 9D shows the amount of high quality amplification product after 12 PCR cycles. FIG. 9E shows the amount of high quality amplification product after 15 PCR cycles.

FIG. 10A shows base distribution (left panel), FIG. 10B shows quality by cycle (center) and FIG. 10C shows GC bias (right panel).

FIG. 14A shows counts of read with 0 mismatches. FIG. 14B shows counts of read with 1 mismatch.

FIG. 15A shows counts of read with 0 mismatches. FIG. 15B shows counts of read with 1 mismatch. FIG. 15C shows counts of read with 2 mismatches.

FIG. 17A depicts a plurality of first strand templates with or without primers annealed to them. FIG. 17B depicts two primers annealed to two first strand templates, respectively. FIG. 17C depicts a plurality of primers.

FIG. 18A depicts two primers annealed to a template. FIG. 18B depicts the amplified PCR product.

FIG. 19 provides a cancer risk panel.

DETAILED DESCRIPTION OF THE INVENTION

Figure 1:
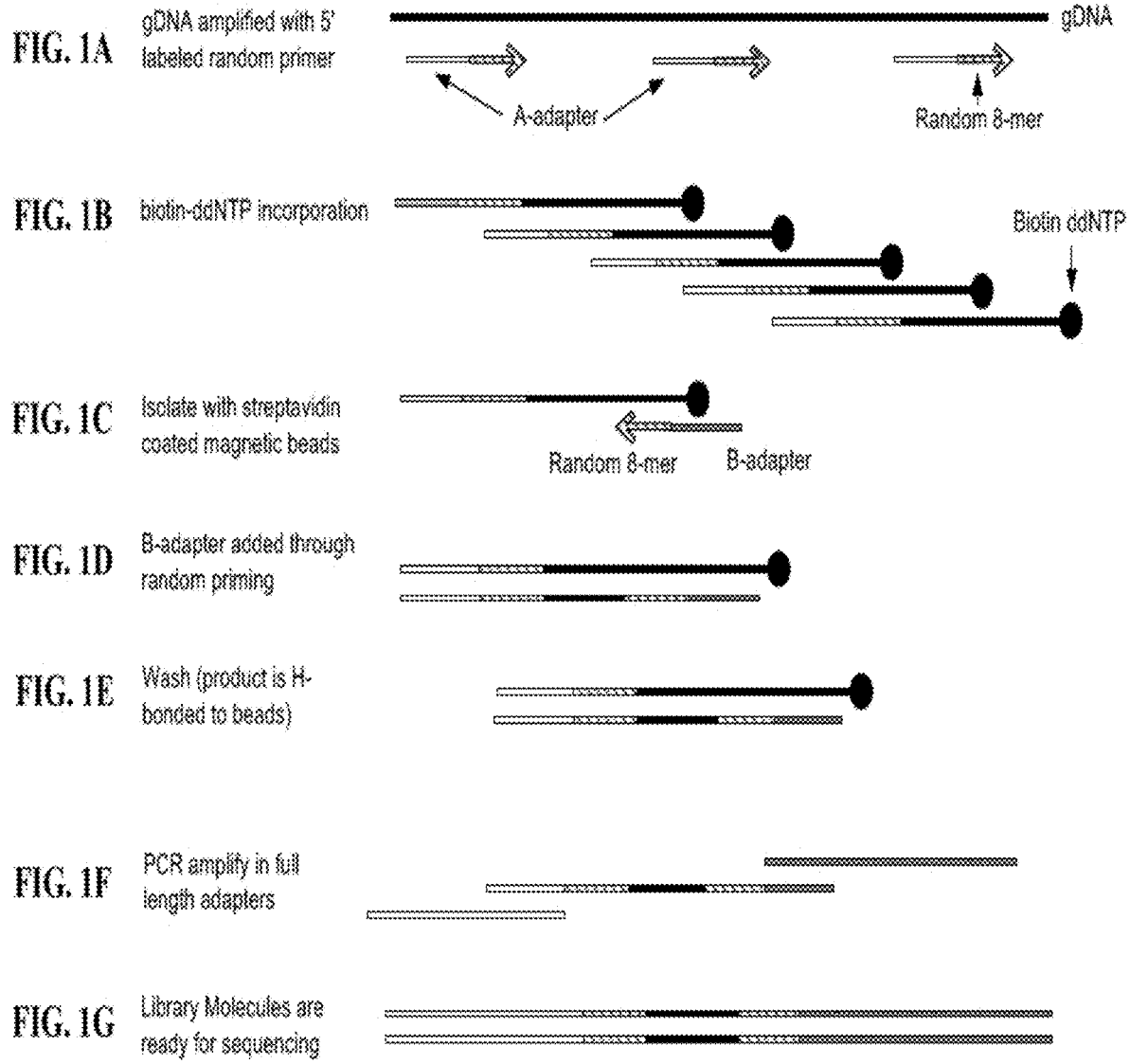
FIG. 1A-1G depict a schematic of the Rapid Library Prep utilizing genomic DNA as the target nucleic acid sample.

The present technology relates to methods for sequencing polymers such as nucleic acids. Described herein are methods and compositions for generating a population of non-identical, tagged nucleic acid molecules, each comprising a subset of sequence from a target nucleic acid sample. These methods and compositions may allow for targeted sequencing of nucleic acid molecules as well as sample preparation and analysis methods for de novo sequencing for assembly of genomes and quantitative gene expression.

Definitions

A partial list of relevant definitions is as follows.

"Amplified nucleic acid" or "amplified polynucleotide" is any nucleic acid or polynucleotide molecule whose amount has been increased at least two fold by any nucleic acid amplification or replication method performed in vitro as compared to its starting amount. For example, an amplified nucleic acid is obtained from a polymerase chain reaction (PCR) which can, in some instances, amplify DNA in an exponential manner (for example, amplification to $2^n$ copies in n cycles). Amplified nucleic acid can also be obtained from a linear amplification.

"Amplification product" can refer to a product resulting from an amplification reaction such as a polymerase chain reaction.

An "amplicon" is a polynucleotide or nucleic acid that is the source and/or product of natural or artificial amplification or replication events.

The term "biological sample" or "sample" generally refers to a sample or part isolated from a biological entity. The biological sample may show the nature of the whole and examples include, without limitation, bodily fluids, dissociated tumor specimens, cultured cells, and any combination thereof. Biological samples can come from one or more individuals. One or more biological samples can come from the same individual. One non limiting example would be if one sample came from an individual's blood and a second sample came from an individual's tumor biopsy. Examples of biological samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, microbiota, meconium, breast milk and/or other excretions. The samples may include nasopharyngeal wash. Examples of tissue samples of the subject may include but are not limited to, connective tissue, muscle tissue, nervous tissue, epithelial tissue, cartilage, cancerous or tumor sample, or bone. The sample may be provided from a human or animal. The sample may be provided from a mammal, including vertebrates, such as murines, simians, humans, farm animals, sport animals, or pets. The sample may be collected from a living or dead subject. The sample may be collected fresh from a subject or may have undergone some form of pre-processing, storage, or transport.

"Bodily fluid" generally can describe a fluid or secretion originating from the body of a subject. In some instances, bodily fluids are a mixture of more than one type of bodily fluid mixed together. Some non-limiting examples of bodily fluids are: blood, urine, bone marrow, spinal fluid, pleural fluid, lymphatic fluid, amniotic fluid, ascites, sputum, or a combination thereof.

"Complementary" or "complementarity" can refer to nucleic acid molecules that are related by base-pairing. Complementary nucleotides are, generally, A and T (or A and U), or C and G (or G and U). Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100%) complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Hybridization temperatures are generally at least about 2° C. to about 6° C. lower than melting temperatures ($T_m$).

A "barcode" or "molecular barcode" is a material for labeling. The barcode can label a molecule such as a nucleic acid or a polypeptide. The material for labeling is associated with information. A barcode is called a sequence identifier (i.e. a sequence-based barcode or sequence index). A barcode is a particular nucleotide sequence. A barcode is used as an identifier. A barcode is a different size molecule or different ending points of the same molecule. Barcodes can include a specific sequence within the molecule and a different ending sequence. For example, a molecule that is amplified from the same primer and has 25 nucleotide positions is different than a molecule that is amplified and has 27 nucleotide positions. The addition positions in the 27mer sequence is considered a barcode. A barcode is incorporated into a polynucleotide. A barcode is incorporated into a polynucleotide by many methods. Some non-limiting methods for incorporating a barcode can include molecular biology methods. Some non-limiting examples of molecular biology methods to incorporate a barcode are through primers (e.g., tailed primer elongation), probes (i.e., elongation with ligation to a probe), or ligation (i.e., ligation of known sequence to a molecule).

A barcode is incorporated into any region of a polynucleotide. The region is known. The region is unknown. The barcode is added to any position along the polynucleotide. The barcode is added to the 5' end of a polynucleotide. The barcode is added to the 3' end of the polynucleotide. The barcode is added in between the 5' and 3' end of a polynucleotide. A barcode is added with one or more other known sequences. One non-limiting example is the addition of a barcode with a sequence adapter.

Barcodes is associated with information. Some non-limiting examples of the type of information a barcode is associated with information include: the source of a sample; the orientation of a sample; the region or container a sample was processed in; the adjacent polynucleotide; or any combination thereof.

In some cases, barcodes is made from combinations of sequences (different from combinatorial barcoding) and is used to identify a sample or a genomic coordinate and a different template molecule or single strand the molecular label and copy of the strand was obtained from. In some cases a sample identifier, a genomic coordinate and a specific label for each biological molecule may be amplified together. Barcodes, synthetic codes, or label information can also be obtained from the sequence context of the code (allowing for errors or error correcting), the length of the code, the orientation of the code, the position of the code within the molecule, and in combination with other natural or synthetic codes.

Barcodes is added before pooling of samples. When the sequences are determined of the pooled samples, the barcode is sequenced along with the rest of the polynucleotide. The barcode is used to associate the sequenced fragment with the source of the sample.

Barcodes can also be used to identify the strandedness of a sample. One or more barcodes is used together. Two or more barcodes is adjacent to one another, not adjacent to one another, or any combination thereof.

Barcodes is used for combinatorial labeling.

"Combinatorial labeling" is a method by which two or more barcodes are used to label. The two or more barcodes can label a polynucleotide. The barcodes, each, alone is associated with information. The combination of the barcodes together is associated with information. In some cases a combination of barcodes is used together to determine in a randomly amplified molecule that the amplification occurred from the original sample template and not a synthetic copy of that template. In some cases, the length of one barcode in combination with the sequence of another barcode is used to label a polynucleotide. In some cases, the length of one barcode in combination with the orientation of another barcode is used to label a polynucleotide. In other cases, the sequence of one barcode is used with the orientation of another barcode to label a polynucleotide. In some cases the sequence of a first and a second bar code, in combination with the distance in nucleotides between them, is used to label or to identify a polynucleotide.

"Degenerate" can refer to a nucleic acid or nucleic acid region that is comprised of random bases. The terms "degenerate" and "random" is used interchangeably when referring to nucleic acid sequences (e.g., "degenerate primers" or "random primers" or "degenerate probes" or "random probes"). The degenerate region is of variable length. The degenerate region can comprise some portion of the whole nucleic acid (e.g., a semi-degenerate primer). The degenerate region can comprise the whole nucleic acid (e.g., a "degenerate primer"). A degenerate nucleic acid mix or semi-degenerate nucleic acid mix may be comprised of every possible combination of base pairs, less than every possible combination of base pairs, or some combination of base pairs, a few combinations of base pairs, or a single base pair combination. A degenerate primer mix or semi-degenerate primer mix can comprise mixes of similar but not identical primers.

"Double-stranded" can refer to two polynucleotide strands that have annealed through complementary base-pairing.

"Known oligonucleotide sequence" or "known oligonucleotide" or "known sequence" can refer to a polynucleotide sequence that is known. A known oligonucleotide sequence can correspond to an oligonucleotide that has been designed, e.g., a universal primer for next generation sequencing platforms (e.g., Illumina, 454), a probe, an adaptor, a tag, a primer, a molecular barcode sequence, an identifier. A known sequence can comprise part of a primer. A known oligonucleotide sequence may not actually be known by a particular user but is constructively known, for example, by being stored as data which may be accessible by a computer. A known sequence may also be a trade secret that is actually unknown or a secret to one or more users but may be known by the entity who has designed a particular component of the experiment, kit, apparatus or software that the user is using.

"Library" can refer to a collection of nucleic acids. A library can contain one or more target fragments. In some instances the target fragments is amplified nucleic acids. In other instances, the target fragments is nucleic acid that is not amplified. A library can contain nucleic acid that has one or more known oligonucleotide sequence(s) added to the 3' end, the 5' end or both the 3' and 5' end. The library may be prepared so that the fragments can contain a known oligonucleotide sequence that identifies the source of the library (e.g., a molecular identification barcode identifying a patient or DNA source). In some instances, two or more libraries is pooled to create a library pool. Libraries may also be generated with other kits and techniques such as transposon mediated labeling, or "tagmentation" as known in the art. Kits may be commercially available, such as the Illumina NEXTERA kit (Illumina, San Diego, Calif.).

"Locus specific" or "loci specific" can refer to one or more loci corresponding to a location in a nucleic acid molecule (e.g., a location within a chromosome or genome). In some instances, a locus is associated with genotype. In some instances loci may be directly isolated and enriched from the sample, e.g., based on hybridization and/or other sequence-based techniques, or they may be selectively amplified using the sample as a template prior to detection of the sequence. In some instances, loci may be selected on the basis of DNA level variation between individuals, based upon specificity for a particular chromosome, based on CG content and/or required amplification conditions of the selected loci, or other characteristics that will be apparent to one skilled in the art upon reading the present disclosure. A locus may also refer to a specific genomic coordinate or location in a genome as denoted by the reference sequence of that genome.

"Long nucleic acid" can refer to a polynucleotide longer than 1, 2, 3, 4, 5, 6, 7, 8, 9, or 10 kilobases.

The term "melting temperature" or "$T_m$" commonly refers to the temperature at which a population of double-stranded nucleic acid molecules becomes half dissociated into single strands. Equations for calculating the $T_m$ of nucleic acids are well known in the art. One equation that gives a simple estimate of the $T_m$ value is as follows: $T_m=81.5+16.6(\log 10[Na^+])0.41(\%[G+C])-675/n-1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual,* 3rd Ed., Cold Spring Harbor Laboratory Press (2001)). Other references can include more sophisticated computations, which take structural as well as sequence characteristics into account for the calculation of $T_m$.

"Nucleotide" can refer to a base-sugar-phosphate combination. Nucleotides are monomeric units of a nucleic acid sequence (e.g., DNA and RNA). The term nucleotide includes naturally and non-naturally occurring ribonucleoside triphosphates ATP, TTP, UTP, CTG, GTP, and ITP, for example and deoxyribonucleoside triphosphates such as dATP, dCTP, dITP, dUTP, dGTP, dTTP, or derivatives thereof. Such derivatives can include, for example, [aS] dATP, 7-deaza-dGTP and 7-deaza-dATP, and, for example, nucleotide derivatives that confer nuclease resistance on the nucleic acid molecule containing them. The term nucleotide as used herein also refers to dideoxyribonucleoside triphosphates (ddNTPs) and their derivatives. Illustrative examples of dideoxyribonucleoside triphosphates include, ddATP, ddCTP, ddGTP, ddITP, ddUTP, ddTTP, for example. Other ddNTPs are contemplated and consistent with the disclosure herein, such as dd (2-6 diamino) purine.

"Polymerase" can refer to an enzyme that links individual nucleotides together into a strand, using another strand as a template.

"Polymerase chain reaction" or "PCR" can refer to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, is amplified to obtain thousands, millions, or billions of replicates. The polymerase chain reaction is used to detect and measure very small amounts of DNA and to create customized pieces of DNA.

The terms "polynucleotides" and "oligonucleotides" may include but is not limited to various DNA, RNA molecules, derivatives or combination thereof. These may include species such as dNTPs, ddNTPs, 2-methyl NTPs, DNA, RNA, peptide nucleic acids, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA. "Oligonucleotides," generally, are polynucleotides of a length suitable for use as primers, generally about 6-50 bases but with exceptions, particularly longer, being not uncommon.

A "primer" generally refers to an oligonucleotide used to prime nucleotide extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific nucleic acid region.

"Primer extension product" generally refers to the product resulting from a primer extension reaction using a contiguous polynucleotide as a template, and a complementary or partially complementary primer to the contiguous sequence.

"Sequencing," "sequence determination," and the like generally refers to any and all biochemical methods that may be used to determine the order of nucleotide bases in a nucleic acid.

A "sequence" as used herein refers to a series of ordered nucleic acid bases that reflects the relative order of adjacent nucleic acid bases in a nucleic acid molecule, and that can readily be identified specifically though not necessarily uniquely with that nucleic acid molecule. Generally, though not in all cases, a sequence requires a plurality of nucleic acid bases, such as 5 or more bases, to be informative although this number may vary by context. Thus a restriction endonuclease may be referred to as having a 'sequence' that it identifies and specifically cleaves even if this sequence is only four bases. A sequence need not 'uniquely map' to a fragment of a sample. However, in most cases a sequence must contain sufficient information to be informative as to its molecular source.

As used herein, a sequence 'does not occur' in a sample if that sequence is not contiguously present in the entire sequence of the sample. Sequence that does not occur in a sample is not naturally occurring sequence in that sample.

As used herein, a library is described as "representative of a sample" if the library comprises an informative sequence of the sample. In some cases an informative sequence comprises about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% of a sample sequence. In some cases an informative sequence comprises about 90%, 90%, or greater than 90% of a sample sequence.

As used herein, a sequence or sequence length is described as 'independently determined' if the sequence or sequence length is not determined by or a function of a second sequence or sequence length. Random events such as incorporation of a terminating ddNTP base or nonspecific or less than exact annealing of an oligo to a template are generally events that are independently determined, such that a library of molecules resulting from such events comprises substantial variation in sequence or sequence length.

As used herein, a sequence is described as 'indeterminate' if it is not determined by template-mediated synthesis. Thus a nucleic acid molecule originating from synthesis off of a template primed by annealing to the template of a random oligomer may comprise a region of template-directed sequence resulting from the template-driven nucleic acid extension, and an 'indeterminate sequence' corresponding to the oligomer sequence providing the 3' OH group from which template-driven extension reaction builds. In some cases the oligonucleotide annealing is imperfect, such that the oligomer sequence is not the exact reverse complement of the molecule to which it binds.

"Subdividing" as used herein in the context of a sample sequence refers to breaking a sequence into subsequences, each of which remains a sequence as defined herein. In some instances subdividing and fractionating are used interchangeably.

A "contig" refers to a nucleotide sequence that is assembled from two or more constituent nucleotide sequences that share common or overlapping regions of sequence homology. For example, the nucleotide sequences of two or more nucleic acid fragments is compared and aligned in order to identify common or overlapping sequences. Where common or overlapping sequences exist between two or more nucleic acid fragments, the sequences (and thus their corresponding nucleic acid fragments) is assembled into a single contiguous nucleotide sequence.

The term "biotin," as used herein, is intended to refer to biotin (5-[(3aS,4S,6aR)-2-oxohexahydro-1H-thieno[3,4-d]imidazol-4-yl]pentanoic acid) and any biotin derivatives and analogs. Such derivatives and analogs are substances which form a complex with the biotin binding pocket of native or modified streptavidin or avidin. Such compounds include, for example, iminobiotin, desthiobiotin and streptavidin affinity peptides, and also include biotin-.epsilon.-N-lysine, biocytin hydrazide, amino or sulfhydryl derivatives of 2-iminobiotin and biotinyl-ε-aminocaproic acid-N-hydroxysuccinimide ester, sulfo-succinimide-iminobiotin, biotin-bromoacetylhydrazide, p-diazobenzoyl biocytin, 3-(N-maleimidopropionyl) biocytin. "Streptavidin" can refer to a protein or peptide that can bind to biotin and can include: native egg-white avidin, recombinant avidin, deglycosylated forms of avidin, bacterial streptavidin, recombinant streptavidin, truncated streptavidin, and/or any derivative thereof.

A "subject" generally refers to an organism that is currently living or an organism that at one time was living or an entity with a genome that can replicate. The methods, kits, and/or compositions of the disclosure is applied to one or more single-celled or multi-cellular subjects, including but not limited to microorganisms such as bacterium and yeast; insects including but not limited to flies, beetles, and bees; plants including but not limited to corn, wheat, seaweed or algae; and animals including, but not limited to: humans; laboratory animals such as mice, rats, monkeys, and chimpanzees; domestic animals such as dogs and cats; agricultural animals such as cows, horses, pigs, sheep, goats; and wild animals such as pandas, lions, tigers, bears, leopards, elephants, zebras, giraffes, gorillas, dolphins, and whales. The methods of this disclosure can also be applied to germs or infectious agents, such as viruses or virus particles or one or more cells that have been infected by one or more viruses.

A "support" is solid, semisolid, a bead, a surface. The support is mobile in a solution or is immobile.

The term "unique identifier" may include but is not limited to a molecular bar code, or a percentage of a nucleic acid in a mix, such as dUTP.

"Repetitive sequence" as used herein refers to sequence that does not uniquely map to a single position in a nucleic acid sequence data set. Some repetitive sequence is conceptualized as integer or fractional multiples of a repeating unit of a given size and exact or approximate sequence.

A "primer" as used herein refers to an oligonucleotide that anneals to a template molecule and provides a 3' OH group from which template-directed nucleic acid synthesis can occur. Primers comprise unmodified deoxynucleic acids in many cases, but in some cases comprise alternate nucleic acids such as ribonucleic acids or modified nucleic acids such as 2' methyl ribonucleic acids.

As used herein, a nucleic acid is double-stranded if it comprises hydrogen-bonded base pairings. Not all bases in the molecule need to be base-paired for the molecule to be referred to as double-stranded.

The term "about" as used herein in reference to a number refers to that number plus or minus up to 10% of that number. The term used in reference to a range refers to a range having a lower limit as much as 10% below the stated lower limit, and an upper number up to 10% above the stated limit.

Methods and Compositions

Next Generation Sequencing (NGS), or massively parallel sequencing has dramatically reduced the cost of DNA sequencing and has enabled new clinical utility of nucleic acid based diagnostic testing. Current commercial technologies produce billions of short read sequences and have shifted focus toward sample preparation and data analysis methods to overcome some of the common error modes with the otherwise high quality data output. Some examples of common error modes include: polynucleotide stretches; mapping of repeat elements; complex variation; mosaicism; coverage bias; and secondary structure artifacts.

Current methods for library preparation start with fragmentation of DNA. This is achieved through chemical, enzymatic or physical fragmentation. A relative large amount of starting material is required to produce enough random fragments of the appropriate size for NGS sequencers (200-500 bp on average). The fragments need to be end-repaired and cleaned up to remove the enzymes used in the fragmentation and/or end repair. Both fragmentation and end repair have sequence specific biases and require very precise attention to protocols to achieve consistent results. After these repaired molecules are purified, adapters are added to the ends through a process called ligation. An additional step is often required to add single base A-tails or overhangs to the ends of the molecules prior to ligation of adapters. Ligase enzymes is extremely expensive and subject to sequence specific biases that result in low coverage of certain regions of the genome. The resulting molecules consist of known adapter sequences flanking unknown sample sequence. This is known as a DNA LIBRARY. The DNA library also needs to be purified to remove enzymes and a precise size selection is required for these molecules. After size selection, the library is again PCR amplified to produce enough material to be diluted on to the sequencer flow cell. So the process for library preparation includes fragmentation, end repair, clean up, A-tailing or overhang generation, ligation of adapters, clean up, amplification, clean up, size selection, PCR, clean up and then addition to a flow cell for sequencing in some aspects.

Described herein is a library preparation incorporating first adapter addition, fragmentation and affinity purification in a single step. This may be achieved using the process of isothermal random priming of template DNA. This process is used for amplifying small amounts of DNA with unknown sequence. Random oligomers is produced at a number of lengths that will work with the genomic context and temperatures relevant for the reaction. In some cases, 8-mer primers are produced with every possible combination of nucleotides. The 3' end of the primer may be random and the 5' end may contain the first adapter sequence. During primer extension, a small amount of biotinylated ddNTPs may be incorporated. The ratio of ddNTP to native dNTP allows precise control over the fragmentation of the library molecules. The biotin incorporation allows the use of streptavidin coated magnetic beads to isolate and purify the copied molecules in a simple, automated step. The second adapter sequence may be added through a second random priming reaction. Using a strand displacing polymerase can allow only the most distal 5' random primer to extend, displacing all other random sequences and remaining hydrogen-bonded to the streptavidin coated magnetic beads. A simple washing step can purify the bound molecules, followed by a low cycle PCR reaction and purification. This protocol requires few processing steps, removes expensive and cumbersome aspects of the library generation workflow and is done at a low cost.

An overview of an embodiment of this protocol is shown in FIG. 1A-1G. An exemplary nucleic acid molecule from an embodied sequence library is shown in FIG. 3A-3D. Comparisons of various embodiments of the methods and compositions described herein are shown in FIG. 2 and FIG. 4A-4D.

With a given read length, e.g., 100 base pairs (bp), an ideal read structure of a genome would have a read covering base 1 to base 100, another covering base 2 to base 101, etc. A library preparation method producing this level of "complexity" with minimized bias is ideal. A "kink" in the template used for sequencing-by-synthesis (SBS) methods from a C-C-C polynucleotide is spread out across the read and the differentiation between a C-C-C and a C-G-C is obtained empirically. The way this artifact represents itself in the data is different when at the beginning of a sequencer read near the solid surface of a flow cell than at the end of a read.

Complex variation that causes disease is by definition different than a healthy genome. A translocation or large insertion may be missed by reference based mapping and assembly. The problem is even harder to resolve when using targeted sequencing methods that reduce the amount of sequencing required, or specify the known disease causing loci for sequencing. Targeted sequencing with most PCR based methods requires the disease-causing mutation to be known in order to capture it in the test.

Described herein are sample preparation methods and analysis for applications of whole genome sequencing, RNA or cDNA sequencing, targeted sequencing and long read sequencing for phasing and/or de novo assembly.

In some embodiments, the preparation of a library is performed as detailed in FIG. 1A-1G. As seen in step 1 (FIG. 1A), a target nucleic acid sequence comprising genomic DNA is bound by multiple random oligonucleotide ("Random 8-mer") primers containing 5' sequencing adapter tails ("A-adapters"). A pool of nucleotides containing a ratio of deoxy NTPs (dNTPs) to biotinylated-dideoxy NTPs (ddNTPs), reaction buffer, and nuclease-free water is added to this mixture. A DNA polymerase having strand displacement activity and ddNTP/biotin incorporation ability is added and extension progresses from the 3' OH of the random oligonucleotides until a biotinylated-ddNTP ("Biotin ddNTP") in incorporated, at which point extension terminates, as shown in step 2 (FIG. 1B). Streptavidin-coated magnetic beads are then added to isolate the tagged first strand extension product. A second set of random oligonucleotide ("Random 8-mer") primers containing 5' sequencing adapter tails ("B adapters") is combined with the isolated first strand extension product, a pool of dNTPs, reaction buffer, and a DNA polymerase having strand displacement activity. A complementary second strand is generated forming a double-stranded molecule as shown in step 3 (FIG. 1C). The double-stranded product is washed and the displaced product is removed as shown in step 4 (FIG. 1D and FIG. 1E). In some cases, the biotin tag is removed at this step. Full-length adapter sequences are added via PCR amplification as shown in step 5 (FIG. 1F), and the resulting molecule in FIG. 1G is suitable for sequencing via any of the sequencing methods described herein.

Figure 2:
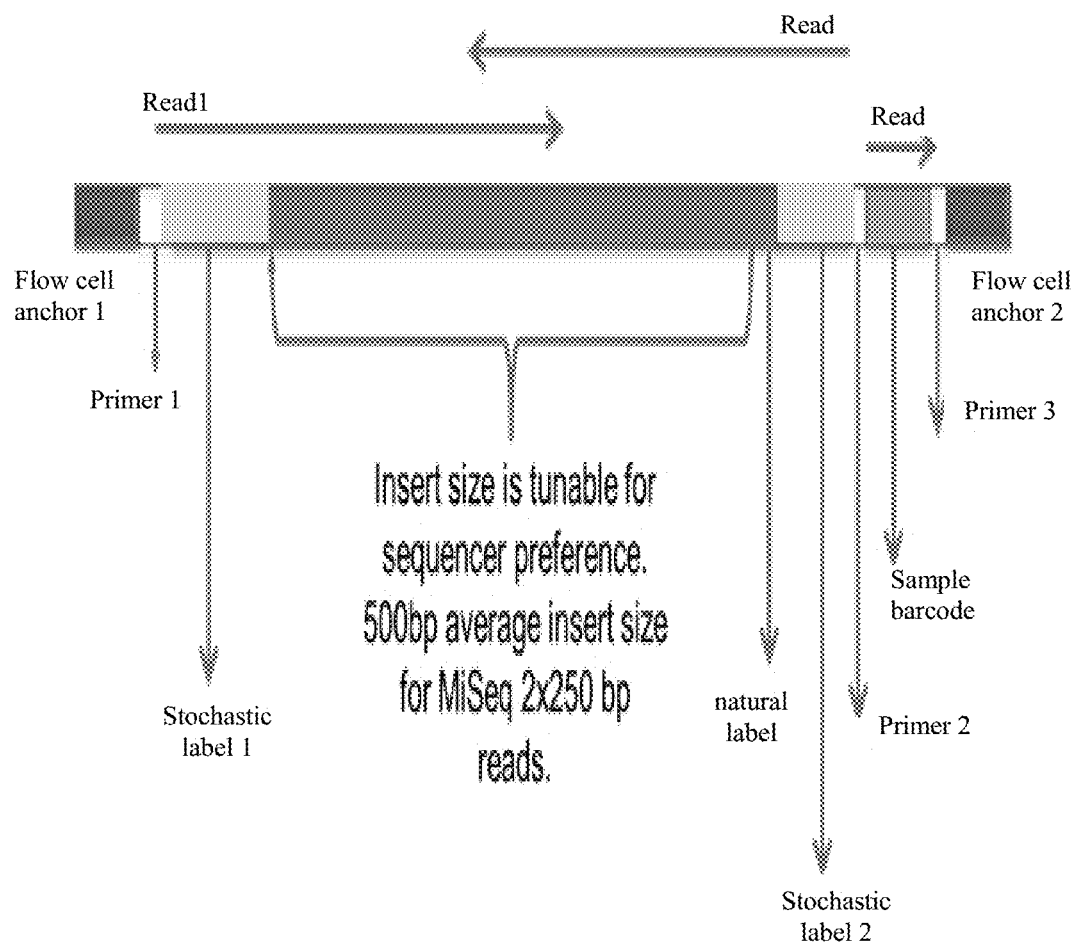
FIG. 2 depicts a representation of the library structure of a tagged nucleic acid molecule comprising a subset of sequence from a target nucleic acid sample.
Figure 3A:
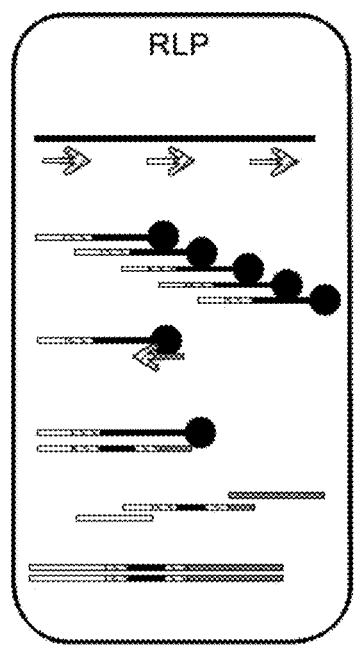
FIG. 3A-D illustrate a general overview of library preparation using a variety of methods.
Figure 3B:
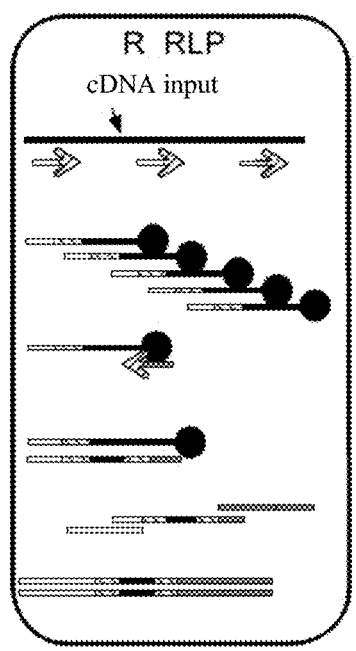
Figure 3C:
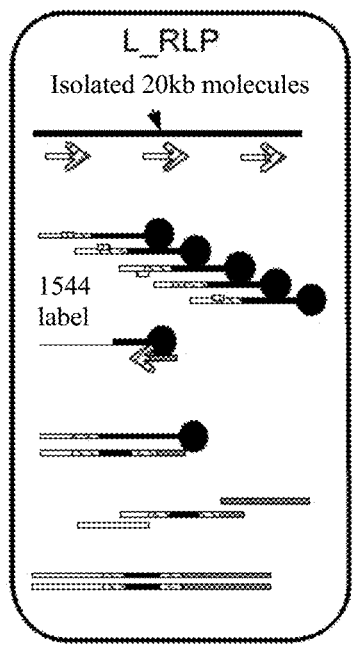
Figure 3D:
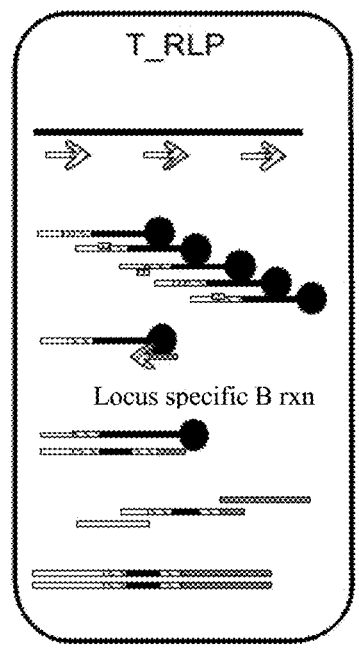

FIG. 2 depicts a representation of an exemplary molecule obtained via the methods described herein. As shown in FIG. 2, an exemplary molecule contains (from left to right), a flow cell anchor 1, binding site for a first primer 1, a stochastic label 1, an insert sequence tunable for sequencer preference, a natural label, a stochastic label 2, a binding site for a second primer 2, a sample barcode, a binding site for a third primer 3, and a flow cell anchor 2. The stochastic labels correspond to the random oligonucleotides (such as 8 mers) described herein. The natural label corresponds to a different ending position on a duplicate read and represents an independent sampling of the template molecule. Alternately, the natural label may be conceived of as the distance from the first tag to the second tag in a given molecule. This distance 'labels' the molecule as unique because it will differ in some embodiments even among molecules have identical first and second labels as an indication of the molecules resulting from independent synthesis events.

FIG. 3 illustrate various embodiments of the methods and compositions described herein. FIG. 3A, the far left panel ("RLP"), depicts the preparation of a library similar to that depicted in FIG. 1A-1G. FIG. 3B, the middle left panel ("R_RLP"), depicts the preparation of a library starting from a target nucleic acid sequence comprising cDNA. FIG. 3C, the middle right panel ("L_RLP"), depicts the preparation of a library starting from a target nucleic acid sequence comprising isolated 20 kb molecules with the addition of 1544 labels onto the tagged first strand extension product. FIG. 3D, the far right panel ("T_RLP"), depicts the preparation of a library similar to that depicted in FIG. 1A-1G, but with inclusion of a B adapter sequence 5' to a locus-specific sequence. A double-stranded intermediate comprising a first strand extension product ending in a ddNTP incorporating a tag (biotin is depicted, but as disclosed herein alternate tags are also contemplated), to which a second strand synthesis oligo is annealed, and from which a second strand of the intermediate is synthesized.

Figure 4A:
FIG. 4A-4D depict a comparison of the library structure of a tagged nucleic acid molecule from a variety of libraries.
Figure 4B:
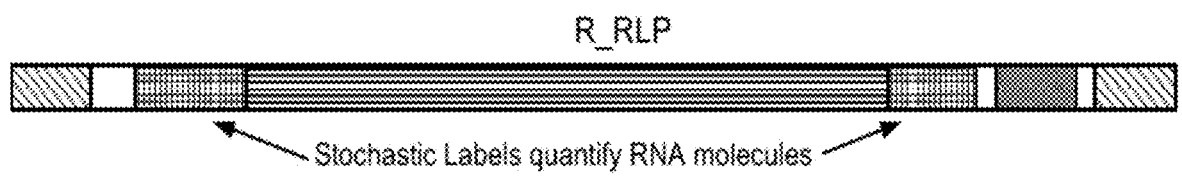
Figure 4C:
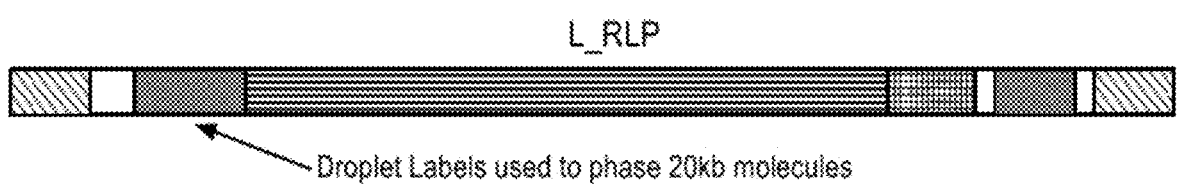
Figure 4D:
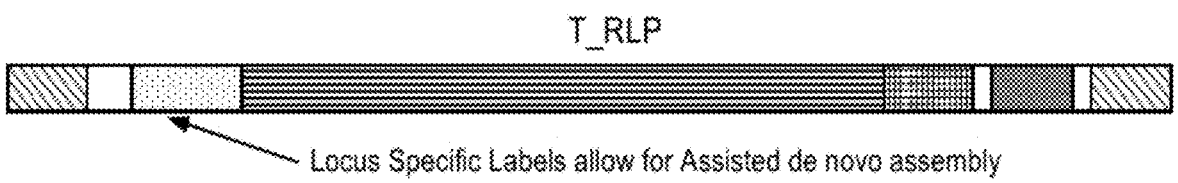

FIG. 4A-4D depict a representation of exemplary molecules obtained via the methods described in FIG. 3A-3D. As shown in FIG. 4A-4D, the molecules include (from top to bottom), FIG. 4A shows an "RLP" molecule similar to that depicted in FIG. 2; FIG. 4B shows an "R_RLP" molecule such as could be obtained from a target nucleic acid sequence comprising cDNA and containing stochastic labels which allow quantification of RNA molecules; FIG. 4C shows an "L_RLP" molecule such as could be obtained from target nucleic acid sequence comprising isolated 20 kb molecules and containing 'droplet labels' which allow phasing of 20 kb molecules; and FIG. 4D shows a "T_RLP" molecule such as could be obtained from the inclusion of a B adapter sequence 5' to a locus-specific sequence and containing locus-specific labels allowing for assisted de novo assembly.

Figure 5A:
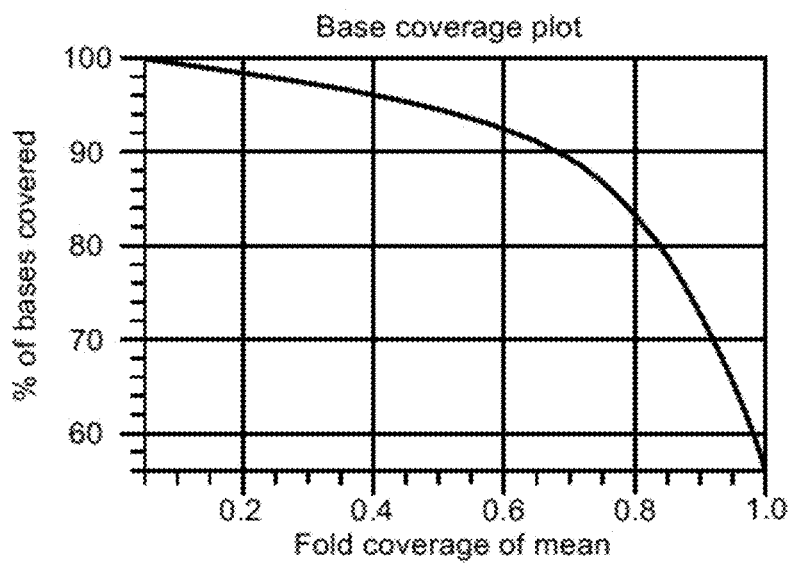
FIG. 5A-B illustrate a comparison of the uniformity and guanine-cytosine (GC) bias for two libraries.
Figure 5B:
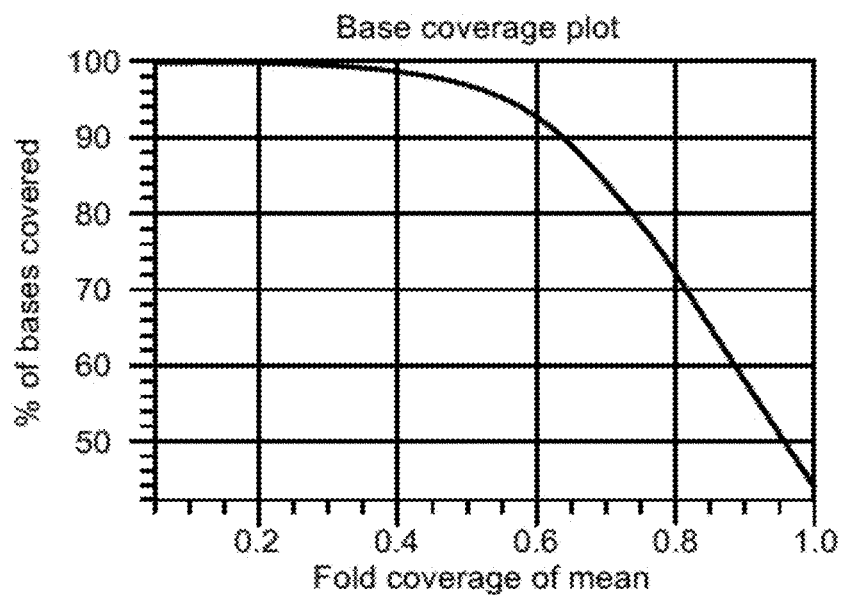

FIG. 5A-5B depict normalized coverage plots with the percent of the genome covered ("% of bases covered") plotted against the fraction of the mean ("Fold coverage of mean") where 1 equals the mean for a NEXTERA library (left side) in FIG. 5A and a library obtained via the methods described herein ("Rapid Library Prep," right side) in FIG. 5B. The slope of the curve and the area under curve in the upper left and upper right graphs indicate that the rapid library prep library outperforms a comparable library, particularly at lower fold coverage of the mean, in terms of base coverage.

Figure 6A:
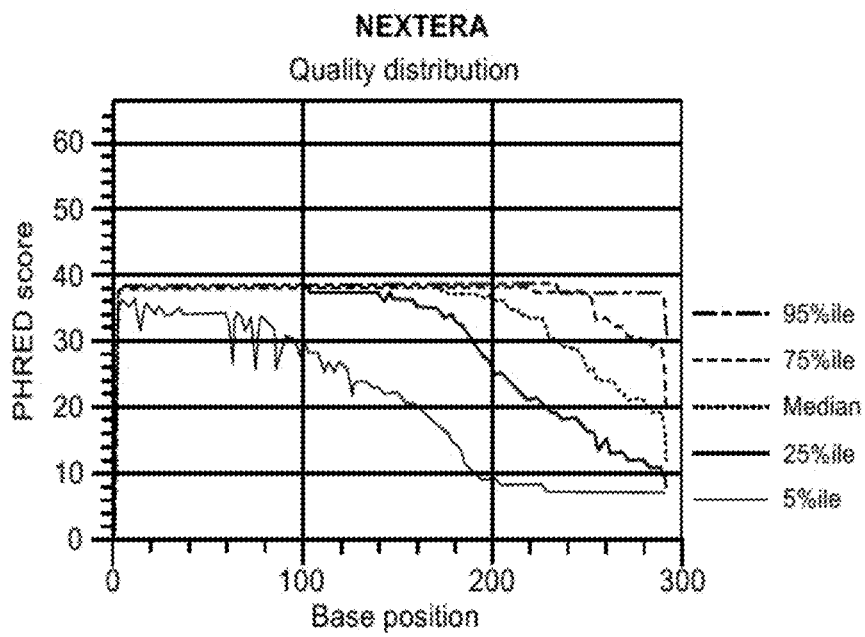
FIG. 6A-6B illustrate a comparison of the sequence quality for two libraries.
Figure 6B:
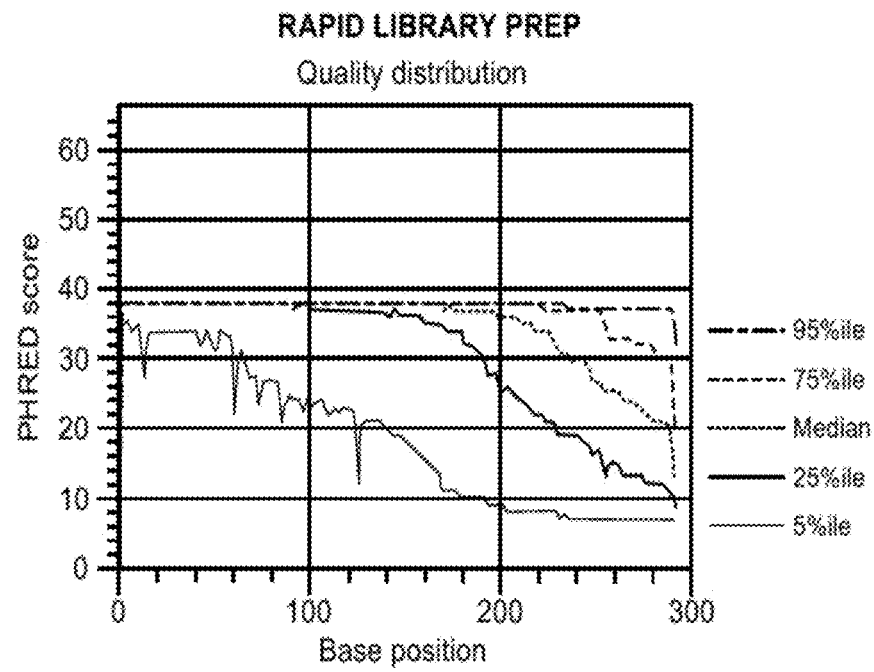

FIG. 6A-5B compare the sequence quality for a NEXTERA library (left side) in FIG. 6A and a library obtained via the methods described herein ("Rapid Library Prep," right side) in FIG. 6B. As is seen in FIG. 6A-6B, the methods produce libraries of comparable quality as indicated by this assay.

FIG. 7A-7B compare the guanine-cytosine (GC) content for a NEXTERA library (left side) in FIG. 7A and a library obtained via the methods described herein ("Rapid Library Prep," right side) in FIG. 7B. As is seen in FIG. 7A-7B, the methods described herein obtain more sequences with lower %-GC content than a comparable library when sequencing an *Escherichia coli* genome with a %-GC content of about 50%.

Figure 8A:
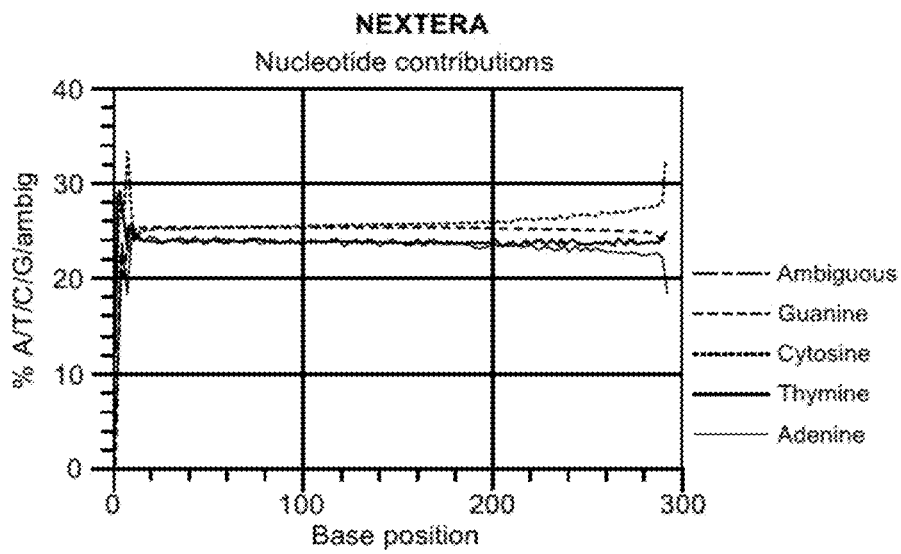
FIG. 8A-8B illustrate a comparison of the nucleotide contribution for two libraries.
Figure 8B:
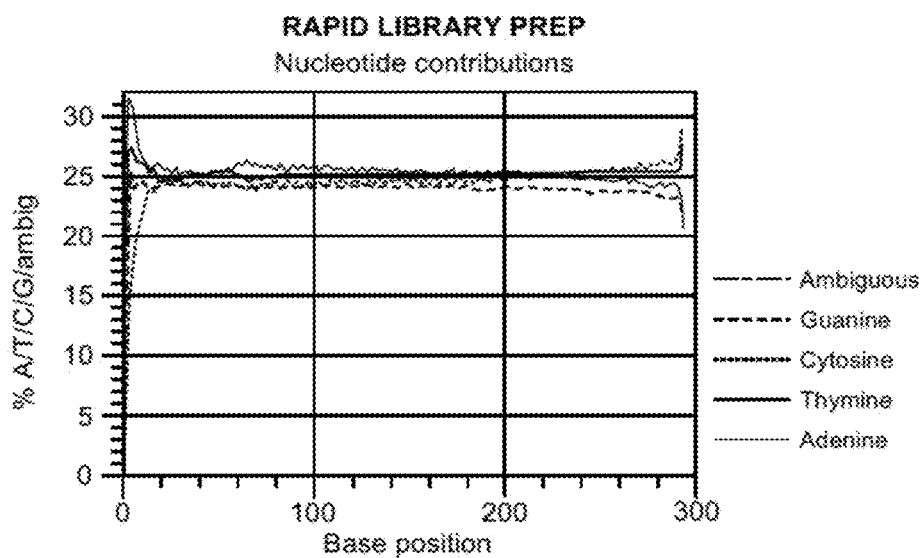

FIG. 8A-8B compare the nucleotide contribution for a NEXTERA library (left side) in FIG. 8A and a library obtained via the methods described herein ("Rapid Library Prep," right side) in FIG. 8B. As is seen in FIG. 8A-8B, the nucleotide contributions plots indicate a bias at later base positions in the incorporation of nucleotides using comparable methods. Said bias is not present in the library prepared as disclosed herein.

Figure 9A:
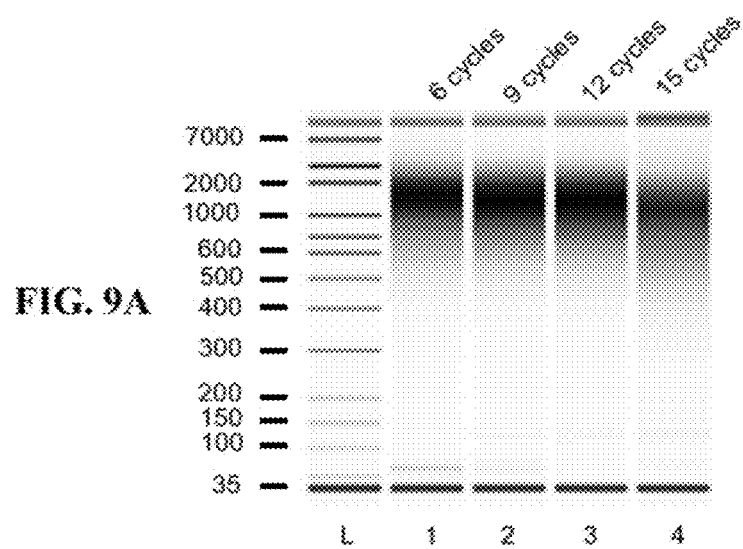
FIG. 9A-9E illustrate the effect of cycle number using 50 ng of human genomic DNA (gDNA).
Figure 9B:
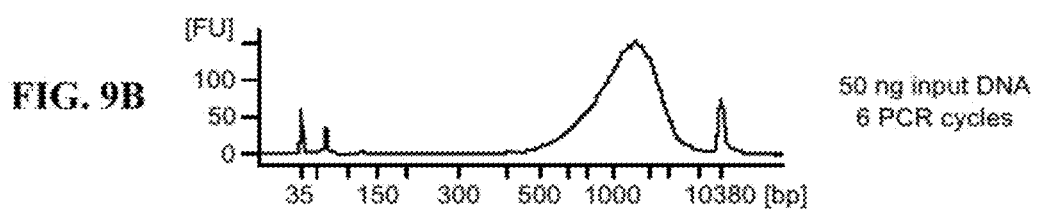
Figure 9C:
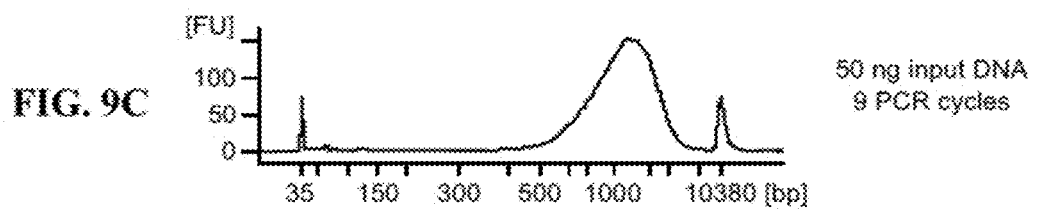
Figure 9D:
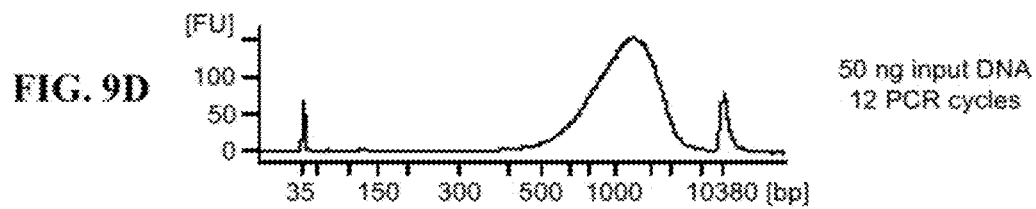
Figure 9E:
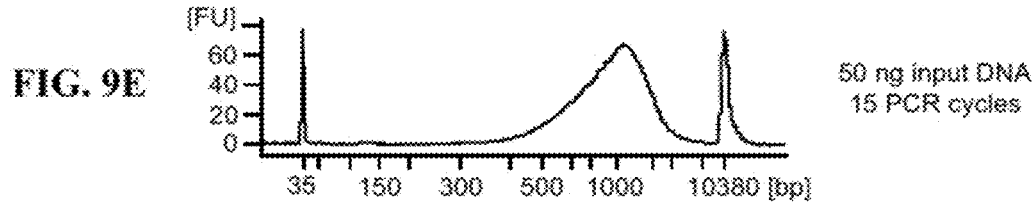

FIG. 9A-9E illustrate the effect of cycle number using 50 ng of human genomic DNA. As is seen in FIG. 9B, amplification performed on a library produced as disclosed herein through only six cycles produces a measurable amount of high quality amplification product (right side) comparable to that produced through doubling the number of cycles to 12 (FIG. 9D). When the number of PCR cycles is increased to 15, the abundance of small fragments increases (left side) in FIG. 9A.

Figure 10A:
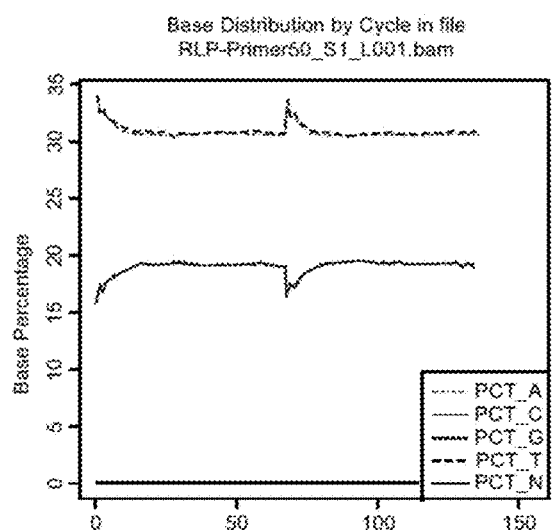
FIG. 10A-10C illustrate the quality of amplification for 250 cells of a human cell line.
Figure 10B:
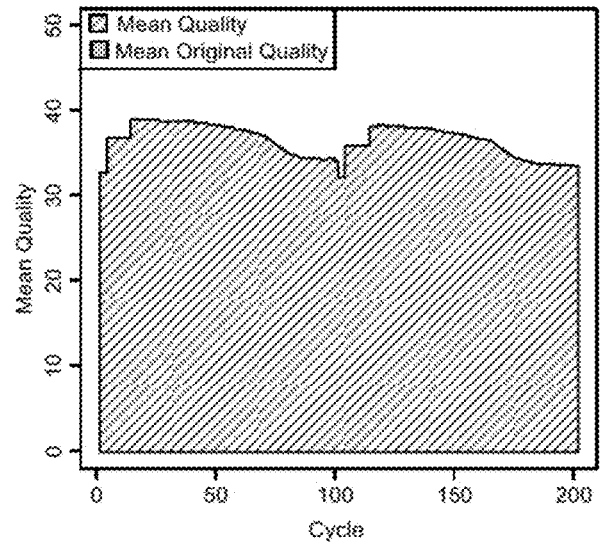
Figure 10C:
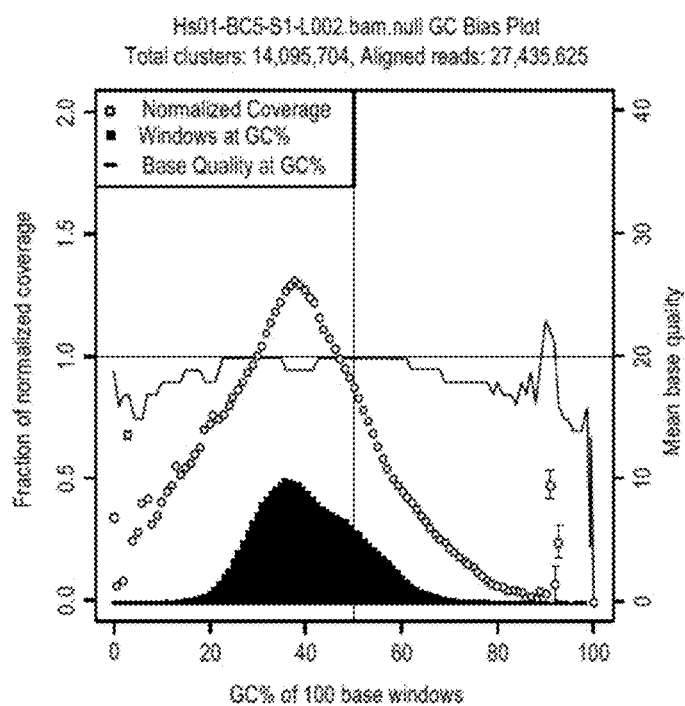

FIG. 10A-10C illustrate the base distribution (left panel, FIG. 10A) quality by cycle (middle panel, FIG. 10B), and GC bias (right panel, FIG. 10C) for 250 cells of a human cell line. As shown in FIG. 10A, the base distribution of PCT-A superimposes with the base distribution of PCT-T, whereas as the base distribution of PCT-C superimposes with the base distribution of PCT-G. As is seen in FIG. 10A-10C, Mean quality is uniformly high throughout the cycles, the fraction or normalized coverage is consistently above the GC fraction at all GC fractions listed, and the base quality is high independent of GC %.

Figure 11:
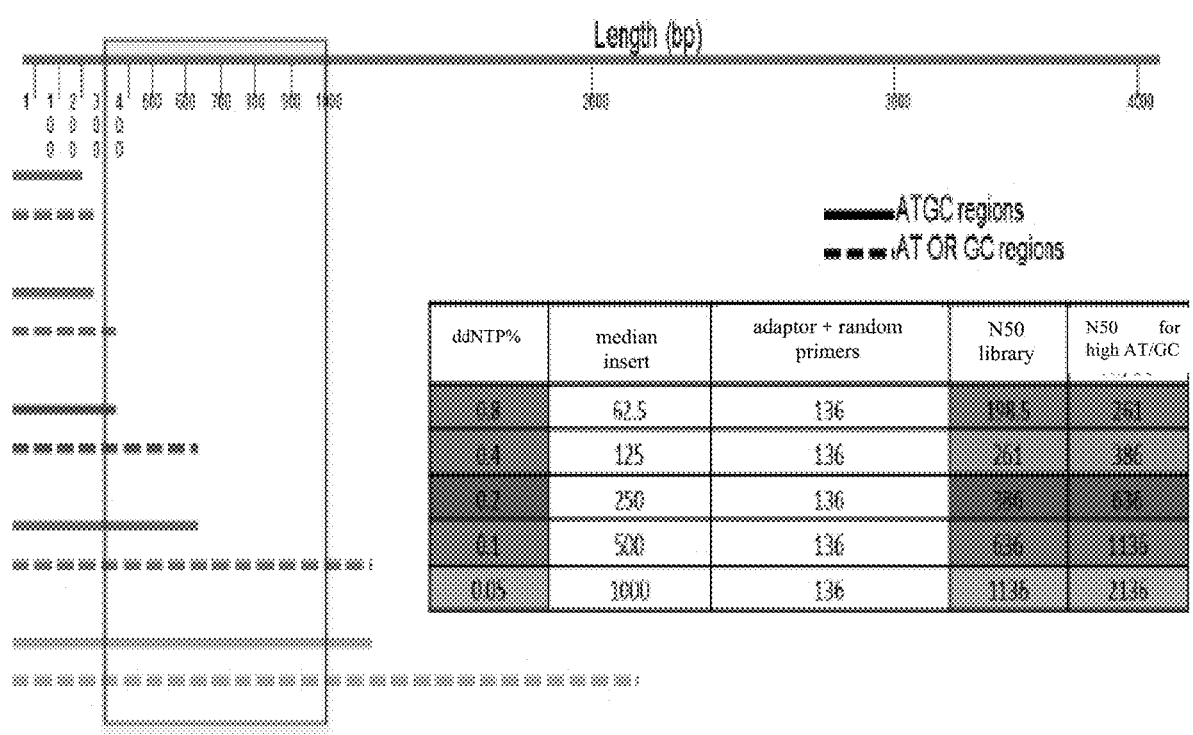
FIG. 11 illustrates the effect of ddNTP concentration on fragment length and AT bias.

FIG. 11 illustrates the effect of ddNTP concentration on fragment length and AT bias. As is seen in FIG. 11, decreasing ddNTP concentration results in a higher N50 fragment length, and as indicated by the final column of the table, as AT/GC ratio increases, the N50 value increases independent of ddNTP concentration. Line pairs (solid and dashed) across the bottom of FIG. 11 represent N50 fragment lengths for ddNTP concentrations of 0.8%, 0.4%, 0.2%, 0.1%, and 0.05%. The box drawn around base lengths from about 350 bases to 1000 bases represents an optimal fragment length of some embodiments. As demonstrated by FIG. 11, library insert (that is, target sequence) size is optimized by varying the ddNTP %, allowing selection of library constituents of a specific size, as indicated by the box spanning fragments of sizes 350 bp to 1000 bp.

Figure 12A:
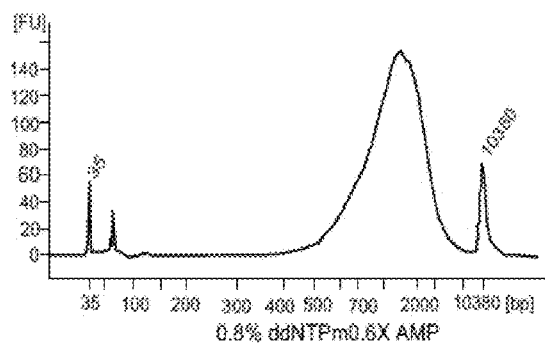
FIG. 12A-12F illustrate the effect of ddNTP concentration on yield.
Figure 12D:
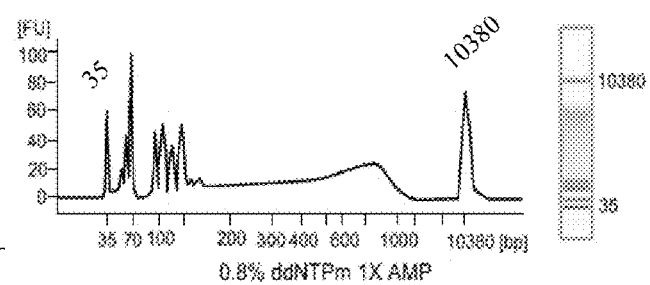
Figure 12B:
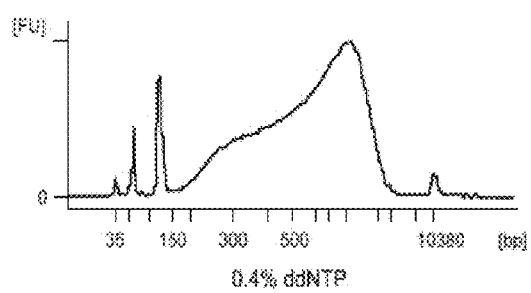
Figure 12E:
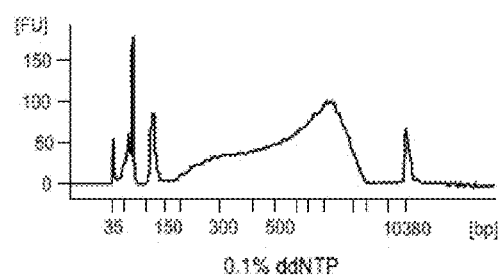
Figure 12C:
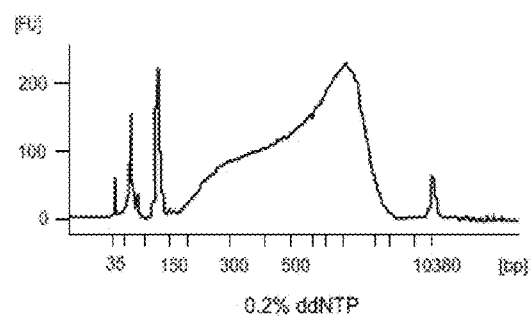
Figure 12F:
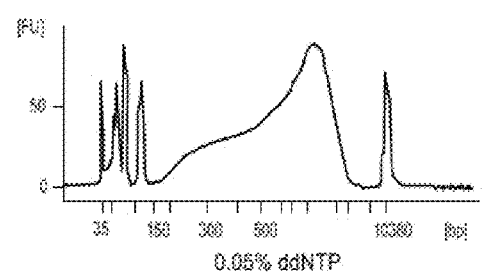

FIG. 12A-12F illustrate the effect of ddNTP concentration on yield. FIG. 12A-12F illustrate the product sizes in the form of peaks. In FIG. 12A and FIG. 12D, the far left peak represents a product of 35 bp, whereas the far right peak represents a product of 10380 bp. This is also reflected in the legend on the right of FIG. 12D, wherein the line on the top represents a product of 10380 bp and the line on the bottom represents a product of 35 bp. The shear between the top and the bottom lines corresponds to product sizes between 35 bp to 10380 bp.

Figure 13:
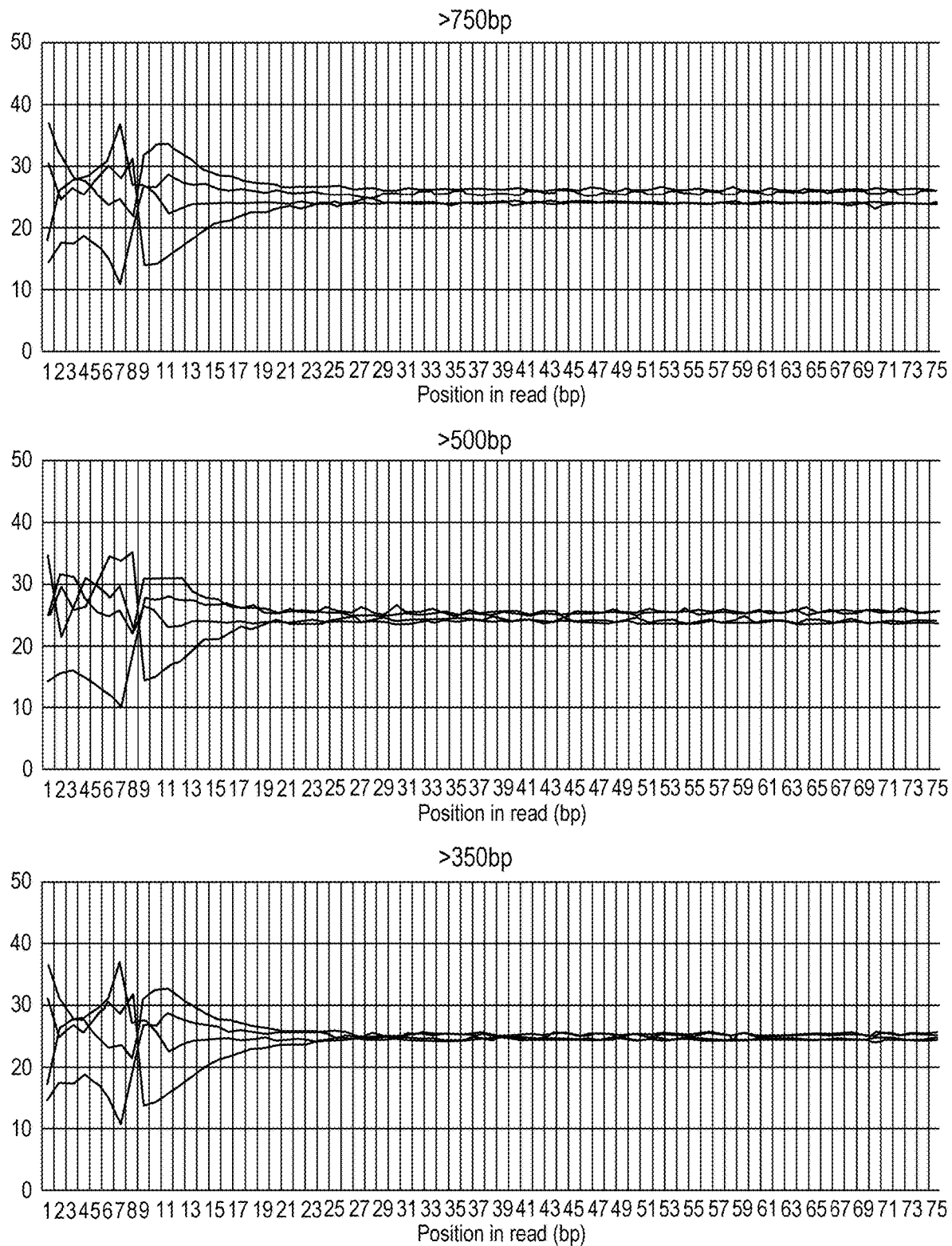
FIG. 13 illustrates the read position for molecules selected by size (>750 bp-top panel; >500 bp-middle panel; >350 bp-bottom panel).

FIG. 13 illustrates that across the read position for molecules selected by size (>750 bp-top panel; >500 bp-middle panel; >350 bp-bottom panel), reads do not demonstrate a substantial bias for any particular base or base pair combination. As read insert length increases, bias increases.

Figure 14A:
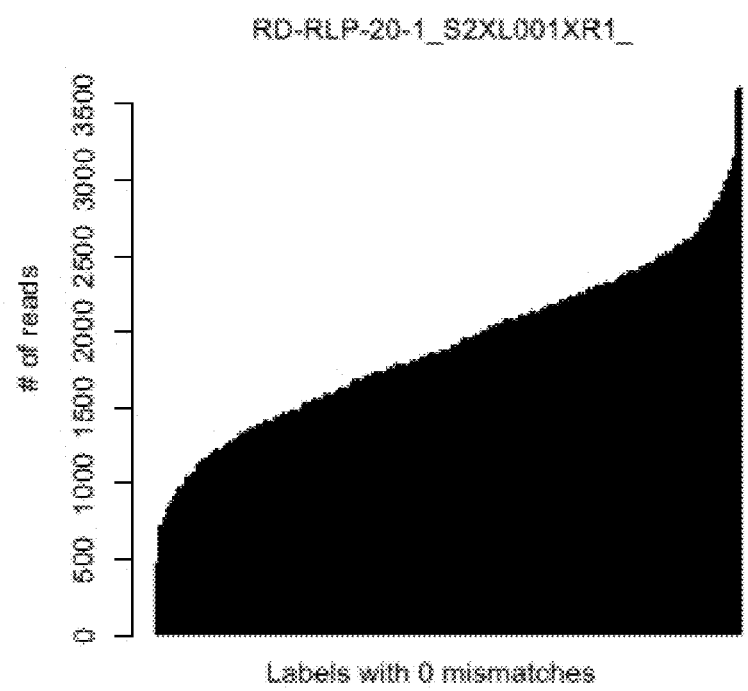
FIG. 14A-14B depict counts of reads matching a given label with zero and one mismatches allowed for 250 cells and 20 kb molecules.
Figure 14B:
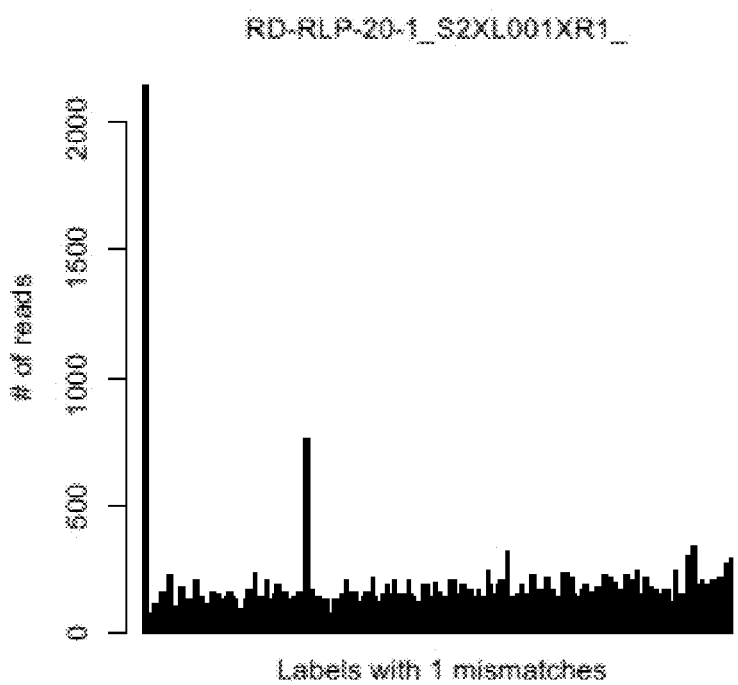

FIG. 14A-14B depict counts of read matching a given label with zero (FIG. 14A) and one mismatches (FIG. 14B) allowed for 250 cells and 20 kb molecules. As is seen in FIG. 14A-14B, the vast majority of reads do not demonstrate a mismatch.

Figure 15A:
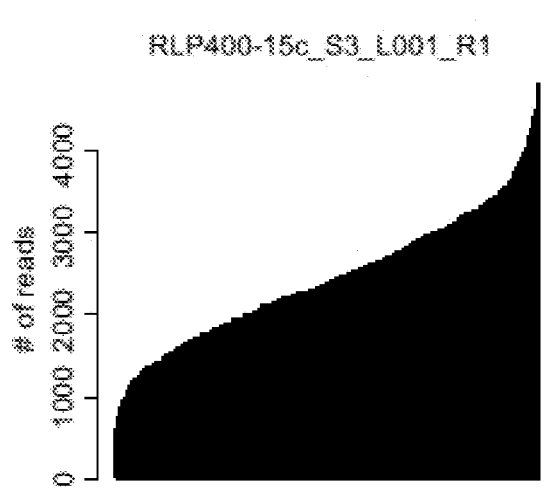
FIG. 15A-15C depict counts of reads matching a given label with zero, one, and two mismatches allowed for 400 pg of input.
Figure 15B:
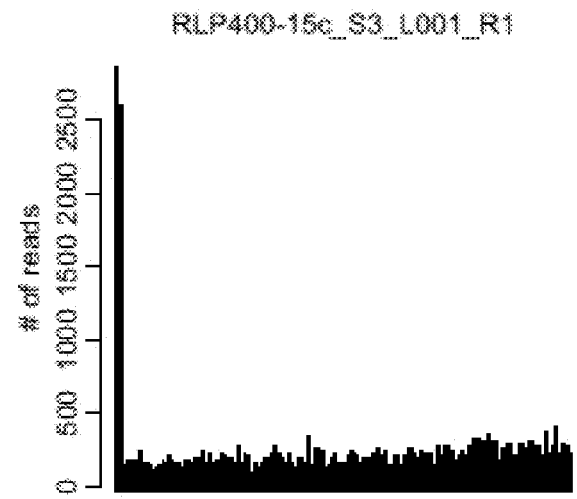
Figure 15C:
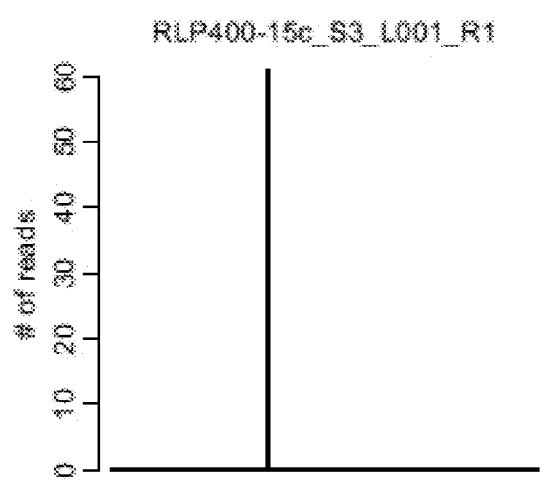

FIG. 15A-15C depict counts of read matching a given label with zero (FIG. 15A), one (FIG. 15B), and two mismatches (FIG. 15C) allowed for 400 pg of input. As is seen in FIG. 15A-15C, the vast majority of reads do not demonstrate a mismatch.

Figure 16A:
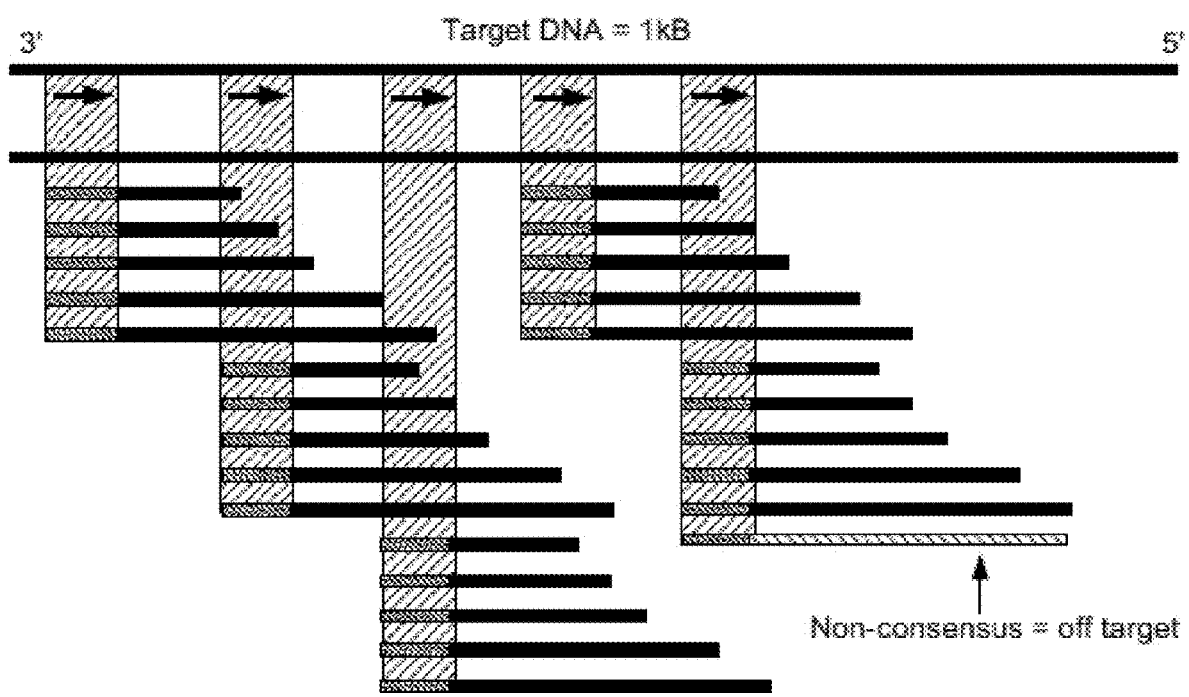
FIG. 16A-16B depict targeted sequencing sensitive to complex variants.
Figure 16B:
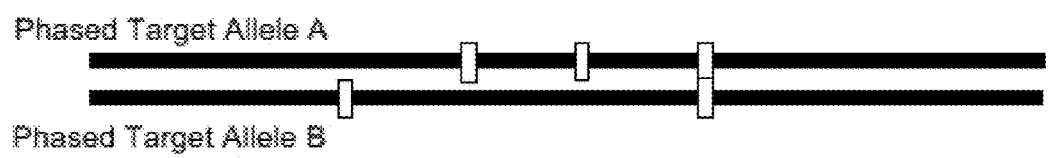

FIG. 16A-16B depict target sequencing sensitive to complex variants such that variant phase is mapped. As is seen in FIG. 16A-16B, the methods and compositions described herein allow for identification of whether variants of polymorphisms map to a single physical molecule (i.e., are "in phase").

Figure 17A:
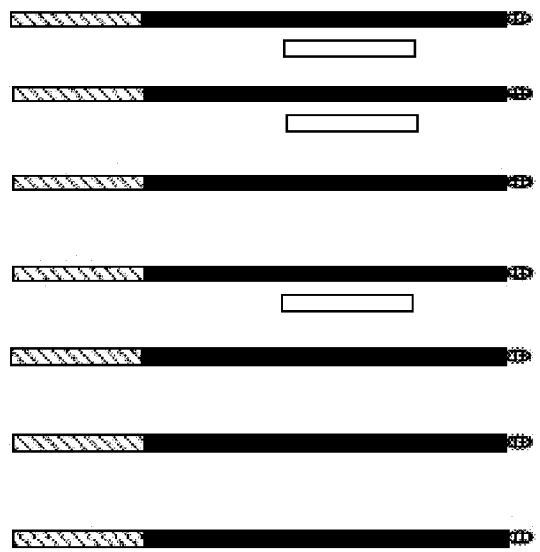
FIG. 17A-17C depict a reverse priming PCR approach.
Figure 17B:
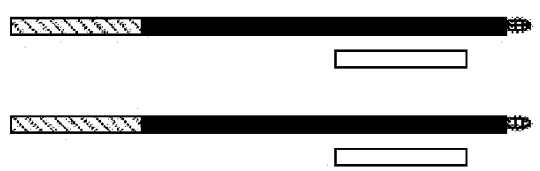
Figure 17C:
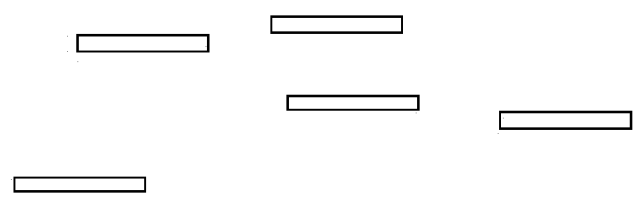

FIG. 17 depict a reverse priming PCR approach. Library synthesis results in a molar excess of template, such that fewer cycles, and a lower concentration of primers, are required to generate a sufficient amount of template for downstream applications. First strand templates are indicated by a two-shade schematic having a circular tag (FIG. 17A and FIG. 17B). As seen in the right side (FIG. 17B and FIG. 17C), the primers in molar excess of template will potentially bind at non-specific sites or to each other.

Figure 18A:
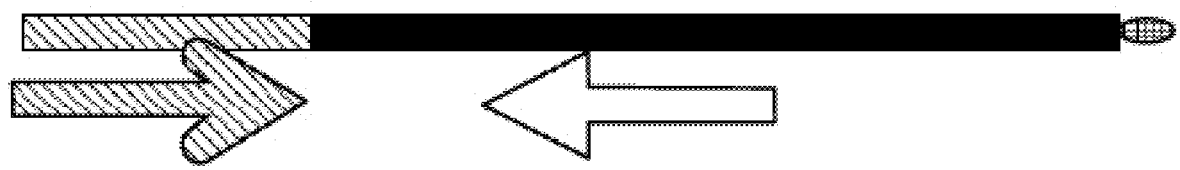
FIGS. 18A-18B depict a hemispecific PCR reaction, primers and product.
Figure 18B:
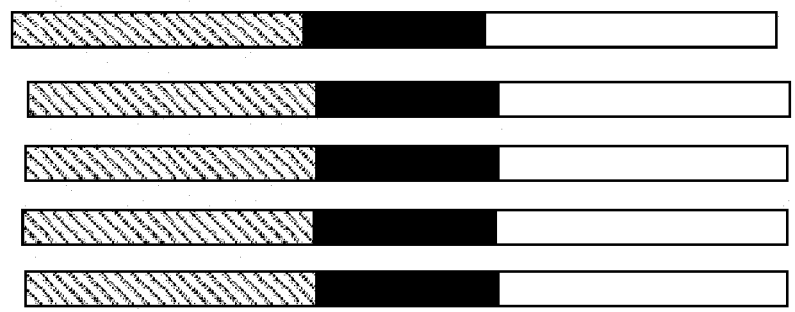

FIG. 18A-18B depict hemispecific PCR, or targeted, second-strand sequence generation. A first strand (FIG. 18A), top, is synthesized using a nonspecific primer extended through to termination upon incorporation of a ddNTP, indicated by the oval at right. The nonspecific primer (pointing rightwards in the figure) is added in combination with a primer that binds specifically to a region of interest (pointing leftwards in the figure). Thermocycling is performed, to result in amplicons as depicted at bottom (FIG. 18B), comprising sequence adjacent to the specific primer added to the reaction. Described another way, the first strand synthesis reaction consists of an adapter-tailed random primer. That primer binds, extends, terminates, and is captured by magnetic beads. Then a locus-specific primer in the second strand synthesis reaction creates a second strand copying the first strand synthesis product all the way through the universal A-adapter sequence. That universal sequence is then used along with the locus-specific sequence to amplify via PCR.

FIG. 19 depicts an exemplary cancer risk panel. A targeted library oligo set may amplify members of the exemplary set.

Figure 20:
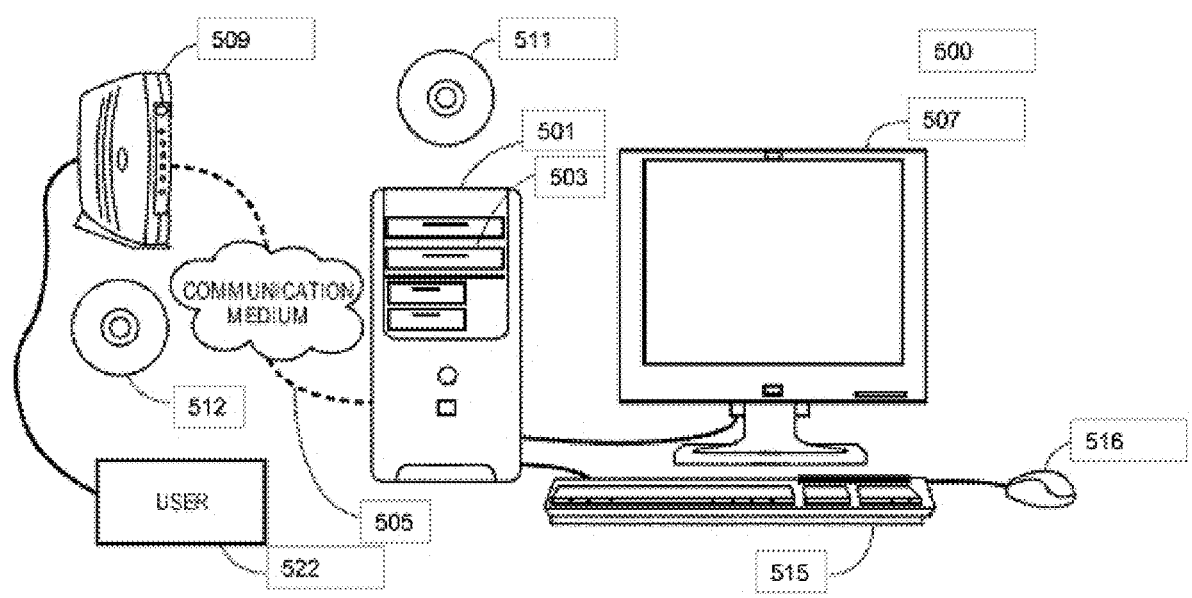
FIG. 20 illustrates various components of an exemplary computer system according to various embodiments of the present disclosure.

The computer system 500 illustrated in FIG. 20 may be understood as a logical apparatus that can read instructions from media 511 and/or a network port 505, which can optionally be connected to server 509 having fixed media 512. The system, such as shown in FIG. 20 can include a CPU 501, disk drives 503, optional input devices such as keyboard 515 and/or mouse 516 and optional monitor 507. Data communication is achieved through the indicated communication medium to a server at a local or a remote location. The communication medium can include any means of transmitting and/or receiving data. For example, the communication medium is a network connection, a wireless connection or an internet connection. Such a connection can provide for communication over the World Wide Web. It is envisioned that data relating to the present disclosure is transmitted over such networks or connections for reception and/or review by a party 522 as illustrated in FIG. 20.

Figure 21:
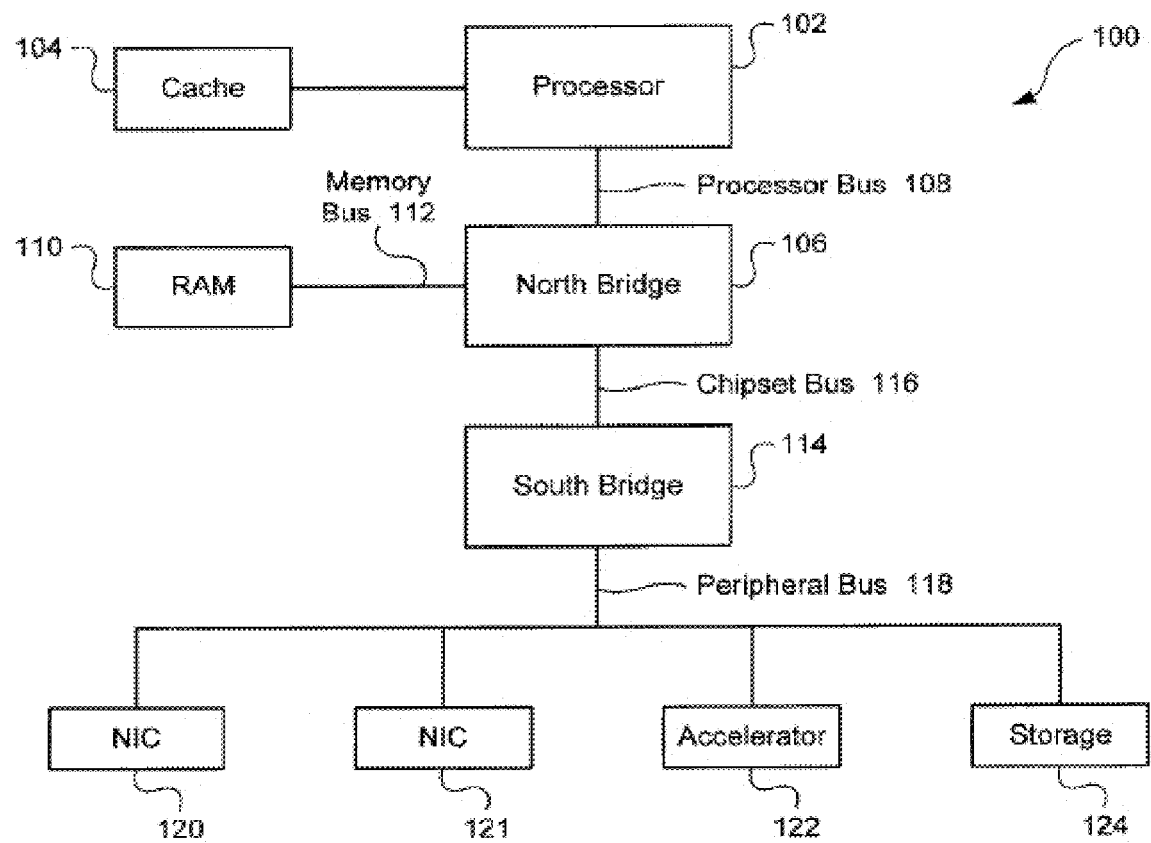
FIG. 21 is a block diagram illustrating the architecture of an exemplary computer system that is used in connection with various embodiments of the present disclosure.

FIG. 21 is a block diagram illustrating a first example architecture of a computer system 100 that is used in connection with example embodiments of the present disclosure. As depicted in FIG. 21, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution is used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 21, a high speed cache 104 is connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus is, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge is incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator is used for adaptive data restructuring or to evaluate algebraic expressions used in extended set processing.

Software and data are stored in external storage 124 and is loaded into RAM 110 and/or cache 104 for use by the processor. The system 100 includes an operating system for managing system resources; non-limiting examples of operating systems include: Linux, Windows™, MacOS™, BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that is used for distributed parallel processing.

Figure 22:
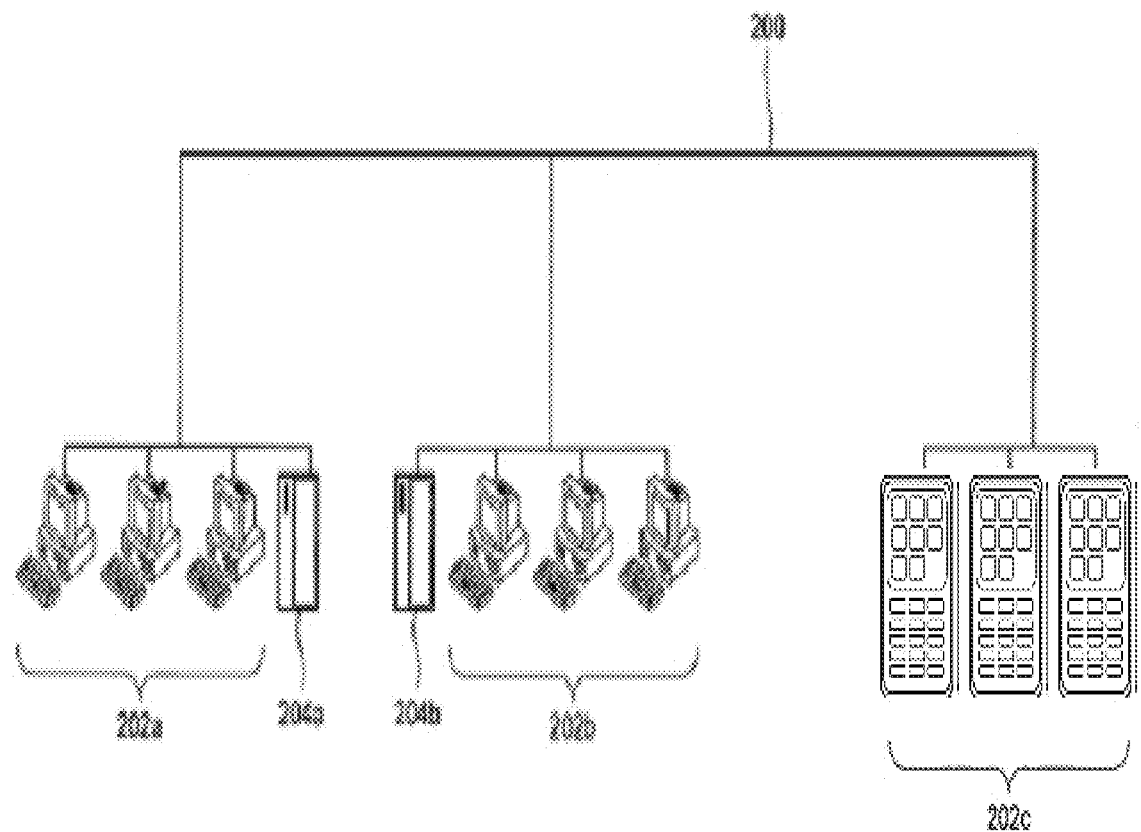
FIG. 22 is a diagram illustrating an exemplary computer network that is used in connection with various embodiments of the present disclosure.

FIG. 22 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model is used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 22 illustrates an example only, and a wide variety of other computer architectures and systems is used in conjunction with the various embodiments of the present disclosure. For example, a blade server is used to provide parallel processing. Processor blades is connected through a back plane to provide parallel processing. Storage can also be connected to the back plane or as Network Attached Storage (NAS) through a separate network interface.

In some examples, processors can maintain separate memory spaces and transmit data through network interfaces, back plane or other connectors for parallel processing by other processors. In some embodiments, some or all of the processors can use a shared virtual address memory space.

Figure 23:
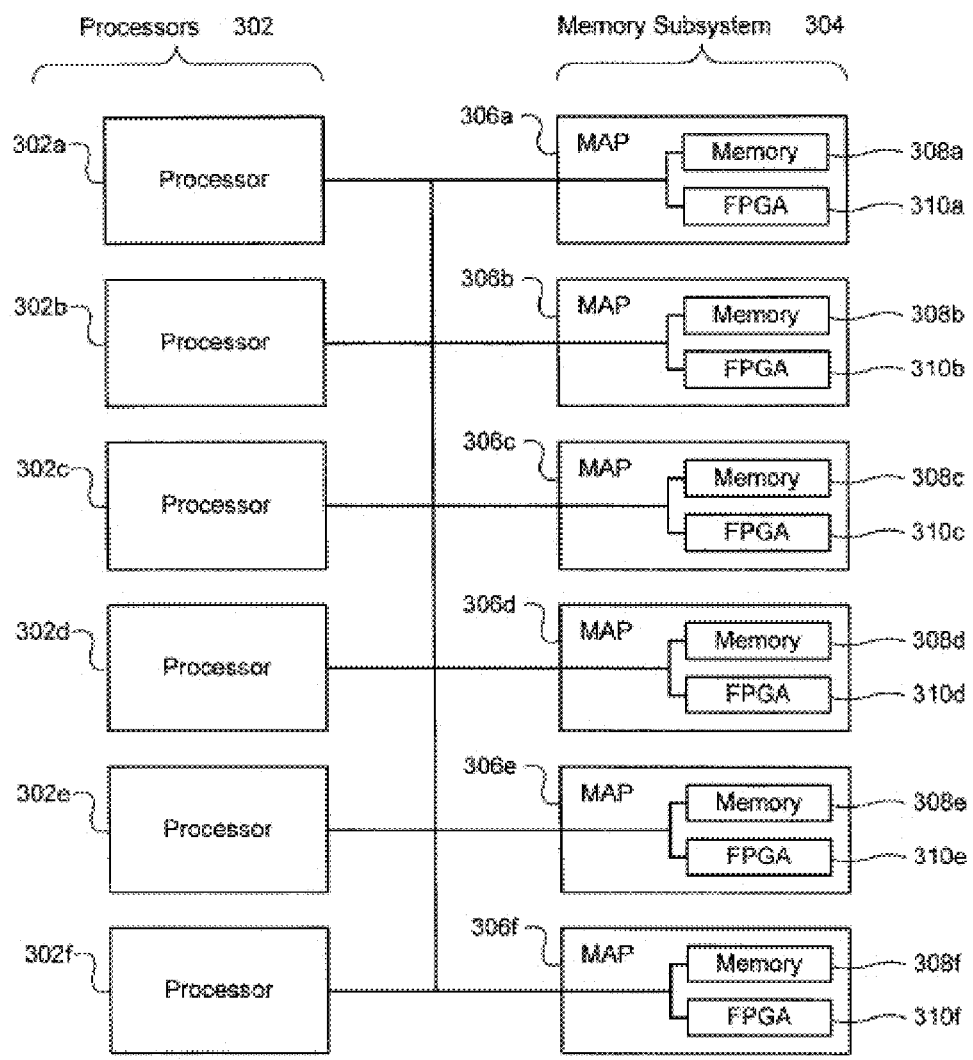
FIG. 23 is a block diagram illustrating the architecture of another exemplary computer system that is used in connection with various embodiments of the present disclosure.

FIG. 23 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms is provided to the FPGAs 310a-f for processing in close coordination with a respective processor. For example, the MAPs is used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems is used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system is implemented in software or hardware. Any variety of data storage media is used in connection with example embodiments, including random access memory, hard drives, flash memory, tape drives, disk arrays, Network Attached Storage (NAS) and other local or distributed data storage devices and systems.

In some cases, the computer system is implemented using software modules executing on any of the above or other computer architectures and systems. In some embodiments, the functions of the system is implemented partially or completely in firmware, programmable logic devices such as field programmable gate arrays (FPGAs) as referenced in FIG. 23, system on chips (SOCs), application specific integrated circuits (ASICs), or other processing and logic elements. For example, the Set Processor and Optimizer is implemented with hardware acceleration through the use of a hardware accelerator card, such as accelerator card 122 illustrated in FIG. 21. In some cases, data sets corresponding to sequence of at least one molecule or at least one molecular data set or at least one sequence library comprising 10, 100, 1000, 10,000, 100,000, 1,000,000, 10,000,000, or more than 10,000,000 molecular sequences are stored and assessed on a computer system as disclosed herein. In some cases a method of generating a computer-stored data set comprising at least 1000 non-identical, tagged nucleic acid molecule sequences each comprising a subset of sequence from a nucleic acid sample is practiced on a computer system as disclosed herein. In some cases the method comprises: storing on a computer a first nucleic acid molecule sequence comprising a first 5' molecular tag sequence, a first insertion sequence having a first length from said nucleic acid sample, and a first 3' molecular tag sequence; storing on a computer a second nucleic acid molecule sequence comprising a second 5' molecular tag sequence, a second insertion sequence having a second length, and a second 3' molecular tag sequence; and excluding from said data set said second double-stranded nucleic acid molecule sequence if: said first 5' molecular tag sequence is identical to said second 5' molecular tag sequence; said first 3' molecular tag sequence is identical to said second 3' molecular tag sequence; said second insertion sequence is identical to said first insertion sequence; and said second target sequence length is identical to said first target sequence length and differs by not more than five bases.

Rapid Nucleic Acid Library Prep

Generating Next Generation Sequencing (NGS) libraries from every possible position in a genome requires an unbiased approach to converting genomic DNA (gDNA) template into the appropriate size library molecule with the platform specific sequencing adapters flanking the gDNA. This may be performed using a random primer with a sequencing adapter tail, as illustrated by the following schematic: 5'-adapter sequence-NNNNNNNN-3'.

To minimize bias for a given genome, the "random" portion of the primer may be synthesized in a semi-random fashion to account for variable content in the genome of interest. A given genome (e.g., the human genome) is broken up into 100 bp windows of varying GC content. Ideally, primers would be synthesized to include representative "randomness" ordered against the windows of GC content in the genome from 1% to 100% GC and synthesized and pooled in ratios relative to the content of the genome at each GC %.

Random priming can allow for each base of a genome to be represented as the start position for a sequencer read. In order to end each library molecule at every possible base in the genome, a random/unbiased approach to terminate polymerization from a random primer is required. To do this, a cocktail of ddNTPs containing a fixed ratio of each of the four native nucleotides to a fixed ratio of dideoxynucleotides that are devoid of a 3'—OH group may be used. The ratio of ddNTP to dNTP can determine the probability of termination at any given base position. For example, a 1% ddNTP cocktail (99% dNTP) would give a probability that 99% of molecules extending from a random primer will polymerize past the first base. This same example would give a N50 (50% of the molecules will be longer than N bases) of 50 bp. As the relative ddNTP proportion decreases, the N50 insert size increases. Thus, under certain conditions, a ddNTP % of 0.8 leads to a median insert size (N50) of 62.5, and a comparable N50 of full length library molecules including adapters and random primers of 198.5, a ddNTP % of 0.4 leads to a median insert size (N50) of 125 and a comparable N50 of full length library molecules including adapters and random primers of 261, a ddNTP % of 0.2 leads to a median insert size (N50) of 250 and a comparable N50 of full length library molecules including adapters and random primers of 386, a ddNTP % of 0.1 leads to a median insert size of 500 and a comparable N50 of full length library molecules including adapters and random primers of 636, and a ddNTP % of 0.05 leads to a median insert size of 1000 and a comparable N50 of full length library molecules including adapters and random primers of 1136. For regions of low complexity, such as stretches of AT or GC, the effective concentration of ddNTP in that genomic location would be reduced by half, giving an N50 of 100 nucleotides for a primer extension reaction occurring in such low complexity genomic loci with a 1% ddNTP cocktail. (Not accounting for polymerase incorporation efficiency differences amongst all 8 nucleotides).

Adjusting the ddNTP % in the reaction can adjust the range and diversity of the polymerized molecules. The effect of the ddNTP concentration on fragment length and adenine-tyrosine bias is shown in FIG. 11. The effect of ddNTP concentration on yield is shown in FIG. 12A-12F. At 0.4% ddNTP, the molarity from 300-1000 bp (mole) is 27.5; at 0.2% ddNTP, the molarity from 300-1000 bp (mole) is 16.1; at 0.1% ddNTP, the molarity from 300-1000 bp (mole) is 5.8; and at 0.05% ddNTP, the molarity from 300-1000 bp (mole) is 4.9. FIG. 13 shows the read position for molecules selected by size.

An additional step is to isolate the adapter-labeled molecules from the gDNA template and any excess reactants such as primers and excess NTPs. This is done through the use of biotinylated ddNTPs. A streptavidin coated magnetic bead is used to accomplish this isolation.

The choice of polymerase is restricted to an enzyme that has the capabilities of strand displacement as well as ddNTP/biotin incorporation. SEQUENASE and THERMOSEQUENASE (Affymetrix, Santa Clara, Calif.) are two such enzymes. If low input amounts are required due to lack of sample resource or forced dilution, the reaction may be optimized to improve yield through the use of enzyme cocktails such as SEQUENASE and Phi29, a highly processive polymerase devoid of the ability to incorporate ddNTPs. The phi 29 enzyme will increase the template amount for processing by SEQUENASE in the reaction. The yield and diversity of template may also be increased by optimizing the duration of the reaction.

The product of such a sequencing reaction is represented by the following schematic: 5'-ADAPTER-NNNNNNNN-GENOMIC INSERT-ddNTP/biotin.

Current commercial sequencers require the gDNA insert to be flanked by 2 adapter sequences. The second adapter may be added through a second random priming reaction. The isolated product from the magnetic beads is used as template for a second random priming reaction using a random primer with a second adapter, as demonstrated by the schematic: 5'-Adapter2-NNNNNNNN-3'. The displaced product may also be used as template for a second random priming reaction using a random primer with a second adapter.

The enzyme for the second adapter addition may not require the ability to incorporate ddNTP. Strand displacement may be a requirement. Acceptable enzymes include SEQUENASE, THERMOSEQUENASE, Phi29, Bst DNA Polymerase, and Taq DNA polymerase. The random portion of the primer can bind to the bead bound template and extend through the end of the template molecule. The primer that binds closest to the 3' end of the template can displace the primers that are bound downstream so that a single copy of the bead bound template will be produced with both the first and second adapters. This copy can remain hydrogen-bonded to the magnetic beads. Excess primer, NTP, enzyme and displaced product is removed through bead washing. The resulting product is heat denatured (releasing it from the bead) and sequenced or amplified through PCR with primers complementary to the adapters. A product created thereby is represented by the following schematic, depicted in 3' to 5' orientation: 3'-adapter1-NNNNNNNN-gDNA insert-NNNNNNNN-adapter2-5'.

A critical error mode in NGS sequencing is the clonal amplification of errors in the library prep. For PCR free protocols this may be less of a concern, but any low input protocol requires amplification to obtain enough library to load on a sequencer. Errors introduced in the amplification process may show up in a sequencer. A standard reduction in these errors is to remove duplicates from analysis. However, if enough sequencing capacity is given to a sample, duplicate reads (reads with the same start and end position) may occur naturally. Removing these reads would therefore reduce coverage and accuracy of the assay. The use of the synthetic random primers in analysis can allow for a true determination of clonal artifacts vs low frequency mutations. PCR duplicates may have the same random primer sequences on both ends while duplicates due to deep sequencing coverage may have different random primer sequences. Since the synthetic sequence is always at the same position of each read, this information is easily obtained in the analysis.

Non terminating sequencing by synthesis chemistries (such as Qiagen and ION Torrent) experience difficulty sequencing long stretches of homopolymers. This may be mitigated by the complex library generation achieved through termination at each base across the homopolymer described herein.

Accordingly, consistent with the disclosure above, first strand oligonucleotide libraries are generated. To generate a Random Library, a population of first round synthesis oligos is synthesized. The first strand oligonucleotides each comprise a sequence adapter positioned 5' of a random oligomer sequence, such as a 2, 3, 4, 5, 6, 7, 8, 9, 10, 11, 12, 13, 14, 15, 16, 17, 18, 19, 20, 21, 22, 23, 24, 25, 26, 27, 28, 29, 30 mer, or larger oligomer, followed by a 3' OH from which template directed extension occurs. In some cases the sequence adapter is configured to comprise variable identifier sequence. In alternate cases, the sequence adapter is invariant. Sequence adapters are in some cases used as primer binding sites for the later addition of a sequencing adapter, such as an A adapter, such as through standard primer-directed sequence addition through amplification.

In some cases the oligonucleotide population is synthesized such that all possible combinations of a given random oligomer base sequence (such as random 5, 6, 7, 8, 9, or 10 mers) are represented in the first strand oligonucleotide population. In other cases, particularly when a long random oligomer is selected, but also occasionally in cases of smaller oligomers, less than all possible combinations of a given random oligomer base sequence are present.

In some cases the bases of the random oligomer represent an unbiased random distribution of nucleic acid bases in equal proportions. In some cases each base is equally likely to occur at a given position, or in aggregate in a random oligomer population. In other cases, however, to increase the efficiency of annealing and, subsequently, first strand synthesis, the population is synthesized so as to include a bias for random oligomers (such as random 8 mers) having a biased representation of certain bases or base pairs. The human genome, for example, is observed to have a GC percentage of about 40%, rather than a 50% GC composition as expected from a true random base abundance. See, for example FIG. 10A-10C. In some cases the random oligomer distribution is biased such that the overall distribution of random oligomer sequence (such as 8 mer sequence) in the first strand synthesis library reflects that of a skewed target average, such as the average of a target genome, a target locus, a target gene family, a target genomic element (such as exons, introns, or promoter sequence, for example), or in some embodiments, to match the human genome as a whole.

A first strand oligo library or a subset of an oligonucleotide library representing 90%, 80%, 70%, 60%, 50%, 40%, 30%, 20%, 10%, or less than 10% of a first strand oligonucleotide library is contacted to a sample comprising a nucleic acid such as deoxyribonucleic acid or ribonucleic acid. A nucleic acid such as DNA or RNA may be provided in a wide range of amounts. In some cases a genomic DNA sample is provided at or about an amount such as 1 ng, 2 ng, 3 ng, 4 ng, 5 ng, 6 ng, 1 ng, 8 ng, 9 ng, 10 ng, 11 ng, 12 ng, 13 ng, 14 ng, 15 ng, 16 ng, 17 ng, 18 ng, 19 ng, 20 ng, 21 ng, 22 ng, 23 ng, 24 ng, 25 ng, 26 ng, 27 ng, 28 ng, 29 ng, 30 ng, 31 ng, 32 ng, 33 ng, 34 ng, 35 ng, 36 ng, 37 ng, 38 ng, 39 ng, 40 ng, 41 ng, 42 ng, 43 ng, 44 ng, 45 ng, 46 ng, 47 ng, 48 ng, 49 ng, 50 ng, 51 ng, 52 ng, 53 ng, 54 ng, 55 ng, 56 ng, 57 ng, 58 ng, 59 ng, 60 ng, 61 ng, 62 ng, 63 ng, 64 ng, 65 ng, 66 ng, 67 ng, 68 ng, 69 ng, 70 ng, 71 ng, 72 ng, 73 ng, 74 ng, 75 ng, 76 ng, 77 ng, 78 ng, 79 ng, 80 ng, 81 ng, 82 ng, 83 ng, 84 ng, 85 ng, 86 ng, 87 ng, 88 ng, 89 ng, 90 ng, 91 ng, 92 ng, 93 ng, 94 ng, 95 ng, 96 ng, 97 ng, 98 ng, 99 ng or 100 ng, or a value outside of the range defined by the above-mentioned list. As seen below, the number of downstream thermocycles will decrease as the amount of starting template increases. In some cases an RNA sample is provided from RNA extracted from a cell population of as few as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 cells, or more than 100 cells.

Also added to the mixture is a polymerase buffer comprising reagents consistent with DNA polymerase activity. A number of polymerases are consistent with the disclosure herein. In some cases, exemplary polymerases possess strand displacement activity, ddNTP incorporation activity, and are able to incorporate biotin-labeled nucleotides such as biotin-labeled ddNTP. An exemplary polymerase is Sequenase, while an exemplary reverse-transcriptase is HIV reverse-transcriptase.

Also added to the mixture is a population of nucleotides, such as a population comprising dATP, dTTP, dCTP and dGTP, and in some cases also comprising a population of ddNTP, such as ddATP, ddTTP, ddCTP and ddGTP. In some cases only a single species of ddNTP is added to the population of dNTP, such as ddATP alone, ddTTP alone, ddCTP alone, and ddGTP alone. In some cases ddNTP pairs are added, such as ddATP and ddTTP, or ddCTP and ddGTP.

In some cases, the population of ddNTP, such as ddATP, ddTTP, ddCTP and ddGTP added to the composition comprises at least one biotin tagged ddNTP, such as biotin tagged ddATP, biotin tagged ddTTP, biotin tagged ddCTP and biotin tagged ddGTP.

A range of dNTP/ddNTP ratios are consistent with the disclosure herein. Ratios of 99.9%/0.1%, 99.5%/0.5%, 99%/1%, 98%/2% and alternate ratios are consistent with the disclosure herein. In some cases a relative ratio of 99% deoxy NTP to 1% dideoxy NTP is selected.

The mixture is denatured, in some cases by heating above a melting temperature, such as 95° C., 96° C., 97° C., 98° C. or 99° C., or a higher temperature. In many cases a denaturing temperature below 100° C. is exemplary.

The mixture is then cooled, for example on ice for 30 seconds, 1, 2, or more than 2 minutes, or at 4° C. for 30 seconds, 1, 2, or more than 2 minutes, or at an alternate cooling temperature, sufficient to allow for reverse-complementary base-pairing between the first strand synthesis oligonucleotides and the nucleic acid sample such as a genomic DNA sample or an RNA sample. In some cases some or all of the first strand synthesis oligonucleotides demonstrate complete reverse-complementarity between their random oligo (such as a random 8 mer) and the nucleic acid sample sequence such as genomic DNA sequence, cDNA sequence or RNA sequence, to which each binds. In some cases, some oligonucleotides bind to genomic regions that are incompletely reverse-complementary to the oligo's random oligomer (such as a random 8 mer). The failure to base pair with complete reverse complementarity in some cases is not detrimental to subsequent steps in the random library prep process.

A polymerase is added before or after an optional denaturing step in alternate embodiments. The mixture is heated to a temperature consistent with polymerase activity, such as optimal polymerase activity (for example, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., or in some cases a number greater or less than a number in this range), and incubated for a period sufficient to synthesize the first strand library, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more than 45 minutes. In some cases the reaction is agitated at points during this incubation, such as every 10 minutes.

Extension progresses from the 3' OH of the first strand synthesis oligonucleotides, resulting in sequence reverse complementary to the template at the annealing site of each annealed oligo being incorporated at the 3' end of each annealed oligo. Extension continues until a biotin-labeled ddNTP molecule is incorporated, at which point extension terminates. If dNTP and biotin-ddNTP are provided at a ratio of 99%/1%, 50% of the first strand oligos on which extension occurs demonstrate an extension of over 50 bases prior to the incorporation of an biotin-ddNTP molecule. In some cases where other parameters are not simultaneously varied, the proportion of ddNTP decreases, the N50, representing the length of at least 50% of the extension products, increases.

At the completion of the incubation period the reaction is stopped, for example by heat inactivation at 98° C. for five minutes. Alternately, inactivation may be accomplished at another temperature, or by addition of a chelating agent or a dNTPase.

As mentioned above, in some cases an incorporated ddNTP is tagged, such as by a biotin tag. Alternatives to biotin are contemplated in some cases, such as dinitrophenyl. Any affinity tag that is bound to ddNTP and incorporated into a nascent nucleic acid molecule by at least one nucleic acid polymerase is consistent with the disclosure herein. Similarly, any affinity tag that is delivered to a ddNTP end of a nucleic acid molecule, for example via a ddNTP binding moiety, is also consistent with the disclosure herein. In some cases the affinity tag is biotin-ddNTP.

In some cases a tag-binding agent is provided to bind to tagged first strand nucleic acid molecules as provided herein, such as avidin or streptavidin in the case of the tag biotin. In particular cases the streptavidin is bound to magnetic beads, such that streptavidin and any binding partner is isolated by placement in a magnetic field, such as on a magnetic stand.

Tagged first strand libraries are isolated using a tag-binding agent, for example streptavidin against a biotin tagged ddNTP nucleic acid end. In some cases the bead/sample mixture is incubated at 22 C and agitated at 10 minute intervals for 30 minutes. The mixture is then put on a magnetic stand and, upon settling of the beads, the supernatant is removed. The tube is agitated and allowed to settle on a magnetic stand. Beads are washed three times with 200 uL of TE buffer. Alternative tag-binding agent combinations and alternative protocols are consistent with the disclosure herein.

In some cases, first strand molecules are purified independent of tagging, for example by size selection, such as gel electrophoresis, followed by purification of nucleic acids of a desired size. In some cases fragments of a size range of 10-100, 10-150, 10-200, 1-300, 10-350, 10-400, 10-500, 10-600, 10-700, 10-800, 10-900, or 10-1000, bases are isolated.

First strand library templates as purified above are reintroduced into a reaction buffer. For example, templates are in some cases separated from their purification tags, eluted from the streptavidin tags and resuspended in nucleic acid synthesis buffer including dNTP. In some cases, templates remain attached to their purification tags, are washed, and resuspended in reaction buffer. A NaOH wash is included following first strand library generation in some cases, to remove carryover sequences and to decrease self-folding of the first strand library product.

Library second strand molecules are synthesized as follows. A second probe library is added, comprising a population of second strand primers. In some cases each second strand primer comprises a B-adapter sequence 5' to a random oligomer sequence such as a 2, 3, 4, 5, 6, 7, 8, 9, 10, 11, 12, 13, 14, 15, 16, 17, 18, 19, 20, 21, 22, 23, 24, 25, 26, 27, 28, 29, 30 mer, or larger oligomer (for example an 8 mer) followed by a 3' OH from which template directed extension occurs. In some cases the sequence adapter is configured to comprise variable identifier sequence. In alternate cases, the sequence adapter is invariant. Sequence adapters are in some cases used as primer binding sites for the later addition of a sequencing adapter, such as a B adapter, such as through standard primer-directed sequence addition through amplification.

In some cases then oligonucleotide population is synthesized such that all possible combinations of a given random oligomer base sequence (such as random 8 mers) are represented in the second strand oligonucleotide population. In other cases, particularly when a long random oligomer is selected, but also occasionally in cases of smaller oligomers, less than all possible combinations of a given random oligomer base sequence are present.

In some cases the bases of the random oligomer represent an unbiased random distribution of nucleic acid bases in equal proportions. In some cases each base is equally likely to occur at a given position, or in aggregate in a random oligomer population. In other cases, however, to increase the efficiency of annealing and, subsequently, second strand synthesis, the population is synthesized so as to include a bias for random oligomers (such as random 8 mers) having a biased representation of certain bases or base pairs. The human genome, for example, is observed to have a GC percentage of about 40%, rather than a 50% GC composition as expected from a true random base abundance. See, for example FIG. 10A-10C. In some cases the random oligomer distribution is biased such that the overall distribution of random oligomer sequence (such as 8 mer sequence) in the second strand synthesis library reflects that of a skewed target average, such as the average of a target genome, a target locus, a target gene family, a target genomic element (such as exons, introns, or promoter sequence, for example), or in some embodiments, to match the human genome as a whole.

The mixture is heated to 98° C. for 3 minutes. The mixture is cooled on ice for 2 minutes allow for reverse-complementary base-pairing between the second strand synthesis oligonucleotides and the first strand library. It is observed that some oligonucleotides demonstrate complete reverse-complementarity between their random 8 mer and the first strand sequence to which each binds. It is also observed that some oligonucleotides bind to genomic regions that are incompletely reverse-complementary to the oligo's random 8 mer. The failure to base pair with complete reverse complementarity is not detrimental to subsequent steps in the random library prep process.

The composition is heated to room temperature and allowed to continue for 30 minutes. For samples with lower amount of input DNA, this time period is lengthened.

Extension from the 3' OH of the first strand synthesis oligonucleotides is observed, resulting in sequence reverse complementary to the template at the annealing site of each annealed oligo being incorporated at the 3' end of each annealed oligo. Extension continues until the 5' end of the first strand template is reached. It is observed that second-strand oligos annealing away from the 3' end of the first strand template undergo extension from their 3' ends, but are displaced from the first strand by extension reactions primed by oligos annealing further toward the 3' end of the first strand template.

Accordingly, double-stranded library molecules are synthesized, comprising two distinct strands: 1) a first strand having, from the 5' end, an A adapter, a random 8 mer sequence and target sequence on the order of 1-100 nucleotides, terminating in a biotin-tagged ddNTP; and 2) a second strand having, from the 5' end a B adapter, a second random 8 mer sequence, a target sequence derived from the sample, a first random 8 mer sequence reverse complementary to the random 8 mer of the first strand, and sequence reverse complementary to the first A adapter.

In some cases, magnetic streptavidin beads are used to isolate the biotin-tagged double-stranded library molecules. Magnetic streptavidin bead are provided, for example, in binding buffer, mixed, and allowed to settle on a magnetic stand. The binding buffer may then be replaced to a 25 uL, 50 uL, 75 uL, 100 uL, 125 uL, 150 uL, 175 uL, 200 uL, 225 uL, 250 uL, 275 uL, 300 uL, 350 uL, 400 uL, 450 uL, or 500 uL volume and the process repeated. The supernatant is then drawn off and the beads may be resuspended in 5 uL, 10 uL, 12 uL, 14 uL, 16 uL, 18 uL, 20 uL, 22 uL, 24 uL, 26 uL, 28 uL, 30 uL, 31 uL, 32 uL, 33 uL, 34 uL, 35 uL, 36 uL, 37 uL, 38 uL, 39 uL, 40 uL, 41 uL, 42 uL, 43 uL, 44 uL, 45 uL, 46 uL, 47 uL, 48 uL, 49 uL 50 uL, 52 uL, 54 uL, 56 uL, 58 uL, or 60 uL of binding buffer.

In some cases, the biotin-tagged double-stranded library molecules are then added to the resuspended beads. In some cases, the bead/sample mixture is incubated at 22 C and agitated at 10 minute intervals for 30 minutes. The mixture is then put on a magnetic stand and, upon settling of the beads, the supernatant is removed. The tube is agitated and allowed to settle on a magnetic stand. Beads are washed three times with 200 uL of TE buffer. In some cases, this results in a population of streptavidin purified, double-stranded library molecules, comprising two distinct strands: 1) a first strand having, from the 5' end, an A adapter, a random oligomer (such as an 8 mer) sequence and target sequence on the order of 1-100 nucleotides, terminating in a biotin-tagged ddNTP; and 2) a second strand having, from the 5' end a B adapter, a second random oligomer (such as an 8 mer) sequence, a target sequence derived from the sample, a first random oligomer (such as an 8 mer) sequence reverse complementary to the random oligomer (such as an 8 mer) of the first strand, and sequence reverse complementary to the first A adapter. Alternative tag-binding agent combinations and alternative protocols are consistent with the disclosure herein.

The magnetic streptavidin beads bound to the population of double-stranded library molecules are then, for example, resuspended in an amount of nuclease-free water. This amount may be 10 uL, 12 uL, 14 uL, 16 uL, 18 uL, 20 uL, 22 uL, 24 uL, 26 uL, 28 uL, 30 uL, 32 uL, 34 uL, 36 uL, 37 uL, 38 uL, 39 uL, 40 uL, 41 uL, 42 uL, 43 uL, 44 uL, 45 uL, 46 uL, 47 uL, 48 uL, 50 uL, 52 uL, 54 uL, 56 uL, 58 uL, or 60 uL of nuclease-free water. An amount of Adapter A primer and an amount of Adapter B primer is added to the resuspended beads. The amount of Adapter A primer and the amount of Adapter B primer may be the same or they may be different. The amount of Adapter A primer and the amount of Adapter B primer may independently be 1 uL, 2 uL, 3 uL, 4 uL, 5 uL, 6 uL, 7 uL, 8 uL, 9 uL, or 10 uL. In some cases, the Adapter A primer comprises sequence identical to the first adapter of the double-stranded template at the primer's 3' end, and further comprises sequence necessary for sequencing by synthesis reactions as described herein. In other cases, the Adapter A primer has one base-pair mismatch, two base-pair mismatches, three base-pair mismatches, four base-pair mismatches, five base-pair mismatches, six base-pair mismatches, seven base-pair mismatches, eight base-pair mismatches, nine base-pair mismatches, or ten base-pair mismatches with the sequence of the first adapter of the double-stranded template at the primer's 3' end. In some cases, Adapter B primer comprises sequence identical to the second adapter of the second strand of the double-stranded template at the primer's 3' end, and further comprises sequence necessary for sequencing by synthesis reactions as described herein. In other cases, the Adapter B primer has one base-pair mismatch, two base-pair mismatches, three base-pair mismatches, four base-pair mismatches, five base-pair mismatches, six base-pair mismatches, seven base-pair mismatches, eight base-pair mismatches, nine base-pair mismatches, or ten base-pair mismatches with the sequence of the second adapter of the second strand of the double-stranded template at the primer's 3' end.

2×PCR master mix is added in an amount of 10 uL, 15 uL, 20 uL, 25 uL, 30 uL, 35 uL, 40 uL, 45 uL, 50 uL, 55 uL, 60 uL, 65 uL, 70 uL, 75 uL, 80 uL, 85 uL, 90 uL, 95 uL, or 100 uL to the mixture of beads and primers. In some cases, this mixture is then subjected to thermocycling as follows: about 98° C. for about 2 minutes; followed by about 6 cycles of about 98° C., for about 20 second, about 60° C., for about 30 seconds, and about 72° C., for about 30 seconds; following said about six cycles the reaction is held at about 72° C. for about 5 minutes and then is stored at about 4° C. Optimization of the thermocycling conditions is envisioned by the instant disclosure, such as increasing the number of PCR cycles for samples with lower template input. In some cases, amplification is performed without PCR. In an example, template nucleic acid is used with primers containing full length sequencing adapters and first strand synthesis and second strand synthesis is performed with a subsequent size selection. This may or may not require the use of hairpins to avoid dimerization.

In some cases, the sequencing library generated thereby is observed to have the following characteristics. Each double-stranded molecule comprises, in order, an adapter A sequence sufficient for sequencing by synthesis, a first random oligomer sequence (such as an 8 mer), a target region of unknown length but likely within 1-100 bases, a second random oligomer (such as an 8 mer) sequence, and a B adapter sequence sufficient for sequencing by synthesis as disclosed herein.

In some cases, it is observed that the library constituents possess the following characteristics. Each molecule comprises a first molecular tag (such as an 8 mer) that is independent of the first molecular tag (such as an 8 mer) of other molecules in the library. Each molecule comprises a target sequence, corresponding to sequence of the original sample. The starting point of the target sequence, the length of the target sequence, and the endpoint of the target sequence of each given molecule is independent of the starting point, length and end point of each other molecule in the library. Each molecule comprises a second molecular tag (such as an 8 mer) that is independent of the second molecular tag (such as an 8 mer) of other molecules in the library.

In some cases, it is observed that the library, in aggregate, possesses the following characteristics. Substantially all of the sample sequence is represented in the library by multiple overlapping molecules. Substantially all of the library molecules (barring rare events), prior to the final addition of A and B adapters through thermocycling, are unique, varying from one another as to their first molecular tag (such as an 8 mer) sequence, target sequence starting point, target sequence, target sequence length, target sequence end point, and second molecular tag (such as an 8 mer) sequence.

In some cases, a sequence library as generated herein is subjected to sequence by synthesis compatible with its A adapter and B adapter, and the sequence results are assessed. Independently, a second aliquot of the original sample may be prepared for sequencing using standard PCR-based library tagging involving substantial PCR-based amplification of untagged template. The libraries are sequenced and the results compared.

The sample from which the libraries are generated is heterozygous at a first position in the genome, comprising a single base variant. During the library generation, both for the traditional method and using the methods and compositions disclosed herein, point mutations occur at some small frequency.

Sequence from a conventional library generation method is generated and assembled. Sequence reads are observed that differ by a single base at a single homologous position. Multiple reads each representing each allele at the position are obtained. It is inferred that the single base difference represents a base at which the original sample is heterozygous.

In some cases, sequence from a library generated as disclosed herein is generated and analyzed. Sequence reads are observed that differ by a single base at a single homologous position. A number of reads, for example 40, represent the variant base. It is observed that all reads representing the variant base at the position share a common first random oligomer (such as an 8-mer) sequence, a target sequence starting point, a target sequence length, a target sequence end point, and a second random oligomer (such as an 8 mer) sequence—that is, all reads indicating the variant base map to a single unique synthesized library molecule. Another number of reads, such as 40, are observed spanning the base position, none of which indicate the presence of the variant base. It is observed that the number of reads that do not represent the variant base at the homologous position map to multiple distinct synthesized library molecules, as indicated by assessing a first random oligomer (such as an 8-mer) sequence, a target sequence starting point, a target sequence length, a target sequence end point, and a second random oligomer (such as an 8 mer) sequence. It is concluded that the reads representing the variant base result from an error in incorporation followed by differential amplification of the erroneous synthesis event. The sequence information is excluded from the sequence assembly.

In some cases sequence from a library as generated herein is compared to known sequence from a target sample, and entries in the library sequence that represent exact matches to the target sequence throughout the length of the library entry are excluded from the library, such that no entry in the library exactly matches the sample sequence throughout its length, said length including the sequence of the first or second strand oligonucleotide.

In some embodiments, sequence from a library generated as disclosed herein is generated and analyzed with regard to a second putatively heterozygous position. Sequence reads are observed that differ by a single base at a single homologous position. A number of reads, such as 40, represent the variant base. It is observed that another number of reads, such as 50, representing the variant base at the position map to multiple distinct synthesized library molecules, as indicated by assessing a first random oligomer (such as an 8-mer) sequence, a target sequence starting point, a target sequence length, a target sequence end point, and a second random oligomer (such as an 8 mer) sequence. Multiple other reads, such as 40, are observed spanning the base position, none of which indicate the presence of the variant base. It is observed that the number of reads that do not represent the variant base at the homologous position map to multiple distinct synthesized library molecules, as indicated by assessing a first random oligomer (such as an 8-mer) sequence, a target sequence starting point, a target sequence length, a target sequence end point, and a second random oligomer (such as an 8 mer) sequence. It is concluded that the reads representing the variant base result from an accurate representation of the sample sequence, as indicated by the variant appearing in multiple independently generated molecules in the library.

In some cases, a sequence library as generated herein is subjected to sequence by synthesis compatible with its A adapter and B adapter, and the sequence results are assessed. Independently, a second aliquot of the original sample is prepared for sequencing using standard PCR-based library tagging involving substantial PCR-based amplification of untagged template. The libraries are sequenced and the results compared.

It may be observed that a sequence corresponding to a transposon is identified in the traditional sequence library sequencing results. The transposon monomer unit is observed to be found adjacent to multiple non-transposon border sequences, suggesting that it is present in multiple copies in the sample. Transposon reads correspond to a percentage, such as 5%, of the total sequence generated. It is concluded that transposons represent a percentage, such as 5%, of the nucleic acid sample.

Sequence from a library generated as disclosed herein is generated and analyzed. Sequence reads corresponding to a transposon are identified. Transposon reads correspond to a percentage, such as 5%, of the total sequence generated. It is observed that sequence reads mapping to transposon sequence map to a plurality of unique synthesized library molecules, as indicated by assessing a first random oligomer (such as an 8-mer) sequence, a target sequence starting point, a target sequence length, a target sequence end point, and a second random oligomer (such as an 8 mer) sequence. It is observed that each unique synthesized library molecule representing transposon sequence is represented by no more than a low number, such as 2 or 3, of sequence reads. By comparison, the average unique read is represented by a high number, such as between 10 and 20, of sequence reads in this particular data set. This plurality of transposon-mapping reads, in total, represents a percentage, such as 30%, of the total number of unique reads in the sequence dataset.

It is concluded from the sequence data set generated from the sequencing library generated as disclosed herein that transposon sequence represents a percentage, such as about 30%, of the sequence of the sample provided, rather than the percentage, such as 5%, as suggested by analysis of the sequence reads form the library produced through previous methods, and it may be further concluded that the particular transposon sequence is poorly amplified with respect to other sequence in the dataset.

In some cases, a sequence library as generated herein is subjected to sequence by synthesis compatible with its A adapter and B adapter, and the sequence results are assessed. Independently, a second aliquot of the original sample is prepared for sequencing using standard PCR-based library tagging involving substantial PCR-based amplification of untagged template. The libraries are sequenced and the results compared.

It may be observed that a sequence read from the standard PCR-based library tagging comprises sequence that maps to two distinct contigs not believed to be adjacent in the reference human genome. A separate sample is generated and PCR using newly synthesized primers that flank the identified junction sequence is used to confirm that the sequences are in fact adjacent.

Sequence from a library generated as disclosed herein is generated and analyzed. It may be observed that sequence reads spanning the two nonadjacent contig sequences map to a plurality of unique synthesized library molecules, as indicated by assessing first random oligomer (such as an 8-mer) sequence, a target sequence starting point, a target sequence length, a target sequence end point, and a second random oligomer (such as an 8 mer) sequence. It is concluded that the sequence reads spanning the two nonadjacent contig sequences are in fact adjacent in the source of the sample.

In some cases, a total RNA sample is obtained from a population of cells. In some cases the total RNA sample is obtained from a population of cells of as few as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 cells, or more than 100 cells. The sample is contacted with a population of first strand synthesis oligonucleotides. The first strand oligonucleotides each comprise a sequence adapter 5' of a random oligomer (such as an 8 mer) followed by a 3' OH from which template directed extension occurs.

The random oligomer (such as an 8 mer) population of the first round synthesis oligos represents all possible random oligomers of a specified length (such as 8 mers), but the relative abundance of each random oligomer (such as an 8 mer) is biased to match the relative abundance of GC vs AT base pairs in the human transcriptome. An amount of the population, such as be 1 uL, 2 uL, 3 uL, 4 uL, 5 uL, 6 uL, 7 uL, 8 uL, 9 uL, or 10 uL, is added to the sample.

In some cases, also added to the composition is an HIV reverse transcriptase buffer comprising reagents consistent with HIV reverse transcriptase activity and a population of nucleotides comprising dATP, dTTP, dCTP and dGTP, and population of biotin tagged ddATP, biotin tagged ddTTP, biotin tagged ddCTP and biotin tagged ddGTP, at a ratio of deoxy NTP to di-deoxy NTP. A range of dNTP/ddNTP ratios are consistent with the disclosure herein. Ratios of 99.9%/0.1%, 99.5%/0.5%, 99%/1%, 98%/2% and alternate ratios are consistent with the disclosure herein. In some cases a relative ratio of 99% deoxy NTP to 1% dideoxy NTP is selected. An amount, such as 1 uL, 2 uL, 3 uL, 4 uL, 5 uL, 6 uL, 7 uL, 8 uL, 9 uL, or 10 uL of the buffer/NTP composition is added to the sample.

In some cases, the mixture is diluted to a total volume. This total volume may be 1 uL, 2 uL, 3 uL, 4 uL, 5 uL, 6 uL, 7 uL, 8 uL, 9 uL, 10 uL, 11 uL, 12 uL, 13 uL, 14 uL, 15 uL, 16 uL, 17 uL, 18 uL, 19 uL, 20 uL, 21 uL, 22 uL, 23 uL, 24 uL, 25 uL, 26 uL, 27 uL, 28 uL, 29 uL, or 30 uL. The mixture is denatured, in some cases by heating above a melting temperature, such as 95° C., 96° C., 97° C., 98° C., or 99° C., or a higher temperature, for a period of time. In many cases a temperature below 100° C. is exemplary. The period of time may be less than 1 minute, about 1 minute, about 2 minutes, about 3 minutes, about 4 minutes, about 5 minutes, about 6 minutes, about 7 minutes, about 8 minutes, about 9 minutes, or about 10 minutes. During this time the genomic DNA is caused to 'melt' into single-strands unbound by hydrogen boding between complementary bases.

The mixture is then cooled, for example on ice for 30 seconds, 1, 2, or more than 2 minutes, or at 4° C. for 30 seconds, 1, 2, or more than 2 minutes, or at an alternate cooling temperature, sufficient to allow for reverse-complementary base-pairing between the first strand synthesis oligonucleotides and the RNA sample. In some cases some or all of the first strand synthesis oligonucleotides demonstrate complete reverse-complementarity between their random oligo (such as a random 8 mer) and the RNA sequence to which each binds. In some cases, some oligonucleotides bind to genomic regions that are incompletely reverse-complementary to the oligo's random oligomer (such as a random 8 mer). The failure to base pair with complete reverse complementarity in some cases is not detrimental to subsequent steps in the random library prep process.

In some cases, an HIV reverse transcriptase (1 uL) having strand displacement activity and the ability to incorporate biotin-ddNTP is added to the composition. The mixture is heated to a temperature consistent with HIV reverse transcriptase activity, such as optimal activity (for example, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., or in some cases a number greater or less than a number in this range), and incubated for a period sufficient to synthesize the first strand library, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more than 45 minutes. In some cases the reaction is agitated at points during this incubation, such as every 10 minutes.

Extension progresses from the 3' OH of the first strand synthesis oligonucleotides, resulting in sequence reverse complementary to the template at the annealing site of each annealed oligo being incorporated at the 3' end of each annealed oligo. Extension continues until a biotin-labeled ddNTP molecule is incorporated, at which point extension terminates. If dNTP and biotin-ddNTP are provided at a ratio of 99%/1%, 50% of the first strand oligos on which extension occurs demonstrate an extension of over 50 bases prior to the incorporation of a biotin-ddNTP molecule. In some cases where other parameters are not simultaneously varied, the proportion of ddNTP decreases, the N50, representing the length of at least 50% of the extension products, increases.

At the completion of the incubation period the reaction is stopped, for example by heat inactivation at 98° C. for five minutes. Alternately, inactivation may be accomplished at another temperature, or by addition of a chelating agent or a dNTPase.

In some cases, the sample is then subjected to purification, second strand synthesis and library tag addition as described above.

In some cases, traditional quantitative PCR (Q-PCR) is performed on an aliquot of a total RNA sample obtained from a population of cells, such as a population of cells of as few as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 cells, or more than 100 cells. The sample is reverse-transcribed using random primers, and PCR is performed in the presence of a double-stranded DNA binding dye, such as SYBR-Green, to quantify amplicon synthesis over time, as a measure of underlying template copy number.

It may be observed that a first transcript and a second transcript of similar length lead to double-stranded DNA-binding dye florescence (such as SYBR fluorescence) of their respective amplicons at a similar cycle in the amplification process. It is concluded that the first and the second transcript accumulate at about the same level in the population of cells from which the RNA template is derived.

The cDNA sequence library as described above is sequenced and the results are analyzed. It is observed that the first transcript is represented in a number of sequence reads, such as 100 reads, mapping to 1 unique template as indicated by assessing a first random oligomer (such as an 8-mer) sequence, a target sequence starting point, a target sequence length, a target sequence end point, and a second random oligomer (such as an 8 mer) sequence. The second transcript is represented in a number of sequence reads, such as 100 reads, mapping to 50 unique templates as indicated by assessing a first random oligomer (such as an 8-mer) sequence, a target sequence starting point, a target sequence length, a target sequence end point, and a second random oligomer (such as an 8 mer) sequence, and that each is represented by 1-3 reads.

It can then be concluded that the second transcript is present at a level that is 50-fold greater than that of the first template. It is also concluded that the single template generated form the first transcript is differentially amplified relative to the templates of the second strand.

In some cases, a genomic DNA sample is obtained and fragmented. Fragments are size selected to have a minimum size, such as 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, or 30 kb. Size-selected fragments are diluted to not more than 100 fragments per aliquot and distributed into separate reaction tubes.

In some cases, each aliquoted sample is then contacted with a population of first strand synthesis oligonucleotides. The first strand oligonucleotides each comprise a unique reaction tube label 5' to a sequence adapter 5' of a random oligomer sequence, such as a 2, 3, 4, 5, 6, 7, 8, 9, 10, 11, 12, 13, 14, 15, 16, 17, 18, 19, 20, 21, 22, 23, 24, 25, 26, 27, 28, 29, 30 mer, or larger oligomer, followed by a 3' OH from which template directed extension occurs. The reaction tube label sequence is common to all first strand synthesis oligos added to a given tube, but varies among tubes. The random oligomer (such as an 8 mer) is unique to a single oligo, although a small degree of redundancy is easily tolerated by the methods disclosed herein, and even a large degree of redundancy is accommodated.

As discussed above, the random oligomer (such as an 8 mer) population of the first round synthesis oligos represents all possible random oligomers of a specified length (such as 8 mers), but the relative abundance of each random oligomer of a specified length (such as 8 mers) is biased to match the relative abundance of GC vs AT base pairs in the human genome. An amount of the population, such as be 1 uL, 2 uL, 3 uL, 4 uL, 5 uL, 6 uL, 7 uL, 8 uL, 9 uL, or 10 uL, is added to the sample.

Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP. A range of dNTP/ddNTP ratios are consistent with the disclosure herein. Ratios of 99.9%/0.1%, 99.5%/0.5%, 99%/1%, 98%/2% and alternate ratios are consistent with the disclosure herein. In some cases a relative ratio of 99% deoxy NTP to 1% dideoxy NTP is selected. An amount, such as 1 uL, 2 uL, 3 uL, 4 uL, 5 uL, 6 uL, 7 uL, 8 uL, 9 uL, or 10 uL of the buffer/NTP composition is added to the sample.

In some cases, the mixture is diluted to a total volume. This total volume may be 1 uL, 2 uL, 3 uL, 4 uL, 5 uL, 6 uL, 7 uL, 8 uL, 9 uL, 10 uL, 11 uL, 12 uL, 13 uL, 14 uL, 15 uL, 16 uL, 17 uL, 18 uL, 19 uL, 20 uL, 21 uL, 22 uL, 23 uL, 24 uL, 25 uL, 26 uL, 27 uL, 28 uL, 29 uL, or 30 uL. The mixture is denatured, in some cases by heating above a melting temperature, such as 95° C., 96° C., 97° C., 98° C., or 99° C., or a higher temperature, for a period of time. In many cases a temperature below 100° C. is exemplary. The period of time may be less than 1 minute, about 1 minute, about 2 minutes, about 3 minutes, about 4 minutes, about 5 minutes, about 6 minutes, about 7 minutes, about 8 minutes, about 9 minutes, or about 10 minutes. During this time the genomic DNA is caused to 'melt' into single-strands unbound by hydrogen boding between complementary bases.

The mixture is then cooled, for example on ice for 30 seconds, 1, 2, or more than 2 minutes, or at 4° C. for 30 seconds, 1, 2, or more than 2 minutes, or at an alternate cooling temperature, sufficient to allow for reverse-complementary base-pairing between the first strand synthesis oligonucleotides and the RNA sample. In some cases some or all of the first strand synthesis oligonucleotides demonstrate complete reverse-complementarity between their random oligo (such as a random 8 mer) and the RNA sequence to which each binds. In some cases, some oligonucleotides bind to genomic regions that are incompletely reverse-complementary to the oligo's random oligomer (such as a random 8 mer). The failure to base pair with complete reverse complementarity in some cases is not detrimental to subsequent steps in the random library prep process.

In some embodiments, SEQUENASE DNA polymerase (1 uL) having strand displacement activity and able to incorporate biotin-ddNTP is added to the composition. The mixture is heated to a temperature consistent with SEQUENASE activity, such as optimal activity (for example, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., or in some cases a number greater or less than a number in this range), and incubated for a period sufficient to synthesize the first strand library, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more than 45 minutes. In some cases the reaction is agitated at points during this incubation, such as every 10 minutes.

Extension progresses from the 3' OH of the first strand synthesis oligonucleotides, resulting in sequence reverse complementary to the template at the annealing site of each annealed oligo being incorporated at the 3' end of each annealed oligo. Extension continues until a biotin-labeled ddNTP molecule is incorporated, at which point extension terminates. If dNTP and biotin-ddNTP are provided at a ratio of 99%/1%, 50% of the first strand oligos on which extension occurs demonstrate an extension of over 50 bases prior to the incorporation of a biotin-ddNTP molecule. In some cases where other parameters are not simultaneously varied, the proportion of ddNTP decreases, the N50, representing the length of at least 50% of the extension products, increases.

At the completion of the incubation period the reaction is stopped, for example by heat inactivation at 98° C. for five minutes. Alternately, inactivation may be accomplished at another temperature, or by addition of a chelating agent or a dNTPase.

In some cases, the sample is then subjected to purification and second strand synthesis as indicated above. Additional cycles are added to the library tag addition thermocycling steps to account for the low amount of starting sample material.

In some cases, traditional sequencing is performed on a genomic sample aliquoted from the sample described above prior to the dilution step. A sequencing library is generated and sequence information is generated. Sequence data is assembled against a human genome contig scaffold. A first and a second single nucleotide polymorphism within the sequence data are identified, and the sample is scored as being heterozygous at these sites. The heterozygous sites map to a single contig. It may not be clear from the sequence information what the physical linkage status is among the polymorphisms—that is, it may not be clear which polymorphisms are paired with one another, or in phase with one another, on the same actual nucleic acid molecule, and which polymorphisms are not physically linked.

In some embodiments, a second sample is prepared as disclosed above. The tagged library is bulked and sequenced. The same first and second polymorphisms are identified. The polymorphisms are each mapped to multiple templates varying in their first random oligomer (such as an 8 mer) sequence, target sequence start site, target sequence length, target sequence end site and second random oligomer (such as an 8 mer) sequence, indicating that the polymorphisms are independently generated from the sample rather than resulting from a single error in library synthesis which was then differentially amplified.

The first variant of the first polymorphism and the first variant of the second polymorphism are observed to map to some library templates that share a common aliquot tag 5' of their (differing) 5' random oligomer (such as an 8 mer) sequences. The second variant of the first polymorphism and the second variant of the second polymorphism are observed to map to some library templates that share a common aliquot tag, that differs from that of the first variants mentioned immediately previously, 5' of their (differing) 5' first random oligomer (such as an 8 mer) sequence.

It is concluded that the first variant of the first polymorphism and the first variant of the second polymorphism are in phase—that is, they map to a single physical molecule. It is concluded that the second variant of the first polymorphism and the second variant of the second polymorphism are in phase—that is, that they map to a single molecule.

This conclusion is not inconsistent with the presence of some variants also mapping to some library templates that have unique aliquot tags. These sequences that map to unique aliquot tags are inferred to result from events whereby a template molecule is cleaved between the loci of the two polymorphisms.

This conclusion is also not inconsistent with some sequence reads sharing a common aliquot tag despite mapping to disparate regions of the genome. As the aliquots comprise more than a single molecule, different sequence reads will map to different regions of the genome. Provided that two overlapping, out of phase nucleic acid fragments do not end up in a single aliquot, the downstream analysis is unaffected. In the event that two overlapping, out of phase nucleic acid fragments end up in a single aliquot, the presence of both alleles at a locus will indicate that non-physically linked molecules are present in a single sample.

In some cases, traditional sequencing is performed on a genomic sample aliquoted from the sample described above prior to the dilution step. A sequencing library is generated and sequence information is generated. Sequence data is assembled against a human genome contig scaffold. Sequence corresponding to a repeat unit known to exist at a number of distinct loci, such as 50, in the genome is obtained. A polymorphism is identified in the sequence repeat that may affect transcription of genes at adjacent loci. The polymorphism is embedded in and surrounded by repeat sequence such that the polymorphism cannot be mapped to any of the number, such as 50, distinct loci in the genome.

A second sample is prepared as disclosed above. The tagged library is bulked and sequenced. Sequence is obtained corresponding to the polymorphism discussed above that may affect transcription of genes at adjacent loci. The polymorphism is embedded in and surrounded by repeat sequence. The polymorphism is mapped to multiple templates varying in their first random oligomer (such as an 8 mer) sequence, target sequence start site, target sequence length, target sequence end site and second random oligomer (such as an 8 mer) sequence, indicating that the polymorphisms are independently generated from the sample rather than resulting from a single error in library synthesis which was then differentially amplified.

The polymorphism is observed to map to some library templates that share a common aliquot tag 5' of their (differing) 5' random oligomer (such as an 8 mer) sequences. Sequence corresponding to the repeat region flanking the polymorphism is observed to share a common aliquot tag 5' of their (differing) 5' random oligomer (such as an 8 mer) sequences. Sequences spanning a repeat border, corresponding to both repeat sequence and adjacent sequence that uniquely maps to a single region of the human genome are identified, and it is observed that they share a common aliquot tag 5' of their (differing) 5' random oligomer (such as an 8 mer) sequences.

It is concluded that the polymorphism that may affect transcription of genes at adjacent loci maps to the repeat region immediately adjacent to the locus of the sequence that uniquely maps to a single region of the genome, and not the other number of repeat regions, such as 49, of highly similar sequence distributed elsewhere throughout the genome.

In some cases, an oligonucleotide population is generated. Each oligo comprises a sequence adapter 5' of a oligomer specifically synthesized to anneal adjacent to a region of interest in the human genome. The length of this oligomer may be a 2, 3, 4, 5, 6, 7, 8, 9, 10, 11, 12, 13, 14, 15, 16, 17, 18, 19, 20, 21, 22, 23, 24, 25, 26, 27, 28, 29, 30 mer, or larger oligomer. An example is a 25 mer. Examples of regions of interest include but are not limited to exons, promoter regions, transcription enhances, promoter regions, regions to which genetic diseases map, regions known to be mutant in cancer cell lines or tumor cells, and loci known to be polymorphic in at least one human population. Oligos are synthesized to anneal to either stand adjacent to a region of interest as identified above.

In some cases, a genomic DNA sample is obtained. The sample is contacted with a population of targeted first strand synthesis oligonucleotides as described above. An amount of the population, such as be 1 uL, 2 uL, 3 uL, 4 uL, 5 uL, 6 uL, 7 uL, 8 uL, 9 uL, or 10 uL, is added to the sample.

Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a ratio of deoxy NTP to di-deoxy NTP. A range of dNTP/ddNTP ratios are consistent with the disclosure herein. Ratios of 99.9%/0.1%, 99.5%/0.5%, 99%/1%, 98%/2% and alternate ratios are consistent with the disclosure herein. In some cases a relative ratio of 99% deoxy NTP to 1% dideoxy NTP is selected. An amount, such as 1 uL, 2 uL, 3 uL, 4 uL, 5 uL, 6 uL, 7 uL, 8 uL, 9 uL, or 10 uL of the buffer/NTP composition is added to the sample.

In some cases, the mixture is diluted to a total volume. This total volume may be 1 uL, 2 uL, 3 uL, 4 uL, 5 uL, 6 uL, 7 uL, 8 uL, 9 uL, 10 uL, 11 uL, 12 uL, 13 uL, 14 uL, 15 uL, 16 uL, 17 uL, 18 uL, 19 uL, 20 uL, 21 uL, 22 uL, 23 uL, 24 uL, 25 uL, 26 uL, 27 uL, 28 uL, 29 uL, or 30 uL. The mixture is denatured, in some cases by heating above a melting temperature, such as 95° C., 96° C., 97° C., 98° C., or 99° C., or a higher temperature, for a period of time. In many cases a temperature below 100° C. is exemplary. The period of time may be less than 1 minute, about 1 minute, about 2 minutes, about 3 minutes, about 4 minutes, about 5 minutes, about 6 minutes, about 7 minutes, about 8 minutes, about 9 minutes, or about 10 minutes. During this time the genomic DNA is caused to 'melt' into single-strands unbound by hydrogen boding between complementary bases.

The mixture is then cooled, for example on ice for 30 seconds, 1, 2, or more than 2 minutes, or at 4° C. for 30 seconds, 1, 2, or more than 2 minutes, or at an alternate cooling temperature, sufficient to allow for reverse-complementary base-pairing between the first strand synthesis oligonucleotides and the RNA sample. In some cases some or all of the first strand synthesis oligonucleotides demonstrate complete reverse-complementarity between their random oligo (such as a random 8 mer) and the RNA sequence to which each binds. In some cases, some oligonucleotides bind to genomic regions that are incompletely reverse-complementary to the oligo's random oligomer (such as a random 8 mer). The failure to base pair with complete reverse complementarity in some cases is not detrimental to subsequent steps in the random library prep process.

In some embodiments, SEQUENASE DNA polymerase (1 uL) having strand displacement activity and able to incorporate biotin-ddNTP is added to the composition. The mixture is heated to a temperature consistent with SEQUENASE activity, such as optimal activity (for example, 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., or in some cases a number greater or less than a number in this range), and incubated for a period sufficient to synthesize the first strand library, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more than 45 minutes. In some cases the reaction is agitated at points during this incubation, such as every 10 minutes.

Extension progresses from the 3' OH of the first strand synthesis oligonucleotides, resulting in sequence reverse complementary to the template at the annealing site of each annealed oligo being incorporated at the 3' end of each annealed oligo. Extension continues until a biotin-labeled ddNTP molecule is incorporated, at which point extension terminates. If dNTP and biotin-ddNTP are provided at a ratio of 99%/1%, 50% of the first strand oligos on which extension occurs demonstrate an extension of over 50 bases prior to the incorporation of a biotin-ddNTP molecule. In some cases where other parameters are not simultaneously varied, the proportion of ddNTP decreases, the N50, representing the length of at least 50% of the extension products, increases.

In some cases, the sample is then subjected to purification and second strand synthesis as indicated above.

In some cases, traditional sequencing is performed on a genomic sample aliquoted from the sample described above. A sequencing library is generated and sequence information is generated. Sequence data is assembled against a human genome contig scaffold. The vast majority of the sequence information generated is not of use for diagnosis of an individual from which the sample is obtained.

Sequencing is also performed on the targeted sequencing library generated as described above. It is found that the sequence reads are substantially enriched for sequence of use for diagnosis of an individual from which the sample is obtained, and that substantially fewer reagents and less computing capacity is required to obtain the relevant information.

In some cases, a targeted sequencing first strand oligonucleotide library is generated having 3' annealing regions that tag each member of a cancer locus panel containing a number of members (such as 102 members). See FIG. 19. The annealing regions are selected to anneal at intervals of approximately 5 bp, 6 bp, 7 bp, 8 bp, 9 bp, 10 bp, 11 bp, 12 bp, 13 bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, or 30 bp (for example, 20 bp intervals) throughout the locus of each member of the panel in each direction.

A genomic nucleic acid sample from a tumor diagnosed as benign and demonstrating no characteristics of metastasis or malignancy is isolated. The tissue comprises cells with substantial polymorphism in genomic sequence of at least one locus listed on the genomic locus panel.

Traditional PCR using a panel of primers spanning each locus is used to assess the mutation status of the tumor tissue. Amplicons are generated, tagged to form a library, and sequenced. Each locus is present in the final product at the expected size for wild type alleles of the each locus.

The cancer panel targeted first strand oligonucleotide library having 3' annealing regions that tag each member of the cancer locus panel containing a number of members (such as 102 members) is applied to an aliquot of the genomic nucleic acid sample isolated from the tumor.

A sequencing library is generated therefrom and analyzed. It is determined that wild-type copies of each member of the cancer panel containing a number of members (such as 102 members) are present in the sample.

In a subset of reads mapping to a cell division repressor, it is determined that the locus is interrupted by a translocation, as indicated by the presence of independent reads, as judged by the presence of distinct random oligomer (such as an 8 mer) sequence and cancer locus sequence starting positions, independently spanning a junction between the locus of interest and translocated sequence.

In a subset of reads mapping to a cell growth repressor, it is determined that the locus has undergone a deletion event, as indicated by the presence of independent reads, as judged by the presence of distinct random oligomer (such as an 8 mer) sequence and cancer locus sequence starting positions, independently spanning a deletion site at which the ends of the locus are present but joined in the absence of intervening sequence.

The cancer panel sequence library data is found to confirm the results of the PCR primer panel assay—namely, that wild type copies of each locus are present in the genomic sample. In addition, the cancer panel sequencing data identifies mutations in two loci that may be indicative of tumor progression. The sample is not homozygous for either of these mutations, and it is expected that each is present in a clear minority of the sample as a whole.

Neither of these mutations is identified by the PCR primer panel assay. The translocation, in all likelihood, is not differentially amplified as the primers which target the locus are too far apart to generate an amplicon, and the wild type amplicon amplifies efficiently enough to sequester the vast majority of primers targeting the locus. The deletion is unlikely to be detected as the effect is to bring the primers close enough that their amplicon is comparable in size to a primer dimer or other amplification artifact, and difficult to purify for sequencing.

This demonstrates how the cancer panel, and the methods disclosed herein generally, are capable of generating sequence data, easily verified by tag comparison and sequence start site, corresponding to rare events in genomic samples that are easily overlooked in more traditional targeted sequence generation protocols.

In some cases, to generate a Random Library, a population of first round synthesis oligos is synthesized. The first strand oligonucleotides each comprise an A region positioned 5' of a sequence adapter, itself positioned 5' of a random oligomer (such as an 8 mer) followed by a 3' OH from which template directed extension occurs. The population is synthesized such that all random oligomers of a specified length (such as 8 mers) are represented in the first strand oligonucleotide population. However, to increase the efficiency of annealing and, subsequently, first strand synthesis, the population is synthesized so as to include a bias for random oligomers (such as 8 mers) having a GC percentage of about 40%, such that the overall distribution of random oligomer (such as 8 mer) sequence in the first strand synthesis library reflects that of the human genome as a whole.

A first oligonucleotide primer is designed to be identical to the A adapter region of the first strand oligonucleotide synthesis library above, and to have a 3'OH positioned 5' to the sequence adapter sequence.

A second primer is synthesized having a similar annealing and melting temperature to the first 'A adaptor' region primer, and having specificity such that it anneals with its 3'OH directed so that extension will be directed toward a nucleic acid region of interest.

In some cases, a genomic nucleic acid sample is obtained. A genomic nucleic acid sample may be provided in a wide range of amounts. In some cases a genomic DNA sample is provided at or about an amount such as 1 pg, 2 pg, 3 pg, 3.2 pg, 4 pg, 5 pg, 6 pg, 7 pg, 8 pg, pg, 10 pg, 20 pg, 30 pg, 40 pg, 50 pg, 60 pg, 70 pg, 80 pg 90 pg, 100 pg, 200 pg, 300 pg, 400 pg, 500 pg, 600 pg, 700 pg, 800 pg, 900 pg, 1 ng, 2 ng, 3 ng, 4 ng, 5 ng, 6 ng, 7 ng, 8 ng, 9 ng, 10 ng, 11 ng, 12 ng, 13 ng, 14 ng, 15 ng, 16 ng, 17 ng, 18 ng, 19 ng, 20 ng, 21 ng, 22 ng, 23 ng, 24 ng, 25 ng, 26 ng, 27 ng, 28 ng, 29 ng, 30 ng, 31 ng, 32 ng, 33 ng, 34 ng, 35 ng, 36 ng, 37 ng, 38 ng, 39 ng, 40 ng, 41 ng, 42 ng, 43 ng, 44 ng, 45 ng, 46 ng, 47 ng, 48 ng, 49 ng, 50 ng, 51 ng, 52 ng, 53 ng, 54 ng, 55 ng, 56 ng, 57 ng, 58 ng, 59 ng, 60 ng, 61 ng, 62 ng, 63 ng, 64 ng, 65 ng, 66 ng, 67 ng, 68 ng, 69 ng, 70 ng, 71 ng, 72 ng, 73 ng, 74 ng, 75 ng, 76 ng, 77 ng, 78 ng, 79 ng, 80 ng, 81 ng, 82 ng, 83 ng, 84 ng, 85 ng, 86 ng, 87 ng, 88 ng, 89 ng, 90 ng, 91 ng, 92 ng, 93 ng, 94 ng, 95 ng, 96 ng, 97 ng, 98 ng, 99 ng or 100 ng, or a value outside of the range defined by the above-mentioned list. An example is 50 ng of the sample. The sample is aliquoted into a PCR reaction buffer comprising reagents necessary for amplification. A primer pair sufficient for amplification of a region of interest is added. A thermostable heat-activated DNA polymerase is added, and the mixture is subjected to thermocycling (about 98° C., for about 30 seconds; followed by about six cycles of about 95° C., about 30 seconds, about 60° C., for about 20 seconds, about 72° C., for about 30 seconds; a final about 72° C. for about 2 minutes, and then storage at about 4° C.) to amplify the region of interest. Optimization of the thermocycling conditions is envisioned by the instant disclosure.

An aliquot of the reaction is analyzed. It is determined that the amount of amplicon generated is insufficient for further analysis.

A second amount of the sample (such as 50 ng of the sample) is aliquoted into a PCR reaction buffer comprising reagents necessary for amplification. A primer pair sufficient for amplification of a region of interest is added. A thermostable heat-activated DNA polymerase is added, and the mixture is subjected to thermocycling (about 98° C., for about 30 seconds; followed by about thirty cycles of about 95° C., about 30 seconds, about 60° C., for about 20 seconds, about 72° C., for about 30 seconds; a final about 72° C. for about 2 minutes, and then storage at about 4° C.) to amplify the region of interest. Optimization of the thermocycling conditions is envisioned by the instant disclosure.

An aliquot of the reaction is analyzed. It is determined that the amount of amplicon generated is sufficient for further analysis. It is also found that the amplicon comprises point mutations consistent with rare misincorporation events in amplification that, when occurring early in amplification, may represent a large fraction of the final product.

Random first strand oligo synthesis is performed as described above on an amount (for example 50 ng) of the same starting sample. A sample is aliquoted into a PCR reaction buffer comprising reagents necessary for amplification. A first primer identical to a region of the A adapter, and a second primer specific for a region of interest and sufficient for amplification of a region of interest is added. A thermostable heat-activated DNA polymerase is added, and the mixture is subjected to thermocycling (about 98° C., for about 30 seconds; followed by about thirty cycles of about 95° C., about 30 seconds, about 60° C., for about 20 seconds, about 72° C., for about 30 seconds; a final about 72° C. for about 2 minutes, and then storage at about 4° C.) to amplify the region of interest.

An aliquot of the reaction is analyzed. It is determined that the amount of amplicon generated is sufficient for further analysis. It is also found that, due to the first strand synthesis performed prior to PCR amplification, a large amount of template is generated, such that fewer cycles of amplification are necessary to generate a sufficient amount of amplicon for downstream analyses. Due to the lower number of cycles and the higher amount of starting template, misincorporation errors in the early cycles have little chance of being differentially amplified so as to represent a disproportional amount of the reaction product.

The sequence adapter, random oligomer (such as an 8 mer) sequence, and position of the junction between the random oligomer (such as an 8 mer) and the target sequence of each amplicon is examined. Duplicate amplicons are identified, and duplicate sequence information is disregarded so that each first strand synthesis molecule sequence is assessed in equal proportions. Sequence variant information which is not independently supported by two distinct first strand template sequences is disregarded as representing an error in synthesis. Sequence information corroborated by two independently synthesized first strand molecules is retained as representative of the starting sample sequence.

Some embodiments of the disclosure herein comprise kits, such as library generation kits. Some kits comprise a first stand oligo library. The first strand oligonucleotides in such a library each comprise a sequence adapter positioned 5' of a random oligomer sequence, such as a 2, 3, 4, 5, 6, 7, 8, 9, 10, 11, 12, 13, 14, 15, 16, 17, 18, 19, 20, 21, 22, 23, 24, 25, 26, 27, 28, 29, 30 mer, or larger oligomer, followed by a 3' OH from which template directed extension occurs. In some cases the sequence adapter is configured to comprise variable identifier sequence. In alternate cases, the sequence adapter is invariant. Sequence adapters are in some cases used as primer binding sites for the later addition of a sequencing adapter, such as an A adapter, such as through standard primer-directed sequence addition through amplification.

In some cases then oligonucleotide population is synthesized such that all possible combinations of a given random oligomer base sequence (such as random 8 mers) are represented in the first strand oligonucleotide population. In other cases, particularly when a long random oligomer is selected, but also occasionally in cases of smaller oligomers, less than all possible combinations of a given random oligomer base sequence are present.

In some cases the bases of the random oligomer represent an unbiased random distribution of nucleic acid bases in equal proportions. In some cases each base is equally likely to occur at a given position, or in aggregate in a random oligomer population. In other cases, however, to increase the efficiency of annealing and, subsequently, first strand synthesis, the population is synthesized so as to include a bias for random oligomers (such as random 8 mers) having a biased representation of certain bases or base pairs. The human genome, for example, is observed to have a GC percentage of about 40%, rather than a 50% GC composition as expected from a true random base abundance. See, for example FIG. 10C (right panel). In some cases the random oligomer distribution is biased such that the overall distribution of random oligomer sequence (such as 8 mer sequence) in the first strand synthesis library reflects that of a skewed target average, such as the average of a target genome, a target locus, a target gene family, a target genomic element (such as exons, introns, or promoter sequence, for example), or in some embodiments, to match the human genome as a whole.

In alternate embodiments, a targeted first strand oligonucleotide library is provided. In some aspects each oligo comprises a sequence adapter 5' of a nucleic acid sequences specifically synthesized to anneal adjacent to a region of interest in the human genome. In some aspects the sequence is 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 base. In some aspects the sequence is 25 bases. Examples of regions of interest include but are not limited to exons, promoter regions, transcription enhances, promoter regions, regions to which genetic diseases map, regions known to be mutant in cancer cell lines or tumor cells, and loci known to be polymorphic in at least one human population. Oligos are synthesized to anneal to either stand adjacent to a region of interest as identified above.

Some kits comprise a second strand oligonucleotide library. In some cases a second strand oligonucleotide library comprises a population of second strand primers. In some cases each second strand primer comprises a B-adapter sequence 5' to a random oligomer sequence such as a 2, 3, 4, 5, 6, 7, 8, 9, 10, 11, 12, 13, 14, 15, 16, 17, 18, 19, 20, 21, 22, 23, 24, 25, 26, 27, 28, 29, 30 mer, or larger oligomer (for example an 8 mer followed by a 3' OH from which template directed extension occurs. In some cases the sequence adapter is configured to comprise variable identifier sequence. In alternate cases, the sequence adapter is invariant. Sequence adapters are in some cases used as primer binding sites for the later addition of a sequencing adapter, such as a B adapter, such as through standard primer-directed sequence addition through amplification.

In some cases then oligonucleotide population is synthesized such that all possible combinations of a given random oligomer base sequence (such as random 8 mers) are represented in the second strand oligonucleotide population. In other cases, particularly when a long random oligomer is selected, but also occasionally in cases of smaller oligomers, less than all possible combinations of a given random oligomer base sequence are present.

In some cases the bases of the random oligomer represent an unbiased random distribution of nucleic acid bases in equal proportions. In some cases each base is equally likely to occur at a given position, or in aggregate in a random oligomer population. In other cases, however, to increase the efficiency of annealing and, subsequently, second strand synthesis, the population is synthesized so as to include a bias for random oligomers (such as random 8 mers) having a biased representation of certain bases or base pairs. The human genome, for example, is observed to have a GC percentage of about 40%, rather than a 50% GC composition as expected from a true random base abundance. See, for example FIG. 10C (right panel). In some cases the random oligomer distribution is biased such that the overall distribution of random oligomer sequence (such as 8 mer sequence) in the second strand synthesis library reflects that of a skewed target average, such as the average of a target genome, a target locus, a target gene family, a target genomic element (such as exons, introns, or promoter sequence, for example), or in some embodiments, to match the human genome as a whole.

In some cases an extension mixture is included. In some kits an extension buffer comprises reagents consistent with DNA polymerase activity. A number of polymerases are consistent with the disclosure herein. In some cases, exemplary polymerases possess strand displacement activity, ddNTP incorporation activity, and are able to incorporate biotin-labeled nucleotides such as biotin-labeled ddNTP. An exemplary polymerase is SEQUENASE, while an exemplary reverse-transcriptase is HIV reverse-transcriptase.

Also added to the mixture is a population of nucleotides, such as a population comprising dATP, dTTP, dCTP and dGTP, and in some cases also comprising a population of ddNTP, such as ddATP, ddTTP, ddCTP and ddGTP. In some cases only a single species of ddNTP is added to the population of dNTP, such as ddATP alone, ddTTP alone, ddCTP, alone, and ddGTP alone. In some cases ddNTP pairs are added, such as ddATP and ddTTP, or ddCTP and ddGTP. In some cases, modified nucleotides are used. In some cases, modified nucleotides are used in the first strand synthesis reaction and may prevent a first strand primer from binding and extending using displaced product as template. Modified nucleotides include 2,6 Diaminopurine and 2-thiothymidine (or uracil, without a methyl group at 5 position).

In some cases, the population of ddNTP, such as ddATP, ddTTP, ddCTP and ddGTP added to the composition comprises at least one biotin tagged ddNTP, such as biotin tagged ddATP, biotin tagged ddTTP, biotin tagged ddCTP and biotin tagged ddGTP.

Alternatives to biotin are contemplated in some methods and kits, such as dinitrophenyl. Any affinity tag that is bound to ddNTP and incorporated into a nascent nucleic acid molecule by at least one nucleic acid polymerase is consistent with the disclosure herein. Similarly, any affinity tag that is delivered to a ddNTP end of a nucleic acid molecule, for example via a ddNTP binding moiety, is also consistent with the disclosure herein. In some cases the affinity tag is biotin-ddNTP.

In some cases a tag-binding agent is provided to bind to tagged first strand nucleic acid molecules as provided herein, such as avidin or streptavidin in the case of the tag biotin. In particular cases the streptavidin is bound to magnetic beads, such that streptavidin and any binding partner is isolated by placement in a magnetic field, such as on a magnetic stand.

A range of dNTP/ddNTP ratios are consistent with the disclosure herein. Ratios of 99.9%/0.1%, 99.5%/0.5%, 99%/1%, 98%/2% and alternate ratios are consistent with the disclosure herein. In some cases a relative ratio of 99% deoxy NTP to 1% dideoxy NTP is selected.

In some kits a polymerase is included. Exemplary polymerases are consistent with incorporation of biotin labeled or otherwise labeled ddNTP into an extending nucleic acid chain, and include, among others, Sequenase and Thermosequenase.

In some kits relating to library generation from an RNA template, a reverse-transcriptase is included, such as a reverse transcriptase capable of incorporating biotin labeled or otherwise labeled ddNTP into an extending nucleic acid chain, and include, among others, HIV reverse transcriptase.

In some kits a phage29 polymerase is included.

R_RLP: RNA Rapid Library Prep

The output of RNA Sequencing can provide information on expressed variants and may provide details on alternate splicing and RNA editing. However, critical to RNA sequencing is the ability to quantify small changes in gene expression levels between disease and non-disease states. One problem with absolute quantitation of RNA comes from amplification biases during library preparation. Different sequences have different efficiencies of amplification, so two genes that are actually of equal expression levels in the sample may result in very disparate gene expression levels after biased library amplification. The use of unique single molecule labels for each RNA molecule during library preparation allows normalization of read counts and removes amplification bias artifacts in the data. Described herein are methods producing random 3' fragmentation during the initial steps of library preparation. This allows sequencer reads with unique 3' ends to be normalized to remove amplification bias and produce true quantitative gene expression.

In some embodiments, cDNA may be used as the template source. The same protocol is applied to cDNA template library preparation with the additional step of creating the cDNA. Oligo(dT) priming is used to synthesize the cDNA to restrict the library to messenger RNA with polyA tails or a random primer may be used to synthesize the cDNA to obtain full length transcripts of all RNA species.

The use of the random primers as stochastic labels in the RNA input has the added benefit of normalizing read counts against amplification bias during the process. Some sequences are more amenable to amplification than others. A sample that has two genes of equal abundance (in terms of RNA molecules) may appear to have differential levels of expression after library preparation due to these amplification biases. The use of the synthetic random primers as stochastic labels enables the ability to normalize counts based on the reduction of clonal artifacts. This is of even greater importance when working in smaller genomes or polyA amplified RNA where high coverage is typical.

The use of this assay for single cell gene expression analysis is preferred as it is an amplification protocol at every step. Unlike other methods that require fragmentation through chemical or physical means, fragmentation is performed through polymerization, therefore minimizing the loss from the fragmentation step. For single cell genomics, removing the cDNA generation step may be required. For this, a reverse transcriptase with the capability of incorporating ddNTP/biotin may be employed. HIV reverse transcriptase is capable of this activity.

L_LRP: Long Read Phasing Rapid Library Prep

The human genome consists of 3.2B haploid base pairs. 62% of the genome is made up of highly repetitive and highly polymorphic sequence. In addition, the genome contains LINE and SINE elements, Alu insertions, and other mosaic elements different in each individual. Long reads (>10 kb) are required for full assembly of the non-repeat genome and >90% of the repeat elements in the human genome.

Long reads is obtained through $3^{rd}$ generation sequencing systems such as Pacific Biosciences or nanopore technologies. These technologies are a long way from commercial viability based on the high error rates and the lack of enzyme engineering required to slow down the polymerization of sequencing-by-synthesis (SBS) chemistry or to slow down the migration of a DNA molecule through a nanopore. An alternative strategy for library preparation is to label long, intact DNA molecules for use with current Next Generation Sequencing (NGS) sequencers. This strategy first involves dilution of long DNA molecules and labeling each molecule during library preparation so that short sequencing reads is assigned to the long molecule in the original dilution. A random primer based strategy for this approach is ideal as the labeling step occurs in the first reaction so that all products can then be pooled together for a single workflow for the remainder of the assay (other methods require the full library generation for each dilution of the gDNA template.).

Two main criteria are required for long read sample preparation: 1) the length of the molecule needs to be >10 kb; and, 2) the number of reads per molecule needs to be maximized to insure high quality variant detection. The number of labels, the quality of template and the input amount all vary the ability to achieve long reads and high coverage per molecule.

In some cases, the first step is to dilute out the template into reaction vesicles. This is done in microplates, oil-in-water emulsions or any means with many chambers. For a human genome, it is estimated that at least 1000 molecular labels will be required to accurately assemble and phase the human genome.

Some embodiments include the use of a microdroplet water-in-oil emulsion system. A primer library consisting of over 1544 adapter+label+random primer is introduced to the system as premade water-in-oil emulsion. gDNA template fragmented to 10 kb, 20 kb, or greater, may be introduced to the system with the appropriate mix of enzyme, NTP, ddNTP and reaction buffer. Water-in-oil emulsion droplets containing the diluted long fragment gDNA is generated on the system and merged with the primer library droplets in a 1:1 ratio. One template droplet with one or more long gDNA templates is added to one of the primer DNA stran An exemplary droplet is as follows: 5'-adapter1-8 bp error correcting label-NNNNNNNN-3'.

The labels is designed so that an error in the sequencing of the label will still allow identification of the label for purposes of long read assembly. The primers can bind randomly to the template, be extended, and terminated with a biotin-ddNTP. The emulsion is broken, run across a column to remove oil and surfactant, and the product captured with streptavidin coated magnetic beads. The product can then be selected by size to exclude dimers which may end up as the majority of the reaction.

The effect of input dilution and fragment size on per molecule sequencing coverage is shown in Table 1. As is seen in Table 1, the average coverage per molecule is 7.03 when 80 picograms of DNA are used, while the average coverage per molecule is 0.56 when 1,000 picograms of DNA is used.

TABLE 1

Table 1: The effect of input dilution and fragment size of per molecule sequencing coverage.

| ORGANISM | Human | notes |
|---|---|---|
| SIZE OF haploid GENOME PER CELL(bp) | 3,200,000,000.00 | human genome is 3.2 Gbp long |
| size of Haploid genome (pg) | 3.20 | one Haploid genome is 3.2 pg |
| DNA input (pg) | 1,000.00 | amount of DNA put into the raindance system |
| DNA input after RDT loss | 800.00 | 20% of the 25uL reaction remains in the input vial on the raindance system (80% of starting material in droplets) |
| total # of haploid genomes | 250.00 | this is the total pg in sample divided by the pg per haploid genome |
| total bp in sample | 800,000,000,000.00 | this is the number of haploid genomes per sample multiplied by the size of a human haploid genome in bp |
| avg molecule length | 10,000.00 | input |
| # of molecules per sample | 80,000,000.00 | total bp per sample divided by the average molecule length |
| # of clusters from 1 HiSeq rapid mode flow cell | 1,500,000,000.00 | this is the low end of the HiSeq performance specs |
| # of clusters per molecule | 18.75 | This is the total number of clusters divided by the number of molecules |
| # of paired end reads per molecule | 37.50 | this is the number of clusters multiplied by 2 paired end reads per cluster |
| depth of coverage per molecule | 0.56 | |
| SIZE OF haploid GENOME PER CELL (bp) | 3,200,000,000.00 | human genome is 3.2 Gbp long |
| size of Haploid genome (pg) | 3.20 | one Haploid genome is 12 pg |
| DNA input (pg) | 80.00 | amount of DNA put into the raindance system |
| DNA input after RDT loss | 64.00 | 20% of the 25 uL reaction remains in the input vial on the raindance system (3.0% of starting material in droplets) |
| total # of haploid genomes | 20.00 | this is the total pg in sample divided by the pg per haploid genome |
| total bp in sample | 64,000,000,000.00 | this is the number of haploid genomes per sample multiplied by the size of a human haploid genome in bp |
| avg molecule length | 10,000.00 | input |
| # of molecules per sample | 6,400,000.00 | total bp per sample divided by the average molecule length |
| # of clusters from 1 HiSeq rapid mode flow cell | 1,500,000,000.00 | this is the low end of the HiSeq performance specs |
| # of clusters per molecule | 234.38 | This is the total number of clusters divided by the number of molecules |
| # of paired end reads per molecule | 468.75 | this is the number of clusters multiplied by 2 paired end reads per cluster |
| depth of coverage per molecule | 7.03 | |

Reference Guided Analysis:

In some embodiments, reads is first trimmed of synthetic sequence. The synthetic sequence may include the adapter sequence, the label and the synthetic random primer sequence. Reads may then be aligned and assembled against a reference genome for high quality variant detection. SNVs and complex variation is highlighted and then assigned to a label. Variants within the defined distance of the original molecule size (for example 10 kb) that are on the same label in a haploid region are considered to be in "phase". Unmapped reads are de novo assembled and then recruited to their genomic location by their labels.

De Novo Analysis:

De novo assemblers require 20-30× coverage per haploid locus. This can require extreme dilution to avoid costly oversequencing requirements for a given locus. To minimize sequencer capacity requirements, each genomic location should have as few labels as possible covering each haploid segment. For example, if each label consists of a different 0.01% of the human genome and there are 10,000 labels, one achieves 100% coverage of the genome with only a 30× sequencing depth requirement.

Targeted Sequencing and Assisted De Novo Assembly:

Converting genomic DNA (gDNA) input into the first adapter terminated product has multiple advantages for targeted sequencing. Typical strand displacement amplification has two major drawbacks: 1) chimeric molecules are formed when a copy of the template acts as a primer to a similar sequence on a different chromosome; and, 2) biased amplification tends to be a problem as some regions of the genome are more accessible early on in the reaction and tend to produce branched DNA copies of that region. Terminating the reaction with ddNTP eliminates most of these artifacts. In addition, termination and capture of the gDNA from random priming converts the sample into short, single stranded fragments that are highly accessible to locus specific hybridization and removes the capability of long stretches of gDNA to re-anneal and inhibit polymerase when copying much smaller targeted regions of the genome.

As above, in some cases, the first step is to dilute out the template into reaction vesicles. This is done in microplates, oil-in-water emulsions or any means with many chambers. For a human genome, it is estimated that at least 1000 molecular labels will be required to accurately assemble and phase the human genome.

Some cases involve the use of a microdroplet water-in-oil emulsion system. A primer library consisting of over 1544 adapter+label+random primer is introduced to the system as premade water-in-oil emulsion. gDNA template fragmented to 10 kb, 20 kb, or greater, may be introduced to the system with the appropriate mix of enzyme, NTP, ddNTP and reaction buffer. Water-in-oil emulsion droplets containing the diluted long fragment gDNA is generated on the system and merged with the primer library droplets in a 1:1 ratio. One template droplet with one or more long gDNA templates is added to one of the primer droplets. An exemplary droplet is as follows: 5'-adapter1-8 bp error correcting label-NNNNNNNN-3'.

For targeted sequencing, gDNA may be random primed as described herein. The product is terminated and captured in the same way through the use of ddNTP/biotin and streptavidin coated magnetic beads. During the second reaction, the random sequence may be replaced by 25 base pair (bp) locus-specific sequences. The locus specific sequences bind to their targets and may be extended by a thermo stable polymerase with strand displacing capability. The primer bound closest to the streptavidin bead will displace all of the other primers bound downstream and the beads can then be washed to remove excess NTP, enzyme and primer. The resulting product is released from the bead and sequenced or amplified through the use of the adapter sequences and PCR. A representative oligo is as follows: 3'-adapter1-NNNNNNNN-insert-Locus Specific sequence (25 bp)-adapter2-5'. In some exemplary targeted sequencing library generation protocols, the second reaction random sequence oligo is replaced by a two, three, four or more than four oligos that specifically anneal to a target locus of interest. In some exemplary targeted sequencing library generation protocols, the second reaction random sequence oligo is replaced by a pair of oligos that that specifically anneal to a target locus of interest. In some cases the oligos bind to overlapping regions of the target locus as represented in the first strand library. In some cases the pair of oligos bind at adjacent regions of the target locus or first strand library, for example 1, 2, 3, 4, 5, 6, 7, 8, 9, 10, 11, 12, 13, 14, 15, or more than 15 bases apart from one another. In some cases the oligos are each independently 12, 13, 14, 15, 16, 17, 18, 19, 20, 21, 22, 23, 24, 25, 26, 27, 28, 29, 30, 31, 32, 33, 34, 35, or greater than 35 bases. In exemplary embodiments two second strand oligos are used, each 25 bases long, nonoverlapping and separated by about 10-20 bases in their annealing positions.

As an alternative or in combination, for targeted sequencing, the first random primer may be replaced by one or by a pair of oligos that that specifically anneal to a target locus of interest. In some cases the oligo or oligos bind to overlapping regions of the target locus. The product is terminated and captured in the same way through the use of ddNTP/biotin and streptavidin coated magnetic beads. During the second reaction, the first strand library bound to streptavidin beads is primed with a tagged random oligo population as in the protocols described in the previous sections. Bound oligos are extended as above using a strand-displacing DNA polymerase, and the double stranded library products generated thereby are amplified and sequenced, and the sequence thereby generated is assessed to cull duplicate reads representing the same library molecule, as described herein.

In some embodiments targeted library generation is effected through hemi-specific PCR during the locus specific priming step. The product from the first random priming reaction has the first adapter on one end. A primer complimentary to this adapter sequence is used along with the locus specific primer for low cycle PCR. The product is directly sequenced or amplified further through PCR with primers corresponding to each of the adapter sequences.

In some embodiments a targeted sequencing strategy may produce sequencer libraries with a chimeric read structure, as illustrated in FIG. 16A-16B. A chimeric read can start with a known synthetic sequence to identify the genomic coordinate of the read. The remainder of the read may include sample derived DNA of unknown sequence. Primers is designed every 100-200 bp across the target genomic sequence. The primers that span a given target are called a primer "set" and the primer sets is then binned together, trimmed from the reads and the remaining sequence self-assembled across the sequence bins. In this way, de novo haplotypes assembled across the target locus may be produced without the use of a reference alignment.

In an embodiment, the pipeline starts with primers tiled across the target (100 bp), the adapters are trimmer, optionally the sample barcode is identified, the genomic coordinate (TAG) is identified, duplicate reads are removed, the tags are binned and trimmed, the de novo consensus sequence is obtained, off-target reads are removes, perfect match haplotypes are looked up, and structural variation is determined, resulting in a consensus sequence that spans the full target. This simple 60-minute protocol is easily automated, reduces dropout, requires no ligation, physical fragmentation or end repair, removes clonal errors, allows for assisted de novo assembly and can detect complex variation. This is achieved with a dramatically reduced cost.

In some cases, a nucleic acid sample is obtained and fragmented. Fragments are size selected to have a minimum size of 10-100, 10-150, 10-200, 1-300, 10-350, 10-400, 10-500, 10-600, 10-700, 10-800, 10-900, or 10-1000, kilobases. Size-selected fragments are diluted to not more than 10, 20, 30, 40, 50, 60, 70, 80, 90, 100, 110, 120, 130, 140, 150, 160, 170, 180, 190, 200, 300, 400, or 500 fragments per aliquot and distributed into separate reaction tubes. Each aliquoted sample is contacted with a population of first strand synthesis oligonucleotides. The first strand oligonucleotides each comprise a full-length sequence adapter 5' of a random oligomer (such as an 8-mer) followed by a 3'-OH from which template directed extension occurs. The random oligomer (such as an 8-mer) is unique to a single oligo, although a small degree of redundancy is easily tolerated by the methods disclosed herein, and even a large degree of redundancy is accommodated. In some cases, the first strand synthesis oligonucleotides are designed to form hairpin structures to diminish the formation of primer-dimers. In some cases, the random oligomer (such as an 8-mer) population of the first round synthesis oligos represents all possible random oligomers of a certain length (such as an 8-mer), but the relative abundance of each random oligomer of a certain length (such as an 8-mer) is biased to match the relative abundance of GC vs AT base pairs in the human genome. An amount of the population (such as 4 uL) is added to the sample. Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a relative ratio of 99% deoxy NTP to 1% di-deoxy NTP. An amount of the buffer/NTP composition (such as 8 uL) is added to the sample. The mixture is then diluted to a certain volume (such as 19 uL) and heated, during which time the nucleic acid is caused to 'melt' into single-strands unbound by hydrogen bonding between complementary bases. The mixture is then cooled to allow for reverse-complementary base-pairing between the first strand synthesis oligonucleotides and the nucleic acid sample. In some cases, it is observed that some oligonucleotides demonstrate complete reverse-complementarity between their random oligomer of a certain length (such as an 8-mer) and the nucleic acid sample sequence to which each binds. It is also observed that some oligonucleotides bind to regions that are incompletely reverse-complementary to the random oligomer of a certain length (such as an 8-mer). The failure to base pair with complete reverse complementarity is not detrimental to subsequent steps in the process. In some cases, a polymerase (such as SEQUENASE) having strand displacement activity and able to incorporate biotin-ddNTP is added to the composition. The composition is heated and allowed to continue for a period of time (for example, 30 minutes at room temperature). Extension from the 3'-OH of the first strand synthesis oligonucleotides is observed, resulting in sequence reverse complementary to the template at the annealing site of each annealed oligo being incorporated at the 3' end of each annealed oligo. Extension continues until a biotin-labeled ddNTP molecule is incorporated, at which point extension terminates. In some cases, when a 99%/1% ratio of dNTP to biotin-ddNTP complexes is used, 50% of the first strand oligos on which extension occurs demonstrate an extension of over 50 bases prior to the incorporation of an biotin-ddNTP molecule. The composition is then heated for a period of time (for example, 98° C. for 5 minutes) and the sample is subjected to purification and second strand synthesis. In some cases, the resulting library is then subjected to size selection via gel electrophoresis.

In some cases, a blood sample is obtained from a pregnant mammal, such as a pregnant woman. This blood sample contains cell-free fetal DNA circulating freely in the maternal bloodstream in fragments of approximately 200 bp in size. In some cases, the cell-free fetal DNA is separated from the maternal plasma by the addition of formaldehyde to stabilize intact maternal cells, centrifugation, isolation and purification of the supernatant, and size selection via gel electrophoresis. The purified cell-free fetal DNA is then used as the template nucleic acid in the methods described herein. Analysis of Targeted Sequencing Products Through "Assisted De Novo Assembly".

The first 25 bp of each read corresponds to the synthetic locus specific primer sequence. As the locus specific primers are tiled across the region of interest, the reads is binned within primer sets targeting a specific contiguous locus. The reads from the primer sets will therefore be overlapping and is "self-assembled" by comparing them to each other. Off target reads or mispriming will not form a consensus sequence with the remaining reads from the primer set. These reads will be discarded from the analysis or in the case of multiple primers in a set showing the same off target location will be analyzed as complex variation in a separate pipeline as this indicates a complex rearrangement in the target region. The distance between the primers may also indicate complex variation as a large insertion or deletion will change the empirically observed distance between the primers, making that distance larger or smaller than expected.

Further Embodiments

Aspects of the current disclosure describe methods and compositions for generating a population of non-identical, tagged nucleic acid molecules each comprising a subset of sequence from a target nucleic acid sample. The target nucleic acid sample may be obtained from any biological or environmental source, including plant, animal (including human), bacteria, fungi, or algae. Any suitable biological sample is used for the target nucleic acid. Convenient suitable samples include whole blood, tissue, semen, saliva, tears, urine, fecal material, sweat, buccal, skin, and hair. In some embodiments, the target nucleic acid is obtained from 50-500 cells. In some embodiments, the target nucleic acid is obtained from 50-400, 50-350, 50-300, 100-300, 150-300, 200-300, or 200-250 cells.

In an embodiment, the method may comprise obtaining a first nucleic acid molecule comprising a first molecular tag sequence and a first target sequence having a first length from a target nucleic acid sample. The first nucleic acid molecule may be of varying length. In some embodiments, the length of the first nucleic acid molecule corresponds to the optimum length for a specific sequencing platform. Optimum lengths for specific sequencing platforms may include up to 400 nucleotide bases for ion semiconductor (e.g., ION TORRENT, Life Technologies, Carlsbad, Calif.), 700 nucleotide bases for pyrosequencing (e.g., GS JUNIOR+, 454 Life Sciences, Branford, Conn.), and 50 to 300 nucleotide bases for sequencing by synthesis (SBS) (e.g., MISEQ, Illumina, San Diego, Calif.). In some embodiments, the first nucleic acid molecule may be 50-1000, 100-1000, 200-1000, 300-1000, 300-900, 300-800, 300-700, 300-600, 300-500, or 400-500 nucleotide bases. In some embodiments, the first nucleic acid molecule may be 50, 62.5, 125, 250, 500, or 1000 nucleotide bases.

In some embodiments, the first nucleic acid molecule comprises a molecular ligand. In some embodiments, this molecular ligand comprises biotin or any biotin derivatives or analogs.

In some embodiments, the molecular tag sequence may be 6, 7, 8, 9, or 10 nucleotide bases long. In some embodiments, the molecular tag is 8 nucleotide bases long. In an embodiment, the molecular tag comprises a random nucleotide sequence. In some embodiments, the random nucleotide sequence is synthesized in a semi-random fashion to account for variable content in a target nucleic acid sample. The random nucleotide sequence may be selected to reflect representative "randomness" ordered against the windows of guanine-cytosine (GC) content in the genome from 1% to 100% GC and synthesized and pooled in ratios relative to the content of the genome at each GC %.

In some embodiments, the first nucleic acid molecule may be obtained through contacting a first primer comprising a first random oligonucleotide sequence to a target nucleic acid sample. In some embodiments, contacting a first primer comprises annealing a first primer to a nucleic acid of said target nucleic acid sample. Annealing may result in complete hybridization or incomplete hybridization. In a further embodiment, a second nucleic acid is generated through contacting a second primer comprising a second random oligonucleotide sequence to a first nucleic acid molecule. This method may comprise annealing an oligonucleotide comprising a second molecular tag sequence to a first nucleic acid molecule and extending the oligonucleotide to obtain a first double-stranded nucleic acid molecule comprising a first molecular tag sequence, a first target sequence having a first length, and a second molecular tag sequence. In some embodiments, the second nucleic acid molecule may be generated through contacting a second primer comprising a locus-specific oligonucleotide sequence and a second molecular tag sequence to a first nucleic acid molecule. This locus-specific oligonucleotide sequence may be targeted to exons, regions containing single-nucleotide polymorphisms, or other regions of interest. In some cases, the template is in excess to the locus-specific oligonucleotide sequence, allowing normalization of the library prior to PCR.

The methods described herein may further comprise obtaining a second double-stranded nucleic acid molecule comprising a third molecular tag sequence, a second target sequence having a second length, and a fourth molecular tag sequence, and discarding the second double-stranded nucleic acid molecule if the third molecular tag sequence is identical to the first molecular tag sequence, the fourth molecular tag sequence is identical to the second molecular tag sequence, the second target sequence is identical to the first target sequence, and the second target sequence length is identical to the first target sequence length. In some embodiments, the second double-stranded molecule may be retained if the third molecular tag sequence is different from the first molecular tag sequence, the fourth molecular tag sequence is different from the second molecular tag sequence, the second target sequence is different from the first target sequence; or the second target sequence length is different from the first target sequence length, the result being generating a population of non-identical, tagged nucleic acid molecules each comprising a subset of sequence from a target nucleic acid sample In some embodiments, the first nucleic acid comprises an adapter sequence positioned 5' to said first random oligonucleotide sequence. In some embodiments, this adapter sequence is added to facilitate amplification and/or sequencing for a specific sequencing platform. Sequencing platforms include ion semiconductor (e.g., ION TORRENT, Life Technologies, Carlsbad, Calif.), pyrosequencing (e.g., GS JUNIOR+, 454 Life Sciences, Branford, Conn.), and sequencing by synthesis (SBS) (e.g., MISEQ, Illumina, San Diego, Calif.). Exemplary adapter sequences include SEQ ID NOs: 1 and 2.

In some cases, library molecules are circularized prior to sequencing. Library molecule circularization is effected, for example, by providing a 'bridge oligo' or 'splint oligo' comprising sequence reverse-complementary to adapter sequences SEQ ID NO: 1 and SEQ ID NO: 2, or other adapter sequences, such that the 5' end and 3' end of a single-stranded library product molecule are simultaneously bound by the bridge oligo. In some cases the bridge oligo holds the 5' and 3' ends of the single-stranded library molecule in proximity through base-pairing hydrogen bond interactions, such that the 5' and 3' ends of a molecule may be joined upon addition of a ligase to form a circularized library molecule. Molecules may be circularized through any number of molecular techniques, such as ligation, cre-lox based fusion, nick-repair-based techniques or otherwise to form a single circular molecule. In some cases, libraries are then treated with exonuclease to remove bridge oligos.

Circularized molecules are then sequenced through one of a number of sequencing techniques known in the art, such as rolling circle amplification/sequencing to obtain sequence information.

In some cases, the first nucleic acid and the first primer may be contacted to a nucleic acid polymerase and a nucleotide triphosphate. Nucleic acid polymerases include DNA polymerases from the families A, B, C, D, X, Y, and RT. In some embodiments, the nucleic acid polymerase has strand displacement activity. In some embodiments, the nucleic acid polymerase lacks strand displacement activity. Nucleotide triphosphates can include deoxyribonucleoside triphosphates such as dATP, dCTP, dITP, dUTP, dGTP, and dTTP, and dideoxyribonucleoside triphosphates (ddNTPs) such as ddATP, ddCTP, ddGTP, ddITP, and ddTTP. In some embodiments, the nucleotide triphosphate is selected by the nucleic acid polymerase from a pool comprising deoxynucleotide triphosphates and dideoxynucleotide triphosphates. In some embodiments, this pool may comprise dideoxynucleotide triphosphates in an amount ranging from 0.01%-5.0%, 0.01%-4.0%, 0.01%-3.0%, 0.01%-2.0%, 0.02%-2.0%, 0.03%-2.0%, 0.04%-2.0%, 0.05%-2.0%, 0.06%-2.0%, 0.07%-2.0%, 0.08%-2.0%, 0.09%-2.0%, or 0.1%-2.0%. In some embodiments, the pool may comprise dideoxynucleotide triphosphates in an amount of 0.05, 0.1%, 0.2%, 0.4%, 0.8%, or 1.0%. In some embodiments, the nucleotide triphosphate is selected by the nucleic acid polymerase from a pool comprising dATP, dCTP, dGTP, and dTTP, with one of the four deoxynucleotide triphosphates at a significantly lower concentration than the other three, or two of the four deoxynucleotide triphosphates at a significantly lower concentration than the other two. In some cases, the nucleotide triphosphate is selected by the nucleic acid polymerase from a pool of deoxynucleotide triphosphates and modified nucleotides, such as 2,6 Diaminopurine and 2-thiothymidine (or uracil, without a methyl group at 5 position). In some cases the modified nucleotides comprise a 'semi-compatible' nucleotide base pair. In some cases semi-compatible nucleotide base pairs comprise modified nucleotides selected such that they are able to base pair with a naturally occurring nucleotide base or bases that pair with their naturally occurring relative, but are unable to base pair with an analogue of their naturally occurring base pair partner. For example, the Adenine analogue 2,6-diaminopurine is able to base pair with Thymidine, and the Thymidine analogue 2-thiothymidine is able to base pair with Adenine, but the semi-compatible pair of 2,6-diaminopurine and 2-thiothymidine cannot base pair with one another. This, the Adenine analogue 2,6-diaminopurine and the Thymidine analogue 2-thiothymidine constitute a semi-compatible base pair. A composition comprising the nucleotide triphosphates dGTP and dCTP (a complementary or natural pair), and the semi-complementary pair deoxy-2,6-diaminopurineTP and deoxy-2-thiothymidineTP, thus, supports extension from a 3'OH position of template-directed nucleic acid synthesis.

Other modified base pairings are contemplated, such as alternative A:T pairs and alternative G:C pairs.

A benefit of such semi-compatible modified bases is that a nucleic acid template incorporating these modified bases cannot serve as a template for synthesis if the dNTP pool from which nucleic acids are drawn includes a sufficient concentration of these bases. Thus, nucleic acids incorporating these bases are confidently templated by an original nucleic acid sample rather than being templated by other synthesized nucleic acids. This characteristic allows the synthesis of multiple copies of a sample nucleic acid without the risk that a base incorporation mismatch error early in the nucleic acid synthesis reaction will be propagated in later templates. However, by replacing the dNTP pool with a pool consisting of or comprising naturally occurring dNTP of the type of base for which the analogue is a replacement, nucleic acids comprising all four naturally occurring bases is generated from templates incorporating base pair analogues.

In some cases, at least one of the modified nucleotides is labeled. In some cases at least one of the modified nucleotides is digoxigenin(DIG)-, biotin-, fluorescein-, or tetramethylrhodamine-labeled. In some cases, the template is fragmented into fragments of a specific length prior to contacting the first nucleic acid and the first primer. In some cases one or more nucleotide analogs are used, such as nucleotide analogs that are sensitive to endonuclease treatment in combination with an endonuclease to achieve chain termination. In some cases chain termination is achieved through manipulation of dNTP concentration In an embodiment, a pool comprising deoxynucleotide triphosphates and dideoxynucleotide triphosphates comprises at least one dideoxynucleotide triphosphate bound to a molecular ligand. In some embodiments, this molecular ligand comprises biotin. In some embodiments, the methods comprise contacting a molecule comprising an oligonucleotide comprising a second molecular tag sequence annealed to said first nucleic acid molecule to a ligand binding agent. In some embodiments, this ligand binding agent is avidin or streptavidin. In some cases, the ligand binding agent is a high-affinity antibody to DIG, biotin, fluorescein, or tetramethylrhodamine.

In some embodiments, at least one of the nucleic acids described herein is a deoxyribonucleic acid. In a further embodiment, a deoxyribonucleic acid is fragmented into fragments greater than 10 kilobases. Fragmentation may be accomplished in a number of ways, including mechanical shearing or enzymatic digestion. In some embodiments, at least one of the nucleic acids described herein is a ribonucleic acid. In some embodiments, a target nucleic acid sample is ribonucleic acid. In a further embodiment, a first nucleic acid molecule is a complementary deoxyribonucleic acid (cDNA) molecule generated from a ribonucleic acid. In some embodiments, the nucleic acid polymerase that generated the cDNA is an RNA-dependent DNA polymerase. In some embodiments, the cDNA is generated through contacting a first primer comprising an oligo(dT) sequence to a target nucleic acid sample.

In a further embodiment, all sequences from a given contig having the same molecular tag are assigned to a specific homologous chromosome.

Also described herein are compositions comprising a first nucleic acid molecule comprising a first molecular tag sequence and a first target sequence having a first length, and an oligonucleotide comprising a second molecular tag sequence. In some embodiments, the first nucleic acid molecule comprises a 3' deoxynucleotide. In some embodiments, the 3' deoxynucleotide is a dideoxynucleotide. In some embodiments, the first nucleic acid comprises an adapter sequence positioned 5' to the first molecular tag sequence. This adapter sequence may be added to facilitate amplification and/or sequencing for a specific sequencing platform, such as ion semiconductor (e.g., ION TORRENT, Life Technologies, Carlsbad, Calif.), pyrosequencing (e.g., GS JUNIOR+, 454 Life Sciences, Branford, Conn.), or sequencing by synthesis (SBS) (e.g., MISEQ, Illumina, San Diego, Calif.). Exemplary adapter sequences include 5' AAT GAT ACG GCG ACC ACC GA 3' (SEQ ID NO: 1), and 5' CAA GCA GAA GAC GGC ATA CGA GAT 3' (SEQ ID NO: 2). Adapters compatible with Illumina, 454, Ion Torrent and other known sequencing technologies are contemplated herein.

In some embodiments, the composition comprises a first nucleic acid molecule comprising a molecular ligand. In some embodiments, this molecular ligand comprises biotin. In some embodiments, the composition comprises a ligand binding agent. In some embodiments, this ligand binding agent is avidin or streptavidin. The compositions described herein may also comprise a ligand-ligand binding agent wash buffer. In some embodiments, the compositions described herein comprise a biotin wash buffer.

The compositions described herein may also comprise unincorporated nucleotides. In some embodiments, the unincorporated nucleotides are unincorporated deoxynucleotides. In some embodiments, the unincorporated nucleotides are dideoxynucleotides.

In some embodiments, the compositions described herein comprise a first nucleic acid molecule hybridized to an oligonucleotide comprising a second molecular tag sequence. The first nucleic acid molecule may be completely hybridized to the second molecular tag sequence of the oligonucleotide, or the first nucleic acid molecule may be incompletely hybridized to the second molecular tag sequence of the oligonucleotide.

Further described herein are compositions comprising a population of nucleic acid molecules, wherein each molecule independently comprises a first strand comprising a first adapter sequence, a molecular tag sequence, and an independent target sequence, and wherein each independent target sequence comprises a subset of a sample nucleic acid sequence, and wherein at least a first molecule of the population comprises an independent target sequence comprising a first subset of the sample nucleic acid sequence, and wherein at least a second molecule of the population comprises an independent target sequence that comprises a second subset of the sample nucleic acid sequence. In some embodiments, the adapter of each first strand of the population is identical. In some embodiments, the molecular tag sequence of each molecule of the population comprises at least six nucleotide bases. In some embodiments, a first member of the population and a second member of the population comprise non-identical molecular tag sequences. In some embodiments, each first strand comprises a 3'-deoxynucleotide base at its 3' end. In some embodiments, each first strand may comprise a molecular ligand at its 5' end or each first strand may comprise a molecular ligand attached at a non-terminal position. Additionally, each first strand may comprise a molecular ligand at its 3' end. In some embodiments, the molecular ligand is biotin.

In some embodiments, the compositions described herein comprise a population of nucleic acid molecules, wherein each molecule of the population comprises a second strand comprising a second adapter sequence and a second molecular tag sequence. In further embodiments, the second strand of at least one molecule of the population may be annealed to a first strand via at least partial base pairing of a second molecular tag sequence of the second strand to the independent target sequence of the first strand. In some embodiments, the adapter of each second strand of the population may be identical. In some embodiments, at least one molecule of the population is bound to a molecular ligand binder. In some embodiments, the molecular ligand binder comprises avidin or streptavidin.

The compositions described herein may also comprise unincorporated nucleic acid triphosphates. In some embodiments, the compositions described herein may comprise molecular ligand binder wash buffer, and/or polymerase extension buffer, and/or nucleic acid polymerase. In some embodiments, the nucleic acid polymerase possess nucleic acid helicase activity. In some embodiments, the compositions described herein comprise nucleic acid polymerase possessing nucleic acid strand displacement activity. In some embodiments, the compositions described herein comprise the sequences compatible with Illumina, Ion torrent or 454 sequencing technology. In some embodiments, the compositions described herein comprise the sequences recited in SEQ ID NO: 1 and SEQ ID NO: 2.

Sequence information obtained herein is used in some cases to quantify nucleic acid accumulation levels. A library is generated and sequenced as disclosed herein. Duplicate reads are excluded so that only uniquely tagged reads are included. Unique read sequences are mapped to a genomic sequence or to a cDNA library or transcriptome sequence, such as a transcriptome for a given cell type or treatment or a larger transcriptome set up to and including an entire transcriptome set for an organism. The number of unique library sequence reads mapping to a target region is counted and is used to represent the abundance of that sequence in the sample. In some embodiments uniquely tagged sequence reads each map to a single site in the sample sequence. In some cases, uniquely tagged sequence reads map to a plurality of sites throughout a genome, such as transposon insertion sites or repetitive element sites. Accordingly, in some cases the number of library molecules mapping to a transcriptome 'locus' or transcript corresponds to the level of accumulation of that transcript in the sample from which the library is generated. The number of library molecules mapping to a repetitive element, relative to the number of library molecules that map to a given unique region of the genome, is indicative of the relative abundance of the repetitive element in the sample. Thus, disclosed herein is a method of quantifying the relative abundance of a nucleic acid molecule sequence in a sample comprising the steps of generating a sequence library comprising uniquely tagged library fragments and mapping the nucleic acid molecule sequence onto the library, such as the frequency of occurrence of the nucleic acid molecule sequence in the library corresponds to the abundance of the nucleic acid molecule sequence in the sample from which the library is generated. In some cases the frequency of occurrence of the nucleic acid molecule sequence in the library is assessed relative to the frequency of occurrence of a second nucleic acid molecule sequence in the library, said second nucleic acid sequence corresponding to a locus or transcript of known abundance in a transcriptome or known copy number per genome of a genomic sample.

Methods of preparing nucleic acids in a sample for sequencing using any of the compositions are described herein. In some embodiments, the samples is obtained from a cell, a tissue, or a partial of an organism. Non-limiting examples of organisms can include, human, plants, bacteria, virus, protozoans, eukaryotes, and prokaryotes. As an illustrating example, the sample is a human genome comprising human genomic nucleic acids. The sample is used to prepare a nucleic acid library. The library is sequenced.

Preparation of nucleic acid library for sequencing is achieved using methods as described herein or methods known in the art. In some embodiments, the nucleic acids are obtained from a human genome. The human genome nucleic acids is amplified in a reaction mixture X. In some embodiments, the reaction mixture X can comprise DNA, at least one primer, a buffer, a deoxynucleotide mixture, an enzyme, and nuclease-free water. The reaction mixture X is prepared in an Eppendorf tube. Preferably, the reaction mixture X is prepared in an Eppendorf DNA LoBind microcentrifuge tube. In some cases, the DNA is a human DNA. The final concentration of DNA in the reaction mixture X is about 0.1 ng, 0.2 ng, 0.3 ng, 0.4 ng, 0.5 ng, 0.6 ng, 0.7 ng, 0.8 ng, 0.9 ng, 1.0 ng, 1.2 ng, 1.4 ng, 1.5 ng, 1.8 ng, 2.0 ng, or more. The final concentration of DNA in the reaction mixture X is about 0.1 ng, 0.2 ng, 0.3 ng, 0.4 ng, 0.5 ng, 0.6 ng, 0.7 ng, 0.8 ng, 0.9 ng, 1.0 ng, 1.2 ng, 1.4 ng, 1.5 ng, 1.8 ng, 2.0 ng, or less. The final concentration of DNA in the reaction mixture X is between about 0.1 to about 2.0 ng, between about 0.2 ng to about 1.2 ng, between about 0.5 ng to about 0.8 ng, or between about 1.0 ng to about 1.5 ng.

In some cases, the reaction mixture X comprises only one primer, for example, Primer A. The final concentration of Primer A in the total reaction mixture is about 10 µM, 20 µM, 30 µM, 40 µM, about 50 µM, about 100 µM, about 150 µM, about 200 µM, or more. The final concentration of Primer A in the total reaction mixture X is about 10 µM, 20 µM, 30 µM, 40 µM, about 50 µM, about 100 µM, about 150 µM, about 200 µM, or less. The final concentration of Primer A in the total reaction mixture X is between about 10 µM to about 200 µM, between about 30 µM to about 80 µM, between about 50 µM to about 100 µM, or between about 40 µM, to about 150 µM.

In some cases, the reaction mixture X comprises a buffer such as a Thermo Sequenase Buffer. Typically, the final concentration of buffer in the reaction mixture X is about 10% of the original concentration of the buffer. For example, depending on the final volume of the reaction mixture X, the amount of buffer to be added is less than, more than or about 1 µl, about 2 µl, about 2.5 µl, about 3 µl, about 4 µl, about 5 µl, about 10 µl.

In some cases, the reaction mixture X comprises a plurality of deoxynucleotides. The deoxynucleotides are one or more of dATP, dTTP, dGTP, dCTP, ddATP, ddTTP, ddGTP and ddCTP. The final concentration of deoxynucleotides in the reaction mixture X is about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or more. The final concentration of deoxynucleotides in the reaction mixture X is about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or less.

In some cases, the reaction mixture X comprises an enzyme such as a polymerase. For example, the enzyme is a Thermo Sequenase in some cases. The final concentration of the polymerase is about 0.01 µM, about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or more. The final concentration of the polymerase is about 0.01 µM, about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or less. The final concentration of the polymerase is between to about 2.0 µM, between about 0.1 µM to about 1.0 µM, between about 0.5 µM to about 1.5 µM, or between about 0.8 µM to about 1.8 µM.

Typically, a volume of nuclease-free water is added to the reaction mixture X to achieve a desired final volume. The final volume of the reaction mixture is about 10 µl, about about 25 µl, about 30 about 40 µl, about 50 µl, or about 100 µl. Depending on the final volume of reaction mixture X, the amount of nuclease-free water is about 0.1 µl, about 0.5 µl, about 0.8 µl, about 1.0 µl, about 2 µl, about 5 µl, about 10 µl, about 15 µl, about 20 µl, about 25 µl, about 30 µl, about 40 µl, about 50 µl, about 80 µl, about 90 µl, about 95 µl, or more. The amount of nuclease-free water is about 0.1 µl, about 0.5 µl, about 0.8 µl, about 1.0 µl, about 2 µl, about 5 µl, about 10 µl, about 15 µl, about 20 µl, about 25 µl, about 30 about 40 µl, about 50 about 80 µl, about 90 µl, about 95 µl, or less. The amount of nuclease-free water is between about 0.1 µl to about 95 between about 1.0 µl to about 10 between about 5 µl to about 50 or between about 20 µl to about 80 µl.

In general, the reaction mixture X is incubated at a temperature (Tm) for a period of time long enough to denature the DNA. The Tm is about 80° C., about 85° C., about 90° C., about 91° C., about 92° C., about 93° C., about 94° C., about 95° C., about 96° C., about 97° C., about 98° C., about 99° C., or more. The reaction mixture X is incubated at Tm for more than, less than, or about 5 seconds, about 10 seconds, about 15 seconds, about 20 seconds, about 30 seconds, about 1 minute, about 2 minutes, about 3 minutes, about 4 minute, about 5 minutes, about 6 minutes, about 7 minutes, about 8 minutes, about 9 minutes, about 10 minutes. For example, the reaction mixture X is incubated at 95° C. for about 3 minutes. After denaturing, the temperature of the reaction mixture X is lowered by placing the tube on ice. For example, the tube is placed on ice for more than, less than, or about 5 seconds, about 10 seconds, about 15 seconds, about 20 seconds, about 30 seconds, about 5 seconds, about 10 seconds, about 15 seconds, about 20 seconds, about 30 seconds, about 1 minute, about 2 minutes, about 3 minutes, about 4 minute, about 5 minutes, about 6 minutes, about 7 minutes, about 8 minutes, about 9 minutes, about 10 minutes. Preferably, the polymerase, for example, Thermo Sequenase, is added to the reaction, and mixed gently. In general, the reaction mixture X is transferred to a thermal cycler, and proceed with a problem on the instrument described herein.

The thermal cycler performs a program comprising (1) maintaining the temperature at about a low temperature for a period of time, (2) increasing the temperature to a DNA annealing temperature, (3) maintaining at the annealing temperature for a period of time, (4) increasing the temperature to a denature temperature for a period of time, repeating (1) to (4) for at least 9 times, and hold at 8° C., 4° C., or lower, or frozen at −20° C. for storage. The low temperature of (1) is maintained at about 10° C., about 12° C., about 14° C., about 16° C., about 18° C., or about 20° C. The low temperature of (1) is maintained for about 5 seconds, about 10 seconds, about 15 seconds, about 20 seconds, about 30 seconds, about 1 minute, about 2 minutes, about 3 minutes, about 4 minute, about 5 minutes, about 6 minutes, about 7 minutes, about 8 minutes, about 9 minutes, about 10 minutes, about 15 minutes, or about 20 minutes. As an alternative, the thermal cycler can maintain the temperature at about 16° C. for about 3 minutes. In some embodiments, the temperature from (1) to (2) is increased slowly, such that the temperature is ramp out by a small increment of temperature at about 0.1° C./second. The temperature of (2) is about 45° C., about 50° C., about 55° C., about 60° C., about 65° C., about 68° C., about 70° C., or more. In some cases, the temperature of (2) is slowly ramped up to about 60° C. by 0.1° C./second. In some cases, the temperature of (2) is the same as the temperature of (3). In some cases, the temperature of (2) is further increased to reach the temperature of (3). The temperature of (3) is maintained for about 5 seconds, about 10 seconds, about 15 seconds, about 20 seconds, about 30 seconds, about 1 minute, about 2 minutes, about 3 minutes, about 4 minute, about 5 minutes, about 6 minutes, about 7 minutes, about 8 minutes, about 9 minutes, about 10 minutes, about 15 minutes, or about 20 minutes. In some embodiments, the temperature of (3) is maintained for about 10 minutes. As an example, the temperature of (4) is about 95° C., and maintained for about 10 seconds, 20 seconds, 30 seconds, 45 seconds, 60 seconds, 1 minute, 2 minutes, or longer.

In some embodiments, all reaction components in the reaction mixture X, except the primer, are combined and loaded onto a relevant partitioning device. After the reaction tis partitioned and combined with barcoded primers, the reaction mixture is transferred to a thermal cycler, heat denatured at 95° C. for 2 minutes, and subsequently thermocycled according to the program described herein. In some embodiments, the product is temporarily stored at 4° C. or on ice, or frozen at −20° C. for long term storage. In some embodiments, shortly before continuing with the next step, the stored product is heated at about 98° C. for about 3 minutes, then transferred to temporarily store on ice.

In some embodiments, the DNA product of the reaction mixture X described above is captured with magnetic beads. This is achieved by preparing the Capture Beads prior to adding the product as described above. To begin with, the Capture Bead tube is shook thoroughly to resuspend the beads and transfer about 40 µl of the beads to a new 0.5 mL Eppendorf DNA LoBind tube. In some cases, the volume of beads is about 10 µl, about 20 µl, about 30 µl, about 50 µl, about 100 µl, or more. The tube is placed on a magnetic stand for about 0.5-1 minutes to allow the solution to clear up. The supernatant is pipetted and discarded. The tube is removed from the magnetic stand. A volume of about 200 µl of HS Buffer is added to the beads. The components are mixed gently by pipetting the sample up and down, before returning to the magnetic stand. The sample is kept on the magnetic stand for about 0.5-1 minutes to allow the solution to clear up. The supernatant is removed and discarded by gently pipetting it out of the tube. The tube is then removed from the magnetic stand and the beads are resuspended in 40 µl of HS Buffer. The tube is temporarily left on the laboratory bench at room temperature. The DNA product from the reaction mixture described above is added to be Capture Beads prepared as described herein, and incubated at room temperature for about 20 minutes. In some case, the sample comprising the DNA and Capture Beads is incubated at room temperature for about 10 minutes, about 15 minutes, about 20 minutes, about 30 minutes, or more. The DNA product and the Capture Beads is mixed by pipetting up and down for about 5 minutes, about 10 minutes, about 15 minutes, about 20 minutes, about 30 minutes, or more. The tube comprising the mixture of DNA product and Capture Beads is placed on the magnetic stand and wait for the solution to clear up. The supernatant is removed by carefully pipetting it out of the tube. The tube can then be removed from the magnetic stand and the beads is resuspended in 200 µl of Bead Wash Buffer, and returned to the magnetic stand for a period of time to allow the solution to clear up. The supernatant is discarded. The washing is repeated for at least 2 additional times, and the remaining liquid after the final wash is carefully removed.

The washed Capture Beads and DNA product described above is added to a mixture of reagents to generate a reaction mixture Y. The reagent can comprise a Sequenase buffer, a plurality of deoxynucleotides, at least one primer, an enzyme, and nuclease-Free water.

In some cases, the reaction mixture Y comprises only one primer, for example, Primer B. The final concentration of Primer A in the total reaction mixture Y is about 10 µM, 20 µM, 30 µM, 40 µM, about 50 µM, about 100 µM, about 150 µM, about 200 µM, or more. The final concentration of Primer B in the total reaction mixture Y is about 10 µM, 20 µM, 30 µM, 40 µM, about 50 µM, about 100 µM, about 150 µM, about 200 µM, or less. The final concentration of Primer B in the total reaction mixture Y is between about 10 µM to about 200 µM, between about 30 µM to about 80 µM, between about 50 µM to about 100 µM, or between about 40 µM, to about 150 µM.

In some cases, the reaction mixture Y comprises a Sequenase Buffer. Typically, the final concentration of buffer in the reaction mixture Y is about 10% of the original concentration of the buffer. In some cases, the final concentration of buffer in the reaction mixture Y is about 5%, about 10%, about 15%, about 20%, about 30% or less, of the original concentration of the buffer. For example, depending on the final volume of the reaction mixture Y, the amount of buffer to be added is less than, more than or about 1 µl, about 2 µl, about 2.5 µl, about 3 µl, about 4 µl, about 5 µl, about 10 µl.

In some cases, the reaction mixture Y comprises a plurality of deoxynucleotides. The deoxynucleotides is dATP, dTTP, dGTP, dCTP, ddATP, ddTTP, ddGTP and ddCTP, The final concentration of deoxynucleotides in the reaction mixture Y is about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or more. The final concentration of deoxynucleotides in the reaction mixture Y is about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or less.

In some cases, the reaction mixture Y comprises an enzyme. The enzyme is a polymerase. For example, the enzyme is a Sequenase. In some cases, the Sequenases comprises 1:1 ratio of Sequenase and Inorganic Pyrophosphatase. The final concentration of the polymerase is about 0.01 µM, about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or more. The final concentration of the polymerase is about 0.01 µM, about 0.1 µM, about 0.2 µM, about 0.3 µM, about 0.4 µM, about 0.5 µM, about 0.6 µM, about 0.7 µM, about 0.8 µM, about 0.9 µM, about 1.0 µM, about 1.2 µM, about 1.5 µM, about 1.8 µM, about 2.0 µM, or less. The final concentration of the polymerase is between to about 2.0 µM, between about 0.1 µM to about 1.0 µM, between about 0.5 µM to about 1.5 µM, or between about 0.8 µM to about 1.8 µM.

Typically, a volume of nuclease-free water is added to the reaction mixture to achieve a desired final volume. The final volume of the reaction mixture Y is about 10 µl, about 20 µl, about 25 µl, about 30 µl, about 40 µl, about 50 µl, or about 100 µl Depending on the final volume of reaction mixture, the amount of nuclease-free water is about 0.1 µl, about 0.5 µl, about 0.8 µl, about 1.0 µl, about 2 µl, about 5 µl, about 10 µl, about 15 µl, about 20 µl, about 25 µl, about 30 µl, about 40 µl, about 50 µl, about 80 µl, about 90 µl, about 95 µl, or more. The amount of nuclease-free water is about 0.1 µl, about 0.5 µl, about 0.8 µl, about 1.0 µl, about 2 µl, about 5 µl, about 10 µl, about 15 µl, about 20 µl, about 25 µl, about 30 µl, about 40 µl, about 50 µl, about 80 µl, about 90 µl, about 95 µl, or less. The amount of nuclease-free water is between about 0.1 µl to about 95 µl, between about 1.0 µl to about 10 µl, between about 5 µl to about 50 µl, or between about 20 µl to about 80 µl.

In some embodiments, the reaction mixture Y is incubated for about 20 minutes at 24° C. The mixture is incubated for a longer or a shorter time. For example, the reaction mixture Y is incubated for about 10 minutes, about 15 minutes, about 20 minutes, about 30 minutes, or more. The temperature is more than, less than, or about 18° C., about 20° C., about 25° C., about 28° C. preferably, the incubation is performed in a thermal cycler or heating block. The tube can then be placed on a magnetic stand for a period of time to allow the solution to clear up. The supernatant is removed and discarded. The tube is then removed from the magnetic sand and the beads are resuspended in about 200 µl of Bead Wash Buffer, before returning to the magnetic stand, left to sit until the solution clear up. The supernatant is carefully removed. The washing procedures is typically repeated for at least additional 2 times. The remaining liquid after the final wash is carefully removed.

In some embodiments, the reaction Y is added to a reaction mixture to generate reaction mixture Z. In general, the reaction Y is added to a reaction mixture Z in a PCR tube comprising a PCR Universal Primer I, a PCR Primer II with barcodes, a KAPA HiFi PCR Amplification Mix, and Nuclease-Free water.

In some cases, the final concentration of PCR Universal Primer I in the total reaction mixture Z' is about 10 µM, 20 µM, 30 µM, 40 µM, about 50 µM, about 100 µM, about 150 µM, about 200 µM, or more. The final concentration of PCR Universal Primer I in the total reaction mixture Z' is about 10 µM, 20 µM, 30 µM, 40 µM, about 50 µM, about 100 µM, about 150 µM, about 200 µM, or less. The final concentration of PCR Universal Primer I in the total reaction mixture Z' is between about 10 µM to about 200 µM, between about 30 µM to about 80 µM, between about 50 µM to about 100 µM, or between about 40 µM, or between about 40 µM, to about 150 µM.

In some cases, the final concentration of PCR Primer II in the total reaction mixture Z' is about 10 µM, 20 µM, 30 µM, 40 µM, about 50 µM, about 100 µM, about 150 µM, about 200 µM, or more. The final concentration of PCR Primer II in the total reaction mixture Z' is about 10 µM, 20 µM, 30 µM, 40 µM, about 50 µM, about 100 µM, about 150 µM, about 200 µM, or less. The final concentration of PCR Primer II in the total reaction mixture Z' is between about 10 µM to about 200 µM, between about 30 µM to about 80 µM, between about 50 µM to about 100 µM, or between about 40 µM, to about 150 µM.

In some cases, the reaction mixture comprises a KAPA HiFi PCR Amplification Mix. Typically, the final concentration of KAPA HiFi PCR Amplification Mix in the reaction mixture Z' is about 10% of the original concentration of the mix. In some cases, the final concentration of KAPA HiFi PCR Amplification Mix in the reaction mixture Z' is about 5%, about 10%, about 15%, about 20%, about 30% or less, of the original concentration of the mix. For example, depending on the final volume of the reaction mixture Z', the amount of KAPA HiFi PCR Amplification Mix to be added is less than, more than or about 1 about about 2.5 about 3 about 4 about 5 about 10 µl.

Typically, a volume of nuclease-free water is added to the reaction mixture Z' to achieve a desired final volume. The final volume of the reaction mixture Z' is about 10 µl, about 20 µl, about 25 about 30 µl, about 40 µl, about 50 µl, or about 100 µl. Depending on the final volume of reaction mixture, the amount of nuclease-free water is about 0.1 µl, about 0.5 µl, about 0.8 µl, about 1.0 about 2 µl, about 5 µl, about 10 µl, about 15 µl, about about 25 µl, about 30 about 40 µl, about 50 µl, about 80 µl, about 90 µl, about 95 µl, or more. The amount of nuclease-free water is about 0.1 µl, about 0.5 about 0.8 µl, about 1.0 µl, about 2 µl, about 5 µl, about 10 µl, about 15 µl, about 20 about 25 µl, about about 40 µl, about 50 about 80 µl, about 90 µl, about 95 µl, or less. The amount of nuclease-free water is between about 0.1 µl to about 95 µl, between about 1.0 µl to about 10 µl, between about 5 µl to about 50 µl, or between about 20 µl to about 80 µl.

The reaction mixture Z is placed in a thermal cycler to perform a polymerase chain reaction (PCR) and generate a product of XX. The PCR program comprises at least 1 cycle at about 98° C. for 2 minutes for denaturing the DNA, at least 15 cycles at about 98° C. for 20 seconds for denaturing, lower the temperature to about 60° C. for 30 seconds for annealing the primers, increase the temperature to about 72° C. for 30 seconds for extension, at least 1 cycle at about 72° C. for 5 minutes for final extension, and kept at 4° C. In some cases, the DNA denature temperature is about 92° C., about 95° C., about 97° C., or about 99° C. In some cases, the primer annealing temperature is about 45° C., about 50° C., about 55° C., about 60° C., about 65° C., or about 70° C. In some cases, the extension temperature is about 65° C., about 70° C., about 72° C., or about 75° C.

The product XX is cleaned with AmpureXP Beads. In general, the PCR tube comprising product XX is placed on a magnetic stand, and kept still for the solution to clear up until the supernatant is removed by pipetting. The supernatant is transferred to a new 0.5 mL Eppendorf DNA LoBind tube. The PCR tube containing the Capture Beads is discarded. Typically, about 100 µl of AmpureXP Beads are added to the supernatant, and the mixture is mixed by pipetting up and down, before incubating at room temperature for about 10 minutes. In some cases, the incubation time is longer or shorter than 10 minutes, such as about 5 minutes, about 15 minutes, about 20 minutes, about 30 minutes, or more. The tube is placed on the magnetic stand to allow the solution to clear up. The supernatant is discarded. About 200 µl of 80% ethanol is added to the tube, and let sit for about 30 seconds, before removing and discarding the ethanol. It may not be necessary to remove the tube from the magnetic stand during this procedure. The tube is washed with 200 µl of 80% ethanol for at least additional 1 time. The cap of the tube is opened and allow the beads to air dry for about 10-15 minutes. About 20 µl to about 30 µl of 10 mM Tric-HCl (pH7.8) is added to the beads. The resulting mixture is mixed by pipetting up and down, before allowing to sit at room temperature for about 2 minutes. The tube is placed on the magnetic stand to allow the solution to clear. The supernatant containing the eluted DNA is transferred to a new Eppendorf DNA LoBind tube. The product can then be used to generate a library, and is quantitated on an Agilent Bioanalyzer using a high sensitivity DNA chip prior to sequencing.

It is observed that in some embodiments, all steps of library preparation up to this point are performed in a single volume. In some cases the single volume is a single tube. In some cases the single volume is a single well in a plate. Optionally, after library generation, the DNA is size selected using either bead-based or agarose gel-based methods and that the library is quantitated on an Agilent Bioanalyzer using a high sensitivity DNA chip prior to sequencing.

Throughout the specification herein, the disclosure is sorted into sections for ease of understanding. These divisions are understood to be for ease of understanding and not necessarily to limit the applicability of some sections of the specification with respect to one another. Accordingly, disclosure in any one section of the specification is relevant in some cases not only to that section but to other sections and in some cases to the disclosure as a whole.

EXAMPLES

In order that the methods and compositions described herein may be more fully understood, the following examples are set forth. It should be understood that these examples are for illustrative purposes only and are not to be construed as limiting in any manner.

Example 1: Rapid DNA Library Prep

Obtain the target nucleic acid sequence. This is 50 ng of genomic deoxyribonucleic acid (gDNA) or 1 ng-10 ng of gDNA in various cases. Mix the gDNA with random oligonucleotide primers containing 5' sequencing adapter tails. Then add a pool of deoxynucleotide triphosphates (dNTPs) containing a fixed ratio of each of the four dNTPs to a fixed ratio of biotinylated dideoxynucleotide triphosphates (ddNTPs), reaction buffer, and nuclease-free water. Incubate this mixture at 98 C for 3 minutes to denature the DNA. Place the tube on ice for at least 2 minutes immediately afterwards. Add to this mixture a DNA polymerase having strand displacement activity and ddNTP/biotin incorporation ability. Incubate this reaction at room temperature (approximately 22 C) for 30 minutes.

During this time, prepare the streptavidin-coated magnetic beads by shaking the tube containing the beads thoroughly to resuspend the beads. Transfer the beads to a new tube and place the tube onto a magnetic separation stand. Allow the solution to clear (approximately 0.5-1 minute) and then carefully remove and discard the supernatant with a pipette. Remove the tube from the magnetic separation stand and add HS Buffer, or another suitable buffer, to the beads. Pipette the sample up and down to mix the components and then return the tube to the magnetic stand. Wait for the solution to clear. Carefully remove and discard the supernatant. Remove the tube from the magnetic stand and resuspend the beads in HS Buffer.

Add the DNA mixture to the magnetic beads and incubate the sample at room temperature for 30 minutes. Mix the sample by pipetting up and down at 10 minute intervals. Place the tube on the magnetic stand and wait for the solution to clear. Carefully remove the supernatant with a pipette and discard it. Remove the tube from the magnetic stand and resuspend the beads in Bead Wash Buffer (1X Tris-EDTA buffer). Return the tube to the magnetic stand, allow the solution to clear and discard the supernatant. Perform this step two additional times. Carefully remove any remaining liquid after the final wash.

Mix the magnetic beads with a second set of random oligonucleotide primers containing 5' sequencing adapter tails and a pool of dNTPs. Add to this mixture a DNA polymerase having strand displacement activity and incubate the reaction for 20 minutes at room temperature (approximately 22° C.). Then place the tube on the magnetic stand. Allow the solution to clear and remove the supernatant. Remove the tube from the magnetic stand and resuspend the beads in Bead Wash Buffer (1X Tris-EDTA). Return the tube to the magnetic stand, allow the solution to clear and discard the supernatant. Perform this step two additional times. Carefully remove any remaining liquid after the final wash.

Resuspend the beads in nuclease-free water. Transfer the beads to a PCR tube and add primers complementary to the adapters and PCR master mix (containing Taq DNA polymerase, dNTPs, $MgCl_2$, and reaction buffers). Input the following parameters into a thermal cycler and perform PCR: 1 cycle (98° C., 2 minutes); 6 cycles (98° C., 20 seconds; 60° C., 30 seconds; 72° C., 30 seconds); 1 cycle (72° C., 5 minutes; 4° C.—hold). Run the second step for 15 cycles instead of 6 if using 1 ng-10 ng gDNA input.

Place the PCR tube on a magnetic stand, wait for the solution to clear, and transfer the supernatant to a new tube. Discard the PCR tube containing the magnetic beads. Add magnetic PCR purification beads (e.g., AMPure XP beads, Beckman Coulter, Brea, Calif.) to the supernatant, pipette to mix and incubate the tube at room temperature for 10 minutes. Place the tube in the magnetic stand, allow the solution to clear, and discard the supernatant. Add 80% ethanol to the tube. Wait 30 seconds, then remove and discard the ethanol. It is unnecessary to remove the tube from the magnetic stand during this step. Repeat the wash step with additional 80% ethanol. Open the cap on the tube and allow the beads to air dry for 10-15 minutes on the laboratory bench. Add 10 mM Tris-HCl (pH 8.0) to the beads. Mix by pipetting up and down. Allow the tube to sit at room temperature for 1-2 minutes. Then place the tube on the magnetic stand, allow the solution to clear and transfer the supernatant containing the eluted DNA to a new tube. The DNA can then be size selected using either bead-based or agarose gel-based methods and then quantitated on a bioanalyzer (e.g., Agilent 2100 Bioanalyzer, Agilent Technologies, Santa Clara, Calif.) using a high sensitivity DNA chip prior to sequencing.

Example 2: RNA Rapid Library Prep

Complementary deoxyribonucleic acid (cDNA) is used as the target nucleic acid sequence in place of the gDNA described in Example 1. An additional step of creating cDNA from ribonucleic acid (RNA) is performed prior to the steps detailed in Example 1. Oligo dT primers is used to synthesize the cDNA and restrict the cDNA library to messenger RNA with poly(A) tails or random primers is used to synthesize cDNA from full length transcripts of all RNA species.

Alternatively, RNA may be used as the target nucleic acid sequence. When using RNA, a reverse transcriptase (e.g., HIV reverse transcriptase) with the capability of incorporating ddNTP/biotin is used in place of the DNA polymerase.

Example 3: Long Read Rapid Library Prep

Long reads may be obtained with minor modification to the protocol described in Example 1. Fragment the target nucleic acid sequence into DNA fragments 10 kilobases or longer. Fragmenting may be done by physical, chemical, or enzymatic means. An example is the G-TUBE (Covaris Inc., Woburn, Mass.). Next, dilute the fragments into reaction vesicles (e.g., microplates or oil-in-water emulsions) and add the mix of DNA polymerase, dNTPs, biotin-ddNTPs, and reaction buffer as described in Example 1. A primer library consisting of 1544 sequencing adapter+error-correcting label+random primer is formed as a water-in-oil emulsion. Water-in-oil emulsion droplets containing the diluted long fragment DNA are generated in the system and merged with the primer library droplets in a 1:1 ratio. The primers bind randomly to the fragments, extend, and terminate with a biotin-ddNTP. The emulsion is broken, run across a column to remove oil and surfactant, and the product is captured with streptavidin-coated magnetic beads. The remainder of the protocol is as described in Example 1.

Example 4: Targeted Rapid Library Prep

Targeted sequencing may be performed with slight variation to the protocol described in Example 1. gDNA is random primed, extended, terminated with biotin-ddNTP, and captured in the same manner as in Example 1. Locus-specific primers containing 5' sequencing adapter tails are used in place of the second set of random oligonucleotide primers containing 5' sequencing adapter tails. The locus specific sequences bind to their targets and are extended by a thermostable DNA polymerase with strand displacing activity. The beads are washed to remove excess dNTP, enzyme, and primer. The resulting product is released from the bead and sequenced or amplified through the use of the adapter sequences and PCR.

Example 5: Rapid Library Prep Examples and Comparisons

A sequencing library was obtained for a sample with the Rapid Library Prep protocol and compared to a sequencing library obtained with NEXTERA (Illumina, San Diego, Calif.), a commercially available sequencing library kit. The specificity is defined as the percentage of reads covering the genome/target regions versus unwanted sequence/wasted capacity. The sensitivity is defined as the percentage of the genome/target regions giving high quality sequence (greater than 20× at a Phred quality score of 30) with duplicates removed. Performance specifications are presented in Table 2.

TABLE 2

Performance specifications for a Rapid Library Prep example.

| Feature | Specification |
| --- | --- |
| DNA input | 1 ng |
| % mapped reads | >99% |
| % > 20x | >99% (100x avg) |

The sequencing library obtained using the Rapid Library Prep protocol was compared to a sequencing library obtained with a NEXTERA kit (Illumina, San Diego, Calif.). The sample was 4,641,652 bases from *Escherichia coli* and the number of cycles for NEXTERA (NXT) was 12 and for the Rapid Library Prep (IGX) was 15. The comparison is shown in Table 3. A comparison of the uniformity and guanine-cytosine (GC) bias for the NEXTERA library (left side) and the Rapid Library Prep right side) is shown in FIG. 5A-5B.

TABLE 3

Comparison of sequencing libraries obtained with NEXTERA and Rapid Library Prep.

| Sample | Input | # reads | % mapped | Avg depth | % > 1x | % > 5x | % > 10X | % > 20x | % > 100x | % GC |
| --- | --- | --- | --- | --- | --- | --- | --- | --- | --- | --- |
| IGX1A | 1 ng | 3660404 | 98.15 | 210 | 99.99 | 99.96 | 99.88 | 99.62 | 87.54 | 50.79 |
| IGX1B | 1 ng | 3096283 | 97.83 | 178 | 99.99 | 99.93 | 99.75 | 99.29 | 77.07 | 50.79 |
| IGX2A | 10 ng | 4280731 | 98.93 | 240 | 100 | 100 | 100 | 100 | 98.64 | 50.79 |
| IGX2B | 10 ng | 3151972 | 98.25 | 176 | 99.96 | 99.84 | 99.64 | 99.13 | 81.95 | 50.79 |
| NXT1A | 1 ng | 2292221 | 99.83 | 131 | 99.99 | 99.84 | 99.55 | 98.78 | 85.55 | 50.79 |
| NXT1B | 1 ng | 1688853 | 99.89 | 94 | 100 | 99.95 | 99.76 | 99.10 | 39.71 | 50.79 |

A comparison of the sequence quality for the NEXTERA library (left side) and the Rapid Library Prep library (right side) is shown in FIG. 6A-6B, and a comparison of the guanine-cytosine (GC) content for the same two libraries is shown in FIG. 7A-7B. A comparison of the nucleotide contribution for the same two libraries is shown in FIG. 8A-8B. In FIG. 6A-6B, FIG. 7A-7B, and FIG. 8A-8B, the input was 1 ng of DNA with 12 cycles of PCR for NEXTERA and 15 cycles for the Rapid Library Prep.

The effect of cycle number using 50 ng of human gDNA is shown in FIG. 9A-9E. A Rapid Library Prep using 250 cells of a human cell line was performed and the base distribution (left panel), quality by cycle (center) and GC bias (right panel) is shown in FIG. 10A-10C. When the input was 100 ng, the % map was >99%; the % dup was 0.937; and the mean was 0.18×. When the input was 2 ng, the % map was >95%; the % dup was 9.8; and the mean was 0.66×. The SEQUENASE concentration (at 24° C.) at 0 minutes was 6.48; at 20 minutes was 8.39; at 2 hours was 11.4; and at 4 hours was 13.6.

Counts of reads matching a given label for 250 cells and 20 kb molecules are presented in FIG. 14A-14B. The summary statistics of read label assignments for zero mismatch tolerance is presented in Table 4. The summary statistics of read label assignments for one mismatch tolerance is presented in Table 5. Counts of reads matching a given label with 1545 labels and 400 µg of input are presented in FIG. 15A-15C.

TABLE 4

Summary statistics of read label assignments for zero mismatch tolerance.

| Run Name | Reads with Labels | Total Reads | % of Reads with Labels |
|---|---|---|---|
| RD-RLP-20-1-S2-L001-R1-001 | 2903598 | 3233925 | 89.78% |
| RD-RLP-10-1-S1-L001-R1-001 | 2973833 | 3313075 | 89.76% |
| RD-RLP-D4-S6-L001-R1-001 | 4954467 | 5505772 | 89.98% |
| RD-RLP-B4-S5-L001-R1-001 | 3859551 | 4299992 | 89.75% |

TABLE 5

Summary statistics of read label assignments for one mismatch tolerance.

| Run Name | Reads with Labels | Total Reads | % of Reads with Labels |
|---|---|---|---|
| RD-RLP-20-1-S2-L001-R1-001 | 3072036 | 3233925 | 94.99% |
| RD-RLP-10-1-S1-L001-R1-001 | 3148171 | 3313075 | 95.02% |
| RD-RLP-D4-S6-L001-R1-001 | 5236583 | 5565772 | 95.11% |
| RD-RLP-B4-S5-L001-R1-001 | 4085919 | 4299992 | 95.02% |

A summary of low coverage Rapid Library Prep human data is provided in Table 6.

Example 6—Random Oligo Sequence Selection Bias

The human genome is biased towards AT rather than GC base pairs. As seen in FIG. 10C (right panel), the human genome, when calculated in 100 bp windows, demonstrates a peak number of windows at about 40% GC, rather than 50% as would be predicted for an equal GC/AT base pair distribution.

To generate a Random Library, a population of first round synthesis oligos is synthesized. The first strand oligonucleotides each comprise a sequence adapter positioned 5' of a random 8 mer followed by a 3' OH from which template directed extension occurs. The population is synthesized such that all random 8 mers are represented in the first strand oligonucleotide population. However, to increase the efficiency of annealing and, subsequently, first strand synthesis, the population is synthesized so as to include a bias for random 8 mers having a GC percentage of about 40%, such that the overall distribution of 8 mer sequence in the first strand synthesis library reflects that of the human genome as a whole.

Example 7—Random Library First Strand Synthesis

A 50 ng human genomic DNA sample is obtained. The sample is contacted with a population of first strand synthesis oligonucleotides synthesized as in Example 6. The first strand oligonucleotides each comprise a sequence adapter 5' of a random 8'mer followed by a 3' OH from which template directed extension occurs.

TABLE 6

Low coverage Rapid Library Prep human data.

| sample | input | PCR cycles | ddNTP % | # of reads | % in pairs | % dup | unique library size | GC windows with 0 coverage (#) range | mean insert sire | mean coverage |
|---|---|---|---|---|---|---|---|---|---|---|
| m039.RD-RLP800-15c.S1.L001 | 800 pg | 15 | 0.80% | 9,968,536.00 | 0.988126 | 0.559547 | 4,109,242.00 | (9)84-93 | 409.693767 | 0.088391 |
| m039.RD-RLP800-18c.S2.L001 | 800 pg | 18 | 0.80% | 9,949,106.00 | 0.988351 | 0.477504 | 4,739,323.00 | (8)85-93 | 375.287359 | 0.080893 |
| m039.RD-RLP400-18c.54.L001 | 400 pg | 18 | 0.80% | 16,266,008.00 | 0.98816 | 0.595415 | 3,629,979.00 | (6)87-93 | 274.694601 | 0.052058 |
| m039.RD-RLP400-15c.S3.L001 | 400 pg | 15 | 0.80% | 8,427,814.00 | 0.989546 | 0.755995 | 1,549,378.00 | (9)84-93 | 421.863197 | 0.040791 |
| Hs01-BC5-S1-L002 | 2 ng | 15 | 0.40% | 27,899,210.00 | 0.991011 | 0.180572 | 52,354,361.00 | (1)100 | 324.944281 | 0.671878 |
| Hs005-BC6-S2-L001 | 2 ng | 15 | 0.20% | 24,454,180.00 | 0.991487 | 0.299273 | 24,088,032.00 | (1)100 | 320.531634 | 0.504618 |
| Hs005-BC6-S2-L002 | 2 ng | 15 | 0.20% | 25,535,376.00 | 0.991425 | 0.307106 | 24,260,182.00 | (1)100 | 322.994129 | 0.519949 |
| HS0025-BC7-S3-L001 | 2 ng | 15 | 0.10% | 30,536,626.00 | 0.993254 | 0.609468 | 9,063,258.00 | (1)100 | 326.756584 | 0.346054 |
| HS0025-BC7-S3-L002 | 2 ng | 15 | 0.10% | 31,871,174.00 | 0.993139 | 0.618582 | 9,114,873.00 | (1)100 | 328.802436 | 0.351881 |
| HS0025-BC7-S4-L001 | 2 ng | 15 | 0.10% | 27,327,370.00 | 0.988436 | 0.665876 | 6,464,561.00 | (1)100 | 320.705219 | 0.257921 |
| HS00125-BC8-S4-L001 | 2 ng | 15 | 0.05% | 27,327,370.00 | 0.988436 | 0.665876 | 6,464,561.00 | (1)100 | 320.705219 | 0.257921 |
| HS00125-BC8-S4-L002 | 2 ng | 15 | 0.05% | 28,468,382.00 | 0.988123 | 0.673864 | 6,510,699.00 | (1)100 | 322.280338 | 0.26124 |

As discussed in Example 6, the random 8 mer population of the first round synthesis oligos represents all possible 8 mers, but the relative abundance of each 8 mer is biased to match the relative abundance of GC vs AT base pairs in the human genome. 4 uL of the population is added to the sample.

Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a relative ratio of 99% deoxy NTP to 1% di-deoxy NTP. 8 uL of the buffer/NTP composition is added to the sample.

The mixture is diluted to 19 uL total volume. The mixture is heated to 98° C. for 3 minutes, during which time the genomic DNA is caused to 'melt' into single-strands unbound by hydrogen boding between complementary bases.

The mixture is then cooled on ice for 2 minutes to allow for reverse-complementary base-pairing between the first strand synthesis oligonucleotides and the genomic sample. It is observed that some oligonucleotides demonstrate complete reverse-complementarity between their random 8 mer and the genomic sequence to which each binds. It is also observed that some oligonucleotides bind to genomic regions that are incompletely reverse-complementary to the oligo's random 8 mer. The failure to base pair with complete reverse complementarity is not detrimental to subsequent steps in the random library prep process.

Sequenase DNA polymerase (1 uL) having strand displacement activity and able to incorporate biotin-ddNTP is added to the composition. The composition is heated to room temperature and allowed to continue for 30 minutes.

Extension from the 3' OH of the first strand synthesis oligonucleotides is observed, resulting in sequence reverse complementary to the template at the annealing site of each annealed oligo being incorporated at the 3' end of each annealed oligo. Extension continues until a biotin-labeled ddNTP molecule is incorporated, at which point extension terminates. It is further observed that, in light of the 99%/1% ratio of dNTP to biotin-ddNTP complexes, 50% of the first strand oligos on which extension occurs demonstrate an extension of over 50 bases prior to the incorporation of an biotin-ddNTP molecule.

The composition is then heated to 98° C. for 5 minutes, during which extension stops.

Example 8—Tagged First Strand Isolation

Magnetic Streptavidin capture beads are provided in binding buffer, mixed, and allowed to settle on a magnetic stand. The binding buffer is replaced to a 200 uL volume and the process repeated. The supernatant is drawn off and the beads are resuspended in 40 uL of binding buffer.

The denatured sample/first strand synthesis mixture is added to the resuspended beads. The bead/sample mixture is incubated at 22 C and agitated at 10 minute intervals for 30 minutes. The mixture is then put on a magnetic stand and, upon settling of the beads, the supernatant is removed. The tube is agitated and allowed to settle on a magnetic stand.

Beads are washed three times with 200 uL of TE buffer.

Example 9—Second Strand Synthesis

First strand library templates are eluted from the streptavidin tags and resuspended in nucleic acid synthesis buffer including dNTP. A second probe library is added, comprising a population of second strand primers. Each second strand primer comprises a B-adapter sequence 5' to a random 8 mer sequence terminating in a 3' OH from which nucleic acid synthesis can occur.

The mixture is heated to 98° C. for 3 minutes. The mixture is cooled on ice for 2 minutes to allow for reverse-complementary base-pairing between the second strand synthesis oligonucleotides and the first strand library. It is observed that some oligonucleotides demonstrate complete reverse-complementarity between their random 8 mer and the first strand sequence to which each binds. It is also observed that some oligonucleotides bind to genomic regions that are incompletely reverse-complementary to the oligo's random 8 mer. The failure to base pair with complete reverse complementarity is not detrimental to subsequent steps in the random library prep process.

The composition is heated to room temperature and allowed to continue for 30 minutes.

Extension from the 3' OH of the first strand synthesis oligonucleotides is observed, resulting in sequence reverse complementary to the template at the annealing site of each annealed oligo being incorporated at the 3' end of each annealed oligo. Extension continues until the 5' end of the first strand template is reached. It is observed that second-strand oligos annealing away from the 3' end of the first strand template undergo extension from their 3' ends, but are displaced from the first strand by extension reactions primed by oligos annealing further toward the 3' end of the first strand template.

Accordingly, double-stranded library molecules are synthesized, comprising two distinct strands: 1) a first strand having, from the 5' end, an A adapter, a random 8 mer sequence and target sequence on the order of 1-100 nucleotides, terminating in a biotin-tagged ddNTP; and 2) a second strand having, from the 5' end a B adapter, a second random 8 mer sequence, a target sequence derived from the sample, a first random 8 mer sequence reverse complementary to the random 8 mer of the first strand, and sequence reverse complementary to the first A adapter.

Example 10—Tagged Second Strand Isolation

Magnetic Streptavidin capture beads are provided in binding buffer, mixed, and allowed to settle on a magnetic stand. The binding buffer is replaced to a 200 uL volume and the process repeated. The supernatant is drawn off and the beads are resuspended in 40 uL of binding buffer.

The second strand synthesis mixture is added to the resuspended beads. The bead/sample mixture is incubated at 22° C. and agitated at 10 minute intervals for 30 minutes. The mixture is then put on a magnetic stand and, upon settling of the beads, the supernatant is removed. The tube is agitated and allowed to settle on a magnetic stand.

Supernatant is drawn off and beads are washed three times with 200 uL of TE buffer. The result of this process is a population of streptavidin purified, double-stranded library molecules, comprising two distinct strands: 1) a first strand having, from the 5' end, an A adapter, a random 8 mer sequence and target sequence on the order of 1-100 nucleotides, terminating in a biotin-tagged ddNTP; and 2) a second strand having, from the 5' end a B adapter, a second random 8 mer sequence, a target sequence derived from the sample, a first random 8 mer sequence reverse complementary to the random 8 mer of the first strand, and sequence reverse complementary to the first A adapter.

Example 11—Sequencing Library Generation

Beads are resuspended in 42 uL of nuclease free water, to which is added 4 uL of Adapter A primer, 4 uL of Adapter B primer, and 50 uL of 2×PCR master mix.

The Adapter A primer comprises sequence identical to the first adapter of the double-stranded template at the primer's 3' end, and further comprises sequence necessary for sequencing by synthesis reactions as described herein.

The Adapter B primer comprises sequence identical to the second adapter of the second strand of the double-stranded template at the primer's 3' end, and further comprises sequence necessary for sequencing by synthesis reactions as described herein.

The mixture is subjected to thermocycling as follows: 98° C. for 2 minutes; followed by 6 cycles of 98° C., 20 second, 60° C., 30 seconds, and 72° C., 30 seconds; following said six cycles the reaction is held at 72° C. for 5 minutes and then is stored at 4° C.°

Example 12—Sequence Library

The sequencing library generated thereby is observed to have the following characteristics. Each double-stranded molecule comprises, in order, an adapter A sequence sufficient for sequencing by synthesis, a first random 8 mer, a target region of unknown length but likely within 1-100 bases, a second random 8 mer, and a B adapter sequence sufficient for sequencing by synthesis as disclosed herein.

It is observed that library constituents possess the following characteristics. Each molecule comprises a first 8 mer molecular tag that is independent of the first 8 mer of other molecules in the library. Each molecule comprises a target sequence, corresponding to sequence of the original sample. The starting point of the target sequence, the length of the target sequence, and the endpoint of the target sequence of each given molecule is independent of the starting point, length and end point of each other molecule in the library. Each molecule comprises a second 8 mer molecular tag that is independent of the second 8 mer of other molecules in the library.

It is observed that the library, in aggregate, possesses the following characteristics. Substantially all of the sample sequence is represented in the library by multiple overlapping molecules. Substantially all of the library molecules (barring rare events), prior to the final addition of A and B adapters through thermocycling, are unique, varying from one another as to their first 8-mer sequence, target sequence starting point, target sequence, target sequence length, target sequence end point, and second 8 mer sequence.

Example 13—Sequence Data Assessment: Heterozygosity

A sequence library as generated herein is subjected to sequence by synthesis compatible with its A adapter and B adapter, and the sequence results are assessed. Independently, a second aliquot of the original sample is prepared for sequencing using standard PCR-based library tagging involving substantial PCR-based amplification of untagged template. The libraries are sequenced and the results compared.

The sample from which the libraries are generated is heterozygous at a first position in the genome, comprising a single base variant. During the library generation, both for the traditional method and using the methods and compositions disclosed herein, point mutations occur at some small frequency.

Sequence from a conventional library generation method is generated and assembled. Sequence reads are observed that differ by a single base at a single homologous position. Multiple reads each representing each allele at the position are obtained. It is inferred that the single base difference represents a base at which the original sample is heterozygous.

Sequence from a library generated as disclosed herein is generated and analyzed. Sequence reads are observed that differ by a single base at a single homologous position. Forty reads represent the variant base. It is observed that all reads representing the variant base at the position share a common first 8-mer sequence, a target sequence starting point, a target sequence length, a target sequence end point, and a second 8 mer sequence—that is, all reads indicating the variant base map to a single unique synthesized library molecule. 40 other reads are observed spanning the base position, none of which indicate the presence of the variant base. It is observed that the 40 reads that do not represent the variant base at the homologous position map to 10 distinct synthesized library molecules, as indicated by assessing first 8-mer sequence, a target sequence starting point, a target sequence length, a target sequence end point, and a second 8 mer sequence. It is concluded that the reads representing the variant base result from an error in incorporation followed by differential amplification of the erroneous synthesis event. The sequence information is excluded from the sequence assembly.

Sequence from a library generated as disclosed herein is generated and analyzed with regard to a second putatively heterozygous position. Sequence reads are observed that differ by a single base at a single homologous position. Forty reads represent the variant base. It is observed that 50 reads representing the variant base at the position map to 10 distinct synthesized library molecules, as indicated by assessing first 8-mer sequence, a target sequence starting point, a target sequence length, a target sequence end point, and a second 8 mer sequence. 40 other reads are observed spanning the base position, none of which indicate the presence of the variant base. It is observed that the 40 reads that do not represent the variant base at the homologous position map to 12 distinct synthesized library molecules, as indicated by assessing first 8-mer sequence, a target sequence starting point, a target sequence length, a target sequence end point, and a second 8 mer sequence. It is concluded that the reads representing the variant base result from an accurate representation of the sample sequence, as indicated by the variant appearing in multiple independently generated molecules in the library.

Example 14—Sequence Data Assessment: Repetitive Sequence Quantification

A sequence library as generated herein is subjected to sequence by synthesis compatible with its A adapter and B adapter, and the sequence results are assessed. Independently, a second aliquot of the original sample is prepared for sequencing using standard PCR-based library tagging involving substantial PCR-based amplification of untagged template. The libraries are sequenced and the results compared.

It is observed that a sequence corresponding to a transposon is identified in the traditional sequence library sequencing results. The transposon monomer unit is observed to be found adjacent to multiple non-transposon border sequences, suggesting that it is present in multiple copies in the sample. Transposon reads correspond to 5% of the total sequence generated. It is concluded that transposons represent 5% of the nucleic acid sample.

Sequence from a library generated as disclosed herein is generated and analyzed. Sequence reads corresponding to a transposon are identified. Transposon reads correspond to 5% of the total sequence generated. It is observed that sequence reads mapping to transposon sequence map to a plurality of unique synthesized library molecules, as indicated by assessing first 8-mer sequence, a target sequence starting point, a target sequence length, a target sequence end point, and a second 8 mer sequence. It is observed that each unique synthesized library molecule representing transposon sequence is represented by no more than 2-3 sequence reads. By comparison, the average unique read is represented by 10-20 sequence reads in this particular data set. This plurality of transposon-mapping reads, in total, represents 30% of the total number of unique reads in the sequence dataset.

It is concluded from the sequence data set generated from the sequencing library generated as disclosed herein that transposon sequence represents about 30% of the sequence of the sample provided, rather than 5% as suggested by analysis of the sequence reads form the library produced through previous methods, and it is further concluded that the particular transposon sequence is poorly amplified with respect to other sequence in the dataset.

Example 15—Sequence Data Assessment: Complex Rearrangement Detection

A sequence library as generated herein is subjected to sequence by synthesis compatible with its A adapter and B adapter, and the sequence results are assessed. Independently, a second aliquot of the original sample is prepared for sequencing using standard PCR-based library tagging involving substantial PCR-based amplification of untagged template. The libraries are sequenced and the results compared.

It is observed that a sequence read from the standard PCR-based library tagging comprises sequence that maps to two distinct contigs not believed to be adjacent in the reference human genome. A separate sample is generated and PCR using newly synthesized primers that flank the identified junction sequence is used to confirm that the sequences are in fact adjacent.

Sequence from a library generated as disclosed herein is generated and analyzed. It is observed that sequence reads spanning the two nonadjacent contig sequences map to a plurality of unique synthesized library molecules, as indicated by assessing first 8-mer sequence, a target sequence starting point, a target sequence length, a target sequence end point, and a second 8 mer sequence. It is concluded that the sequence reads spanning the two nonadjacent contig sequences are in fact adjacent in the source of the sample.

Example 16—cDNA Sequencing Library Generation

A total RNA sample is obtained from a population of 50 cells. The sample is contacted with a population of first strand synthesis oligonucleotides. The first strand oligonucleotides each comprise a sequence adapter 5' of a random 8'mer followed by a 3' OH from which template directed extension occurs.

The random 8 mer population of the first round synthesis oligos represents all possible 8 mers, but the relative abundance of each 8 mer is biased to match the relative abundance of GC vs AT base pairs in the human transcriptome. 4 uL of the population is added to the sample.

Also added to the composition is an HIV reverse transcriptase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a relative ratio of 99% deoxy NTP to 1% di-deoxy NTP. 8 uL of the buffer/NTP composition is added to the sample.

The mixture is diluted to 19 uL total volume. The mixture is heated to 98° C. for 3 minutes, during which time the RNA is caused to 'melt' into single-strands.

The mixture is then cooled one ice for 2 minutes allow for reverse-complementary base-pairing between the first strand synthesis oligonucleotides and the RNA sample. It is observed that some oligonucleotides demonstrate complete reverse-complementarity between their random 8 mer and the RNA sequence to which each binds. It is also observed that some oligonucleotides bind to RNA regions that are incompletely reverse-complementary to the oligo's random 8 mer. The failure to base pair with complete reverse complementarity is not detrimental to subsequent steps in the random library prep process.

HIV reverse transcriptase (1 uL) having strand displacement activity and able to incorporate biotin-ddNTP is added to the composition. The composition is heated to room temperature and allowed to continue for 30 minutes.

Extension from the 3' OH of the first strand synthesis oligonucleotides is observed, resulting in sequence reverse complementary to the template at the annealing site of each annealed oligo being incorporated at the 3' end of each annealed oligo. Extension continues until a biotin-labeled ddNTP molecule is incorporated, at which point extension terminates. It is further observed that, in light of the 99%/1% ratio of dNTP to biotin-ddNTP complexes, 50% of the first strand oligos on which extension occurs demonstrate an extension of over 50 bases prior to the incorporation of an biotin-ddNTP molecule.

The composition is then heated to 98° C. for 5 minutes, during which extension stops.

The sample is subjected to purification, second strand synthesis and library tag addition as indicated in examples 8-11, above.

Example 17—Sequence Data Assessment: Transcript Copy Number

Traditional Q-PCR is performed on an aliquot of a total RNA sample obtained from a population of 50 cells. The sample is reverse-transcribed using random primers, and PCR is performed in the presence of SYBR-Green to quantify amplicon synthesis over time, as a measure of underlying template copy number.

It is observed that a first transcript and a second transcript of similar length lead to SYBR florescence of their respective amplicons at a similar cycle in the amplification process. It is concluded that the first and the second transcript accumulate at about the same level in the population of 50 cells from which the RNA template is derived.

The cDNA sequence library of Example 15 is sequenced and the results are analyzed. It is observed that the first transcript is represented in 100 sequence reads, mapping to 1 unique template as indicated by assessing first 8-mer sequence, a target sequence starting point, a target sequence length, a target sequence end point, and a second 8 mer sequence. The second transcript is represented in 100 reads, mapping to 50 unique templates as indicated by assessing first 8-mer sequence, a target sequence starting point, a target sequence length, a target sequence end point, and a second 8 mer sequence, and that each represented by 1-3 reads.

It is concluded that the second transcript is present at a level that is 50-fold greater than that of the first template. It is also concluded that the single template generated form the first transcript is differentially amplified relative to the templates of the second strand.

Example 18—Long Template Library Generation

A genomic DNA sample is obtained and fragmented. Fragments are size selected to have a minimum size of 10 kb. Size-selected fragments are diluted to not more than 100 fragments per aliquot and distributed into separate reaction tubes.

Each aliquoted sample is contacted with a population of first strand synthesis oligonucleotides. The first strand oligonucleotides each comprise a unique reaction tube label 5' to a sequence adapter 5' of a random 8'mer followed by a 3' OH from which template directed extension occurs. The reaction tube label sequence is common to all first strand synthesis oligos added to a given tube, but varies among tubes. The random 8 mer is unique to a single oligo, although a small degree of redundancy is easily tolerated by the methods disclosed herein, and even a large degree of redundancy is accommodated.

As discussed in Example 6, the random 8 mer population of the first round synthesis oligos represents all possible 8 mers, but the relative abundance of each 8 mer is biased to match the relative abundance of GC vs AT base pairs in the human genome. 4 uL of the population is added to the sample.

Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a relative ratio of 99% deoxy NTP to 1% di-deoxy NTP. 8 uL of the buffer/NTP composition is added to the sample.

The mixture is diluted to 19 uL total volume. The mixture is heated to 98° C. for 3 minutes, during which time the genomic DNA is caused to 'melt' into single-strands unbound by hydrogen boding between complementary bases.

The mixture is then cooled one ice for 2 minutes allow for reverse-complementary base-pairing between the first strand synthesis oligonucleotides and the genomic sample. It is observed that some oligonucleotides demonstrate complete reverse-complementarity between their random 8 mer and the genomic sequence to which each binds. It is also observed that some oligonucleotides bind to genomic regions that are incompletely reverse-complementary to the oligo's random 8 mer. The failure to base pair with complete reverse complementarity is not detrimental to subsequent steps in the random library prep process.

Sequenase DNA polymerase (1 uL) having strand displacement activity and able to incorporate biotin-ddNTP is added to the composition. The composition is heated to room temperature and allowed to continue for 30 minutes.

Extension from the 3' OH of the first strand synthesis oligonucleotides is observed, resulting in sequence reverse complementary to the template at the annealing site of each annealed oligo being incorporated at the 3' end of each annealed oligo. Extension continues until a biotin-labeled ddNTP molecule is incorporated, at which point extension terminates. It is further observed that, in light of the 99%/1% ratio of dNTP to biotin-ddNTP complexes, 50% of the first strand oligos on which extension occurs demonstrate an extension of over 50 bases prior to the incorporation of an biotin-ddNTP molecule.

The composition is then heated to 98° C. for 5 minutes, during which extension stops.

The sample is subjected to purification and second strand synthesis as indicated in examples 8-11, above. Additional cycles are added to the library tag addition thermocycling steps to account for the low amount of starting sample material.

Example 19—Sequence Data Assessment: Single Molecule Phase Mapping

Traditional sequencing is performed on a genomic sample aliquoted from the sample in Example 18 prior to the dilution step. A sequencing library is generated and sequence information is generated. Sequence data is assembled against a human genome contig scaffold. A first and a second single nucleotide polymorphism within the sequence data are identified, and the sample is scored as being heterozygous at these sites. The heterozygous sites map to a single contig. It is not clear from the sequence information what the physical linkage status is among the polymorphisms—that is, it is not clear which polymorphisms are paired with one another, or in phase with one another, on the same actual nucleic acid molecule, and which polymorphisms are not physically linked.

A second sample is prepared as disclosed in Example 18. The tagged library is bulked and sequenced. The same first and second polymorphisms are identified. The polymorphisms are each mapped to multiple templates varying in their first random 8 mer sequence, target sequence start site, target sequence length, target sequence end site and second random 8 mer sequence, indicating that the polymorphisms are independently generated from the sample rather than resulting from a single error in library synthesis which was then differentially amplified.

The first variant of the first polymorphism and the first variant of the second polymorphism are observed to map to some library templates that share a common aliquot tag 5' of their (differing) 5' random 8 mer sequences. The second variant of the first polymorphism and the second variant of the second polymorphism are observed to map to some library templates that share a common aliquot tag, that differs from that of the first variants mentioned immediately previously, 5' of their (differing) 5' first random 8 mer sequence.

It is concluded that the first variant of the first polymorphism and the first variant of the second polymorphism are in phase—that is, they map to a single physical molecule. It is concluded that the second variant of the first polymorphism and the second variant of the second polymorphism are in phase—that is, that they map to a single molecule.

This conclusion is not inconsistent with the presence of some variants also mapping to some library templates that have unique aliquot tags. These sequences that map to unique aliquot tags are inferred to result from events whereby a template molecule is cleaved between the loci of the two polymorphisms.

This conclusion is also not inconsistent with some sequence reads sharing a common aliquot tag despite mapping to disparate regions of the genome. As the aliquots comprise more than a single molecule, different sequence reads will map to different regions of the genome. Provided that two overlapping, out of phase nucleic acid fragments do not end up in a single aliquot, the downstream analysis is unaffected. In the event that two overlapping, out of phase nucleic acid fragments end up in a single aliquot, the presence of both alleles at a locus will indicate that non-physically linked molecules are present in a single sample.

Example 20—Sequence Data Assessment: Repeat Mapping

Traditional sequencing is performed on a genomic sample aliquoted from the sample in Example 18 prior to the dilution step. A sequencing library is generated and sequence information is generated. Sequence data is assembled against a human genome contig scaffold. Sequence corresponding to a repeat unit known to exist at 50 distinct loci in the genome is obtained. A polymorphism is identified in the sequence repeat that may affect transcription of genes at adjacent loci. The polymorphism is embedded in and surrounded by repeat sequence such that the polymorphism cannot be mapped to any of the 50 distinct loci in the genome.

A second sample is prepared as disclosed in Example 18. The tagged library is bulked and sequenced. Sequence is obtained corresponding to the polymorphism discussed above that may affect transcription of genes at adjacent loci. The polymorphism is embedded in and surrounded by repeat sequence. The polymorphism is mapped to multiple templates varying in their first random 8 mer sequence, target sequence start site, target sequence length, target sequence end site and second random 8 mer sequence, indicating that the polymorphisms are independently generated from the sample rather than resulting from a single error in library synthesis which was then differentially amplified.

The polymorphism is observed to map to some library templates that share a common aliquot tag 5' of their (differing) 5' random 8 mer sequences. Sequence corresponding to the repeat region flanking the polymorphism is observed to share a common aliquot tag 5' of their (differing) 5' random 8 mer sequences. Sequences spanning a repeat border, corresponding to both repeat sequence and adjacent sequence that uniquely maps to a single region of the human genome are identified, and it is observed that they share a common aliquot tag 5' of their (differing) 5' random 8 mer sequences.

It is concluded that the polymorphism that may affect transcription of genes at adjacent loci maps to the repeat region immediately adjacent to the locus of the sequence that uniquely maps to a single region of the genome, and not the other 49 repeat regions of highly similar sequence distributed elsewhere throughout the genome.

Example 21—Targeted First Strand Synthesis Oligos

An oligonucleotide population is generated. Each oligo comprises a sequence adapter 5' of a 25 mer specifically synthesized to anneal adjacent to a region of interest in the human genome. Examples of regions of interest include but are not limited to exons, promoter regions, transcription enhances, promoter regions, regions to which genetic diseases map, regions known to be mutant in cancer cell lines or tumor cells, and loci known to be polymorphic in at least one human population. Oligos are synthesized to anneal to either stand adjacent to a region of interest as identified above.

Example 22—Targeted Template Library Generation

A genomic DNA sample is obtained. The sample is contacted with a population of targeted first strand synthesis oligonucleotides as described in Example 20. 4 uL of the population is added to the sample.

Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a relative ratio of 99% deoxy NTP to 1% di-deoxy NTP. 8 uL of the buffer/NTP composition is added to the sample.

The mixture is diluted to 19 uL total volume. The mixture is heated to 98° C. for 3 minutes, during which time the genomic DNA is caused to 'melt' into single-strands unbound by hydrogen boding between complementary bases.

The mixture is then cooled one ice for 2 minutes allow for reverse-complementary base-pairing between the first strand synthesis oligonucleotides and the genomic sample. It is observed that some oligonucleotides demonstrate complete reverse-complementarity between their random 8 mer and the genomic sequence to which each binds. It is also observed that some oligonucleotides bind to genomic regions that are incompletely reverse-complementary to the oligo's random 8 mer. The failure to base pair with complete reverse complementarity is not detrimental to subsequent steps in the random library prep process.

SEQUENASE DNA polymerase (1 uL) having strand displacement activity and able to incorporate biotin-ddNTP is added to the composition. The composition is heated to room temperature and allowed to continue for 30 minutes.

Extension from the 3' OH of the first strand synthesis oligonucleotides is observed, resulting in sequence reverse complementary to the template at the annealing site of each annealed oligo being incorporated at the 3' end of each annealed oligo. Extension continues until a biotin-labeled ddNTP molecule is incorporated, at which point extension terminates. It is further observed that, in light of the 99%/1% ratio of dNTP to biotin-ddNTP complexes, 50% of the first strand oligos on which extension occurs demonstrate an extension of over 50 bases prior to the incorporation of an biotin-ddNTP molecule. The composition is then heated to 98° C. for 5 minutes, during which extension stops.

The sample is subjected to purification and second strand synthesis as indicated in examples 8-11, above.

Example 23—Sequence Data Assessment: Efficiency of Targeted Library Sequencing

Traditional sequencing is performed on a genomic sample aliquoted from the sample in Example 22. A sequencing library is generated and sequence information is generated. Sequence data is assembled against a human genome contig scaffold. The vast majority of the sequence information generated is not of use for diagnosis of an individual from which the sample is obtained.

Sequencing is also performed on the targeted sequencing library as generated in Example 21. It is found that the sequence reads are substantially enriched for sequence of use for diagnosis of an individual from which the sample is obtained, and that substantially fewer reagents and less computing capacity is required to obtain the relevant information.

Example 24—Cancer Targeted Sequencing Library

A targeted sequencing first strand oligonucleotide library is generated having 3' annealing regions that tag each member of a 102 member cancer locus panel (See FIG. 19). The annealing regions are selected to anneal at approximately 20 bp intervals throughout the locus of each member of the panel in each direction.

A genomic nucleic acid sample from a tumor diagnosed as benign and demonstrating no characteristics of metastasis or malignancy is isolated. The tissue comprises cells with substantial polymorphism in genomic sequence of at least one locus listed on the genomic locus panel.

Traditional PCR using a panel of primers spanning each locus is used to assess the mutation status of the tumor tissue. Amplicons are generated, tagged to form a library, and sequenced. Each locus is present in the final product at the expected size for wild type alleles of the each locus.

The cancer panel targeted first strand oligonucleotide library having 3' annealing regions that tag each member of the 102 member cancer locus panel is applied to an aliquot of the genomic nucleic acid sample isolated from the tumor. A sequencing library is generated therefrom and analyzed. It is determined that wild-type copies of each member of the 102 member cancer panel are present in the sample.

In a subset of reads mapping to a cell division repressor, it is determined that the locus is interrupted by a translocation, as indicated by the presence of independent reads, as judged by the presence of distinct random 8 mer sequence and cancer locus sequence starting positions, independently spanning a junction between the locus of interest and translocated sequence.

In a subset of reads mapping to a cell growth repressor, it is determined that the locus has undergone a deletion event, as indicated by the presence of independent reads, as judged by the presence of distinct random 8 mer sequence and cancer locus sequence starting positions, independently spanning a deletion site at which the ends of the locus are present but joined in the absence of intervening sequence.

The cancer panel sequence library data is found to confirm the results of the PCR primer panel assay—namely, that wild type copies of each locus are present in the genomic sample. In addition, the cancer panel sequencing data identifies mutations in two loci that may be indicative of tumor progression. The sample is not homozygous for either of these mutations, and it is expected that each is present in a clear minority of the sample as a whole.

Neither of these mutations are identified by the PCR primer panel assay. The translocation, in all likelihood, is not differentially amplified as the primers which target the locus are too far apart to generate an amplicon, and the wild type amplicon amplifies efficiently enough to sequester the vast majority of primers targeting the locus. The deletion is unlikely to be detected as the effect is to bring the primers close enough that their amplicon is comparable in size to a primer dimer or other amplification artifact, and difficult to purify for sequencing.

The example demonstrates how the cancer panel, and the methods disclosed herein generally, are capable of generating sequence data, easily verified by tag comparison and sequence start site, corresponding to rare events in genomic samples that are easily overlooked in more traditional targeted sequence generation protocols.

Example 25—Hemispecific PCR: Primer Synthesis

To generate a Random Library, a population of first round synthesis oligos is synthesized. The first strand oligonucleotides each comprise an A region positioned 5' of a sequence adapter, itself positioned 5' of a random 8 mer followed by a 3' OH from which template directed extension occurs. The population is synthesized such that all random 8 mers are represented in the first strand oligonucleotide population. However, to increase the efficiency of annealing and, subsequently, first strand synthesis, the population is synthesized so as to include a bias for random 8 mers having a GC percentage of about 40%, such that the overall distribution of 8 mer sequence in the first strand synthesis library reflects that of the human genome as a whole.

A first oligonucleotide primer is designed to be identical to the A adapter region of the first strand oligonucleotide synthesis library above, and to have a 3'OH positioned 5' to the sequence adapter sequence.

A second primer is synthesized having a similar annealing and melting temperature to the first 'A adaptor' region primer, and having specificity such that it anneals with its 3'OH directed so that extension will be directed toward a nucleic acid region of interest.

Example 26—Hemispecific PCR: Data Analysis

A genomic nucleic acid sample is obtained. 50 ng of the sample are aliquoted into a PCR reaction buffer comprising reagents necessary for amplification. A primer pair sufficient for amplification of a region of interest is added. A thermostable heat-activated DNA polymerase is added, and the mixture is subjected to thermocycling (98° C., 30 seconds; followed by six cycles of 95° C., 30 second, 60° C., 20 seconds, 72° C., 30 seconds; a final 72° C. for 2 minutes, and then storage at 4° C.) to amplify the region of interest.

An aliquot of the reaction is analyzed. It is determined that the amount of amplicon generated is insufficient for further analysis.

A second 50 ng of the sample are aliquoted into a PCR reaction buffer comprising reagents necessary for amplification. A primer pair sufficient for amplification of a region of interest is added. A thermostable heat-activated DNA polymerase is added, and the mixture is subjected to thermocycling (98° C., 30 seconds; followed by thirty cycles of 95° C., 30 second, 60° C., 20 seconds, 72° C., 30 seconds; a final 72° C. for 2 minutes, and then storage at 4° C.) to amplify the region of interest.

An aliquot of the reaction is analyzed. It is determined that the amount of amplicon generated is sufficient for further analysis. It is also found that the amplicon comprises point mutations consistent with rare misincorporation events in amplification that, when occurring early in amplification, may represent a large fraction of the final product.

Random first strand oligo synthesis is performed as in Example 7 on 50 ng of the same starting sample. A sample is aliquoted into a PCR reaction buffer comprising reagents necessary for amplification. A first primer identical to a region of the A adapter, and a second primer specific for a region of interest and sufficient for amplification of a region of interest is added. A thermostable heat-activated DNA polymerase is added, and the mixture is subjected to thermocycling (98° C., 30 seconds; followed by six cycles of 95° C., 30 second, 60° C., 20 seconds, 72° C., 30 seconds; a final 72° C. for 2 minutes, and then storage at 4° C.) to amplify the region of interest.

An aliquot of the reaction is analyzed. It is determined that the amount of amplicon generated is sufficient for further analysis. It is also found that, due to the first strand synthesis performed prior to PCR amplification, a large amount of template is generated, such that fewer cycles of amplification are necessary to generate a sufficient amount of amplicon for downstream analyses. Due to the lower number of cycles and the higher amount of starting template, misincorporation errors in the early cycles have little chance of being differentially amplified so as to represent a disproportional amount of the reaction product.

The sequence adapter, random 8 mer sequence, and position of the junction between the random 8 mer and the target sequence of each amplicon is examined. Duplicate amplicons are identified, and duplicate sequence information is disregarded so that each first strand synthesis molecule sequence is assessed in equal proportions. Sequence variant information which is not independently supported by two distinct first strand template sequences is disregarded as representing an error in synthesis. Sequence information corroborated by two independently synthesized first strand molecules is retained as representative of the starting sample sequence.

Example 27—PCR Free Library Generation

A 1 ug DNA sample is obtained and fragmented. Fragments are size selected to have a minimum size of 10 kb. Size-selected fragments are diluted to not more than 100 fragments per aliquot and distributed into separate reaction tubes.

Each aliquoted sample is contacted with a population of first strand synthesis oligonucleotides. The first strand oligonucleotides each comprise a full-length sequence adapter 5' of a random 8'mer followed by a 3' OH from which template directed extension occurs. The random 8 mer is unique to a single oligo, although a small degree of redundancy is easily tolerated by the methods disclosed herein, and even a large degree of redundancy is accommodated. The first strand synthesis oligonucleotides are designed to form hairpin structures to diminish the formation of primer-dimers.

As discussed in Example 6, the random 8 mer population of the first round synthesis oligos represents all possible 8 mers, but the relative abundance of each 8 mer is biased to match the relative abundance of GC vs AT base pairs in the human genome. 4 uL of the population is added to the sample.

Also added to the composition is a polymerase buffer comprising reagents consistent with DNA polymerase activity and a population of nucleotides comprising dATP, dTTP, dCTP and dGTP, and population of biotin tagged ddATP, biotin tagged ddTTP, biotin tagged ddCTP and biotin tagged ddGTP, at a relative ratio of 99% deoxy NTP to 1% di-deoxy NTP. 8 uL of the buffer/NTP composition is added to the sample.

The mixture is diluted to 19 uL total volume. The mixture is heated to 98° C. for 3 minutes, during which time the DNA is caused to 'melt' into single-strands unbound by hydrogen bonding between complementary bases.

The mixture is then cooled one ice for 2 minutes to allow for reverse-complementary base-pairing between the first strand synthesis oligonucleotides and the genomic sample. It is observed that some oligonucleotides demonstrate complete reverse-complementarity between their random 8 mer and the genomic sequence to which each binds. It is also observed that some oligonucleotides bind to regions that are incompletely reverse-complementary to the oligo's random 8 mer. The failure to base pair with complete reverse complementarity is not detrimental to subsequent steps in the random library prep process.

Sequenase DNA polymerase (1 uL) having strand displacement activity and able to incorporate biotin-ddNTP is added to the composition. The composition is heated to room temperature and allowed to continue for 30 minutes.

Extension from the 3' OH of the first strand synthesis oligonucleotides is observed, resulting in sequence reverse complementary to the template at the annealing site of each annealed oligo being incorporated at the 3' end of each annealed oligo. Extension continues until a biotin-labeled ddNTP molecule is incorporated, at which point extension terminates. It is further observed that, in light of the 99%/1% ratio of dNTP to biotin-ddNTP complexes, 50% of the first strand oligos on which extension occurs demonstrate an extension of over 50 bases prior to the incorporation of an biotin-ddNTP molecule.

The composition is then heated to 98° C. for 5 minutes, during which extension stops.

The sample is subjected to purification and second strand synthesis as indicated in examples 8-11, above. The resulting library is then subjected to size selection via gel electrophoresis.

Example 28—Non-Invasive Maternal Testing

A blood sample is obtained from a pregnant woman. This blood sample contains cell-free fetal DNA circulating freely in the maternal bloodstream in fragments of approximately 200 bp in size. The cell-free fetal DNA is separated from the maternal plasma by the addition of formaldehyde to stabilize intact maternal cells, centrifugation, isolation and purification of the supernatant, and size selection via gel electrophoresis. The purified cell-free fetal DNA is then used as the template nucleic acid in the methods described above.

Example 29—Targeted Locus Determination

A first strand synthesis reaction is performed as described herein using a first stand oligo population comprising oligos having a 5' adapter binding region, a barcode region and having a region suitable for annealing to a sample nucleic acid. The oligo population is contacted to the sample under conditions suitable for annealing and extension. The sample-oligo complex is contacted with an extension reaction composition comprising dNTPs, a suitable buffer, a DNA polymerase capable of incorporating biotin-labeled ddNTP, and a small proportion of a biotin-labeled ddNTP.

The composition is contacted with a population of streptavidin beads under binding conditions such that first-strand synthesized beads are bound to the streptavidin beads. The composition is treated so as to melt any double-stranded nucleic acid complexes, and washed such that single-stranded first-strand synthesized molecules remain on the beads.

The bound first-strand synthesized molecules are contacted with a population of second strand oligonucleotides comprising a 25 base sequence that specifically anneals to a locus of interest.

An adapter primer and an excess of second strand oligonucleotides are added to the composition, along with reagents sufficient for thermostable polymerase-mediated nucleic acid amplification. Amplicons are generated and sequenced, thereby determining the sequence of the target locus.

Example 30—Targeted Locus Determination

A first strand synthesis reaction is performed as described herein using a first stand oligo population comprising oligos having a 5' adapter binding region, a barcode region and having a region suitable for nonspecific annealing to a sample nucleic acid. The oligo population is contacted to the sample under conditions suitable for annealing and extension. The sample-oligo complex is contacted with an extension reaction composition comprising dNTPs, a suitable buffer, a DNA polymerase capable of incorporating biotin-labeled ddNTP, and a small proportion of a biotin-labeled ddNTP.

The composition is contacted with a population of streptavidin beads under binding conditions such that first-strand synthesized beads are bound to the streptavidin beads. The composition is treated so as to melt any double-stranded nucleic acid complexes, and washed such that single-stranded first-strand synthesized molecules remain on the beads.

The bound first-strand synthesized molecules are contacted with a population of second strand oligonucleotides comprising a 25 base sequence that specifically anneals to a locus of interest. Second strand synthesis is performed to generate a double stranded molecule.

A 'nested oligonucleotide' population is added to the double stranded template. The 'nested oligonucleotide' comprises a 5' adapter region, a tag sequence, and a 25mer sequence selected to anneal to the same target locus as the second strand oligonucleotide, but downstream (3') of the second strand oligonucleotide binding site.

Extension is performed to generate a second double-stranded molecule having an adapter region at either end, each adapter adjacent to a random tag, flanking a central region of target locus sequence.

The second double-stranded molecule is amplified using oligos complementary to the adapter regions at each end of the molecule, to form amplicons suitable for sequencing.

Using the nested oligonucleotide, the proportion of spuriously generated double stranded molecules—that is, molecules which do not comprise sequence that is adjacent to the 25mer oligo in the target genome or other target sample—are substantially reduced.

Example 31—Targeted Locus Determination

A first strand synthesis reaction is performed as described herein using a first stand oligo population comprising oligos having a 5' adapter binding region, a barcode region and having a 25 base region suitable for specific annealing to a sample nucleic acid target locus. The oligo population is contacted to the sample under conditions suitable for annealing and extension. The sample-oligo complex is contacted with an extension reaction composition comprising dNTPs, a suitable buffer, a DNA polymerase capable of incorporating biotin-labeled ddNTP, and a small proportion of a biotin-labeled ddNTP.

The composition is contacted with a population of streptavidin beads under binding conditions such that first-strand synthesized beads are bound to the streptavidin beads. The composition is treated so as to melt any double-stranded nucleic acid complexes, and washed such that single-stranded first-strand synthesized molecules remain on the beads.

The bound first-strand synthesized molecules are contacted with a population of second strand oligonucleotides comprising oligos having a 5' adapter binding region, a barcode region and having a region suitable for nonspecific annealing to a sample nucleic acid.

An extension reaction is performed using a DNA polymerase having strand-displacement activity.

An adapter primer and an excess of first strand oligonucleotides are added to the composition, along with reagents sufficient for thermostable polymerase-mediated nucleic acid amplification. Amplicons are generated and sequenced, thereby determining the sequence of the target locus.

Example 32—Targeted Locus Determination

A first strand synthesis reaction is performed as described herein using a first stand oligo population comprising oligos having a 5' adapter binding region, a barcode region and having a 25 base region suitable for specific annealing to a sample nucleic acid target locus. The oligo population is contacted to the sample under conditions suitable for annealing and extension. The sample-oligo complex is contacted with an extension reaction composition comprising dNTPs, a suitable buffer, a DNA polymerase capable of incorporating biotin-labeled ddNTP, and a small proportion of a biotin-labeled ddNTP.

The composition is contacted with a population of streptavidin beads under binding conditions such that first-strand synthesized beads are bound to the streptavidin beads. The composition is treated so as to melt any double-stranded nucleic acid complexes, and washed such that single-stranded first-strand synthesized molecules remain on the beads.

The bound first-strand synthesized molecules are contacted with a population of second strand oligonucleotides comprising oligos having a 5' adapter binding region, a barcode region and having a region suitable for nonspecific annealing to a sample nucleic acid.

An extension reaction is performed using a DNA polymerase having strand-displacement activity.

An excess of adapter primer and 'nested first strand oligo' are added to the composition, along with reagents sufficient for thermostable polymerase-mediated nucleic acid amplification. The nested first strand oligo comprises an adapter sequence, a barcode sequence, and a 25-mer sequence that anneals to the same target locus but 3' to the first oligo annealing site.

Amplicons are generated and sequenced, thereby determining the sequence of the target locus.

Example 33—High-Fidelity Cycled First Strand Synthesis

A first strand synthesis reaction is performed as described herein using a random first stand oligo population. The amount of first strand template synthesized in the reaction is found to be insufficient for satisfactory downstream analysis.

A first strand synthesis reaction is performed as described herein using a random first stand oligo population. Prior to binding to streptavidin, the sample is heated to denature he sample form the synthesized first strand and a second round of first strand synthesis is performed. The process is repeated to generate multiple rounds of first strand synthesis template. The first strand template generated through these multiple cycles is found to comprise molecules generated from the original sample template, as well as molecules generated from templates arising from previous cycles of first strand template. The molecules not generated from original sample template are found to incorporate artefactual sequence information such as a higher frequency of base misincorporation and a nonzero frequency of artefactual translocation and transposition events.

A first strand synthesis reaction is performed as described herein using a random first stand oligo population and a dNTP pool where dATP is replaced by 2,6-diamino-dATP and dTTP is replaced by 2-thiothymidine. 2,6-diaminopurine and 2-thiothymidine are incorporated into first strands as they are synthesized.

Prior to binding to streptavidin, the sample is heated to denature the sample form the synthesized first strand and a second round of first strand synthesis is performed. Oligos anneal to both the sample template and to synthesized first strand molecules, but the presence of the modified bases blocks synthesis of novel molecules directed by the first strand molecules synthesized previously.

The amount of first strand template synthesized in the reaction is found to be sufficient for satisfactory downstream analysis. The first strand template generated through these multiple cycles is found to comprise molecules generated from the original sample template, but not molecules generated from templates arising from previous cycles of first strand template. The first strand molecules generated through this cycled process are found not to incorporate artefactual sequence information such as a higher frequency of base misincorporation and are found not to incorporate artefactual translocation and transposition events.

Example 34—Process Workflow

A single human genome nucleic acid sample is distributed into 24 input wells. These inputs each get distributed across 48 nanoliter reactions. 48 distinct labelled primers are included for the first strand synthesis "A" reaction. After the A rxn, the material is harvested and combined back into the original 24 input wells. The 24 wells worth of material for one sample is used to finish the second strand "B" rxn in 24 individual tubes. 24 barcoded PCR primer sets are used to amplify and incorporate the full length adapters. The result of the process workflow yields 24×48=1,152 label combinations. 48 labels originate from the A rxn, and each is in combination with the additional 24 labels from the PCR reaction. A result of this workflow is that the equivalent of 24 preps are performed per sample.

Example 35—Human Genome Sequencing Reaction

A sample comprising human genomic nucleic acids was used to prepare a nucleic acid library, and the library was sequenced. The reaction parameters were as follows:

1. Reaction A
a.) Prepare the reaction by combining the following reagents (preferably in an Eppendorf DNA LoBind microcentrifuge tube):
   x µL DNA (1-2 ng)
   4 µL 25 µM Primer A
   2 µL 10×Thermo Sequenase Buffer
   4 µL dNTP/ddNTP mix
   Nuclease-Free Water for a final volume of 19 µL
   If working with multiple samples, it is recommended to prepare a master mix with an additional 10% to compensate for loss during pipetting.
b.) Incubate the reaction at 95° C. for 3 minutes to denature the DNA. Place the tube on ice for at least 2 minutes.
c.) Add 1 µL Thermo Sequenase to the reaction. Mix gently.
d.) Transfer the reaction to a thermal cycler. Proceed with the following program on the instrument:
   1.) 16° C. for 10 minutes
   2.) Slow ramp (0.1° C./sec) to 60° C.
   3.) 60° C. for 10 minutes
   4.) 95° C. for 30 seconds
   5.) Return to step 1; perform this step 9 times (for a total of 10 cycles (~5 hours))
   6.) Hold at 4° C.
   Note: For the long read application, all A reaction components, except primer, should be combined and loaded onto a relevant partitioning device. After the reaction is partitioned and combined with barcoded primers, it should be transferred to a thermal cycler, heat denatured at 95° C. for 2 minutes, and subsequently thermocycled according to the program detailed above.
   After the A reaction, samples are stored temporarily at 4° C. or on ice, or frozen at −20° C. for long term storage. Shortly before continuing with Step 2, heat the samples at 98° C. for 3 minutes, then transfer them to ice.
2. DNA Capture with Magnetic Beads
a.) Shake the Capture Bead tube thoroughly to resuspend the beads and transfer 40 µL of the beads to a new 0.5 mL Eppendorf DNA LoBind tube. Place the tube on a magnetic stand and wait for solution to clear (0.5-1 minute). Carefully remove the supernatant with a pipette and discard it.
b.) Remove the tube from the magnetic stand and add 200 µL of HS Buffer to the beads. Pipette the sample up and down to mix the components, then return the tube to the magnetic stand. Wait for the solution to clear. Carefully remove and discard the supernatant.
c.) Remove the tube from the magnetic stand and resuspend the beads in 40 µL of HS Buffer. The tube is left on the laboratory bench at room temperature until Step 1 is complete.
d.) Add the product of the A reaction (from Step 1) to the Capture Beads (from the previous step) and incubate the sample at room temperature for 20 minutes. Mix the sample by pipetting up and down after 10 minutes.
e.) Place the tube on the magnetic stand and wait for the solution to clear. Carefully remove and discard the supernatant.
f) Remove the tube from the magnetic stand and resuspend the beads in 200 µL of Bead Wash Buffer. Return the tube to the magnetic stand, allow the solution to clear and discard the supernatant.

g.) Repeat the wash step (previous step) two additional times. Carefully remove any remaining liquid after the final wash.
3. Reaction B
a.) Add the reagents listed below to the tube containing the Capture Beads (from Step 2 g): 8 μL 5× Sequenase buffer
3 μL 2 mM dNTPs
4 μL 25 μM Primer B
24 μL Nuclease-Free Water
1 μL Sequenase (1:1 ratio of Sequenase & Inorganic Pyrophosphatase)
Total=40 μL
If working with multiple samples, it is recommended to prepare a master mix with an additional 10% to compensate for loss during pipetting.
b.) Incubate the reaction for 20 minutes at 24° C. (preferably in a thermal cycler or heating block).
c.) Place the tube on the magnetic stand. Allow the solution to clear and discard the supernatant.
d.) Remove the tube from the magnetic stand and resuspend the beads in 200 μL of Bead Wash Buffer. Return the tube to the magnetic stand, allow the solution to clear and discard the supernatant.
e.) Repeat the wash step (previous step) two additional times. Carefully remove any remaining liquid after the final wash.
4. PCR
a.) Resuspend the beads from Step 3e in 42 μL of Nuclease-Free Water. Transfer the beads to a thin-walled PCR tube. Add the following components:
4 μL 25 μM PCR Universal Primer I
4 μL 25 μM PCR Primer II (barcodes 1-12)
50 μL 2×KAPA HiFi PCR Amplification Mix
Total=100 μl
Input the following parameters into a thermal cycler and perform a PCR:

1 cycle
98° C., 2 minutes
15 cycles
98° C., 20 seconds
60° C., 30 seconds
72° C., 30 seconds
1 cycle
72° C., 5 minutes
4° C., hold
5. AmpureXP Bead-Based Clean-Up
a.) Place the PCR tube on a magnetic stand, wait for solution to clear and transfer the supernatant to a new 0.5 mL Eppendorf DNA LoBind tube. Discard the PCR tube containing the Capture Beads.
b.) Add 100 μL of AmpureXP Beads to the supernatant, pipette to mix and incubate the tube at room temperature for 10 minutes.
c.) Place the tube on the magnetic stand, allow the solution to clear and discard the supernatant.
d.) Add 200 μL of 80% ethanol to the tube. Wait 30 seconds, then remove and discard the ethanol. It is unnecessary to remove the tube from the magnetic stand during this step.
e.) Repeat the wash step with another 200 μL of 80% ethanol.
f.) Open the cap of the tube and allow the beads to air dry for 10-15 minutes on the laboratory bench.
g.) Add 20-30 μL of 10 mM Tris-HCl (pH 7.8) to the beads. Mix by pipetting up and down. Allow the tube to sit at room temperature for 2 minutes.
h.) Place the tube on the magnetic stand, allow the solution to clear and transfer the supernatant containing the eluted DNA to a new Eppendorf DNA LoBind tube.

The library was generated according to the above-mentioned protocol, and quantitated on an Agilent Bioanalyzer using a high sensitivity DNA chip prior to sequencing.
Sequencing statistics are presented in Table 7

TABLE 7

| | Library Sequencing results | | |
|---|---|---|---|
| CATEGORY | FIRST OF PAIR | SECOND OF PAIR | PAIR |
| TOTAL READS | 178043095 | 178043095 | 356086190 |
| PF READS | 178043095 | 178043095 | 356086190 |
| PCT PF READS | 1 | 1 | 1 |
| PF NOISE READS | 0 | 0 | 0 |
| PF READS ALIGNED | 176721690 | 174608610 | 351330300 |
| PCT PF READS ALIGNED | 0.992578 | 0.98071 | 0.986644 |
| PF ALIGNED BASES | 23344777210 | 22700226388 | 46045003598 |
| PF HQ ALIGNED READS | 155230971 | 149713452 | 304944423 |
| PF HQ ALIGNED BASES | 21418756658 | 20460330551 | 41879087209 |
| PF HQ ALIGNED Q20 BASES | 20164741562 | 18421001150 | 38585742712 |
| PF HQ MEDIAN MISMATCHES | 0 | 0 | 0 |
| PF MISMATCH RATE | 0.008971 | 0.013039 | 0.010977 |
| PF HQ ERROR RATE | 0.006341 | 0.01036 | 0.008305 |
| PF INDEL RATE | 0.00036 | 0.000385 | 0.000372 |
| MEAN READ LENGTH | 142.493392 | 142.320359 | 142.406876 |
| READS ALIGNED IN PAIRS | 174025581 | 174025581 | 348051162 |
| PCT READS ALIGNED IN PAIRS | 0.984744 | 0.996661 | 0.990667 |
| BAD CYCLES | 0 | 0 | 0 |
| STRAND BALANCE | 0.515658 | 0.506214 | 0.510965 |
| PCT CHIMERAS | 0.002138 | 0.002138 | 0.002138 |
| PCT ADAPTER | 0 | 0.000001 | 0.000001 |
| SAMPLE | | | |
| LIBRARY | | | |
| READ GROUP | | | |

Figure 24:
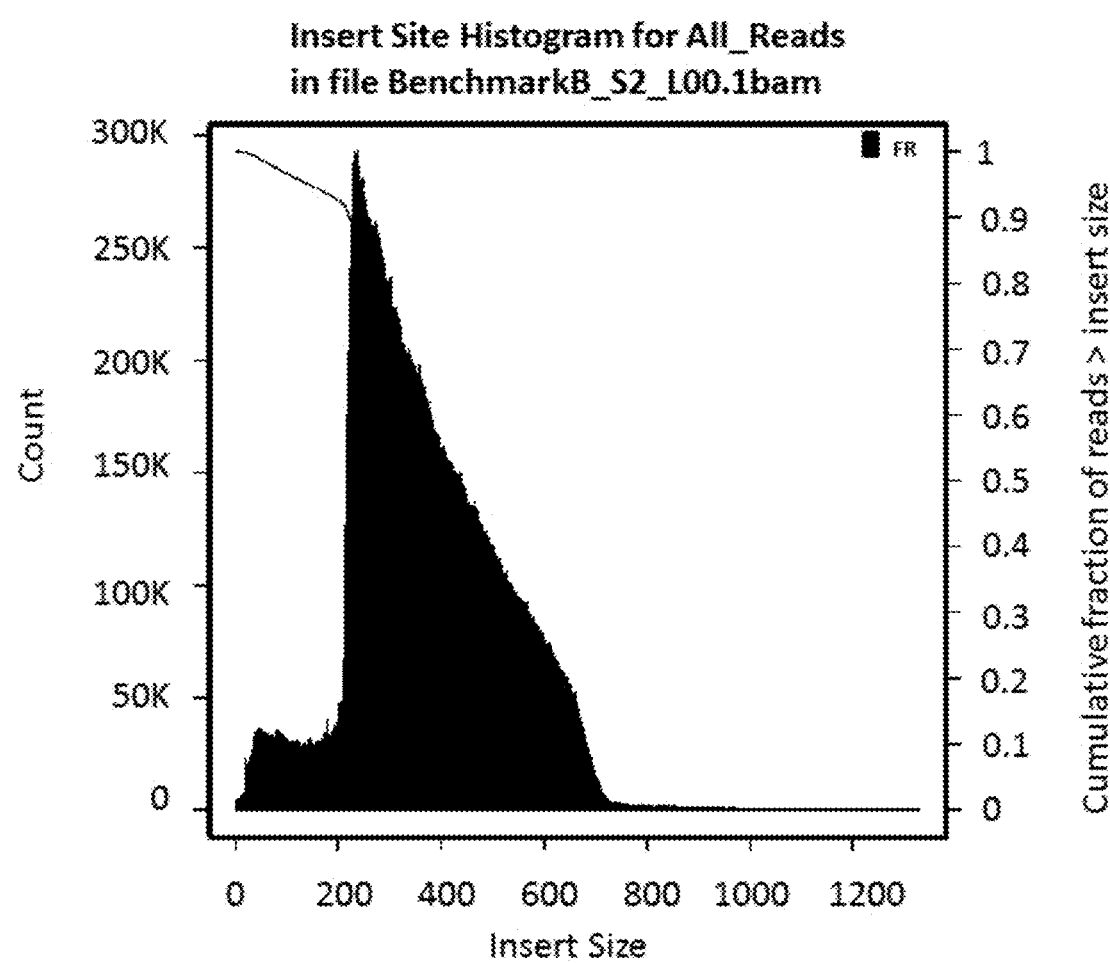
FIG. 24 is a distribution of insert sizes for a library generated against a human genome sample.

One observes the following from these results. Over 98% of reads where aligned in the genome assembly. The mismatch rate and error rate both fell below 1%, and the indel rate fell below 0.1%. The mean read length was about 142 bases. The peak insert size was about 280 bases, tailing off to about zero at an insert size between 700 and 800. The median insert size was 350, and the mean at 369 bases. A distribution of insert sizes is given at FIG. 24.

The library was sequences and the results analyzed.

Figure 25:
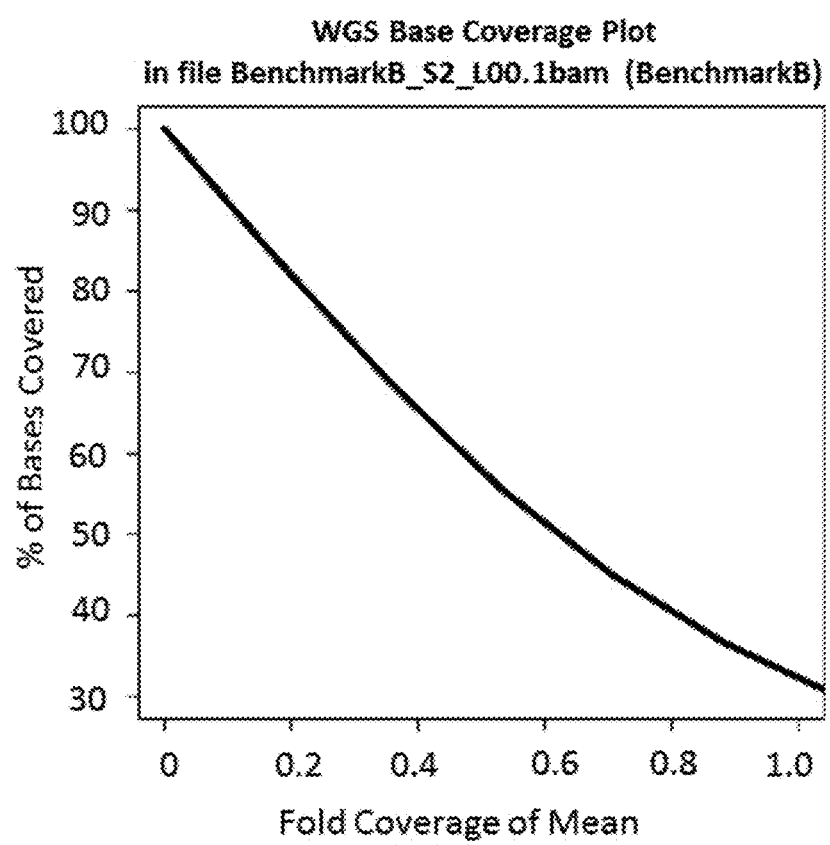
FIG. 25 is a plot of base coverage for a library generated against a human genome sample.

A plot of Base Coverage is given in FIG. 25.

Example 36—Human Genome Sequencing Reaction

A sample comprising human genomic nucleic acids was used to prepare a nucleic acid library, and the library was sequenced. The reaction parameters were as given in Example 35, above.

Sequencing statistics are presented in Table 9

TABLE 9

Library Sequencing results

| CATEGORY | FIRST OF PAIR | SECOND OF PAIR | PAIR |
| --- | --- | --- | --- |
| TOTAL READS | 209093984 | 209093984 | 418187968 |
| PF READS | 209093984 | 209093984 | 418187968 |
| PCT PF READS | 1 | 1 | 1 |
| PF NOISE READS | 0 | 0 | 0 |
| PF READS ALIGNED | 207672223 | 204819978 | 412492201 |
| PCT PF READS ALIGNED | 0.9932 | 0.979559 | 0.98638 |
| PF ALIGNED BASES | 27374026436 | 26547357956 | 53921384392 |
| PF HQ ALIGNED READS | 180764619 | 173920422 | 354685041 |
| PF HQ ALIGNED BASES | 24878930962 | 23704375472 | 48583306434 |
| PF HQ ALIGNED Q20 BASES | 23367560440 | 21264539012 | 44632099452 |
| PF HQ MEDIAN MISMATCHES | 0 | 0 | 0 |
| PF MISMATCH RATE | 0.009878 | 0.014066 | 0.01194 |
| PF HQ ERROR RATE | 0.006651 | 0.01087 | 0.00871 |
| PF INDEL RATE | 0.000369 | 0.000389 | 0.000379 |
| MEAN READ LENGTH | 142.480652 | 142.293384 | 142.387018 |
| READS ALIGNED IN PAIRS | 204105734 | 204105734 | 408211468 |
| PCT READS ALIGNED IN PAIRS | 0.982826 | 0.996513 | 0.989622 |
| BAD CYCLES | 0 | 0 | 0 |
| STRAND BALANCE | 0.506455 | 0.509402 | 0.507918 |
| PCT CHIMERAS | 0.006053 | 0.006053 | 0.006053 |
| PCT ADAPTER | 0 | 0.000001 | 0.000001 |
| SAMPLE | | | |
| LIBRARY | | | |
| READ GROUP | | | |

The sequencing statistics are given in Table 8.

TABLE 8

| | |
| --- | --- |
| GENOME TERRITORY | 2864785223 |
| MEAN COVERAGE | 5.657007 |
| SD COVERAGE | 9.855615 |
| MEDIAN COVERAGE | 3 |
| MAD COVERAGE | 2 |
| MEAN COVERAGE NON ZERO | 6.736822 |
| SD COVERAGE NON ZERO | 10.411508 |
| MEDIAN COVERAGE NON ZERO | 4 |
| PCT EXC MAPQ | 0.097465 |
| PCT EXC DUPE | 0.483582 |
| PCT EXC UNPAIRED | 0.004779 |
| PCT EXC BASEQ | 0.029157 |
| PCT EXC COVERLAP | 0.015752 |
| PCT EXC CAPPED | 0.020484 |
| PCT EXC TOTAL | 0.651219 |
| PCT 1X | 0.839714 |
| PCT 5X | 0.366349 |
| PCT 10X | 0.155123 |
| PCT 15X | 0.082564 |
| PCT 20X | 0.050174 |
| PCT 25X | 0.033064 |
| PCT 30X | 0.023025 |
| PCT 40X | 0.012487 |
| PCT 50X | 0.007535 |
| PCT 60X | 0.004871 |
| PCT 70X | 0.003327 |
| PCT 80X | 0.002376 |
| PCT 90X | 0.001763 |
| PCT 100X | 0.001346 |

Figure 26:
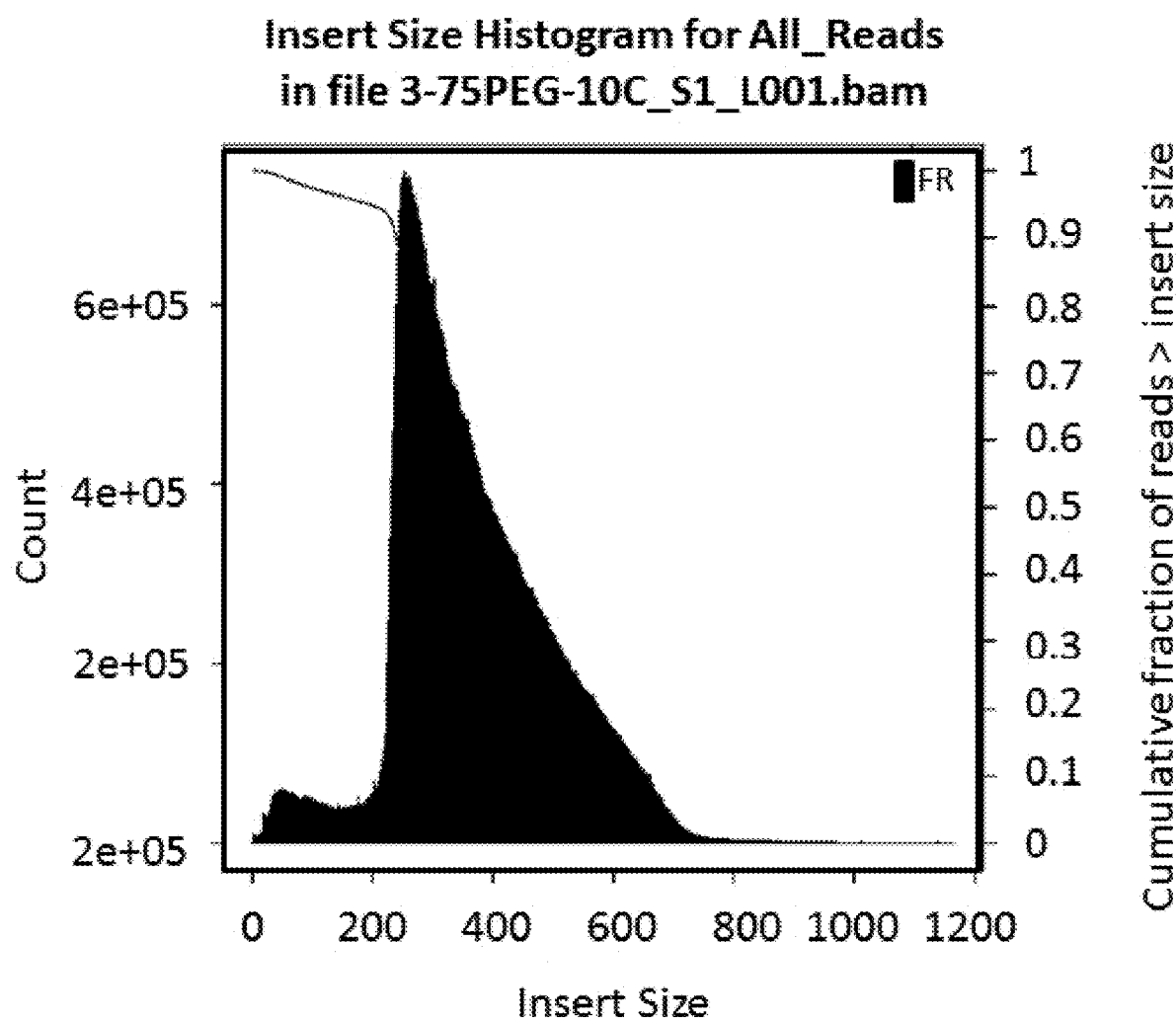
FIG. 26 is a distribution of insert sizes for a second library generated against a human genome sample.

One observes the following from these results. Over 99% of reads where aligned in the genome assembly. The mismatch rate and error rate both fell below 1%, and the indel rate fell below 0.01%. The mean read length was about 142 bases. The peak insert size was about 250 bases, tailing off to about zero at an insert size between 700 and 800. The median insert size was 345, and the mean at 365 bases. A distribution of insert sizes is given at FIG. 26.

The library was sequences and the results analyzed.

Figure 27:
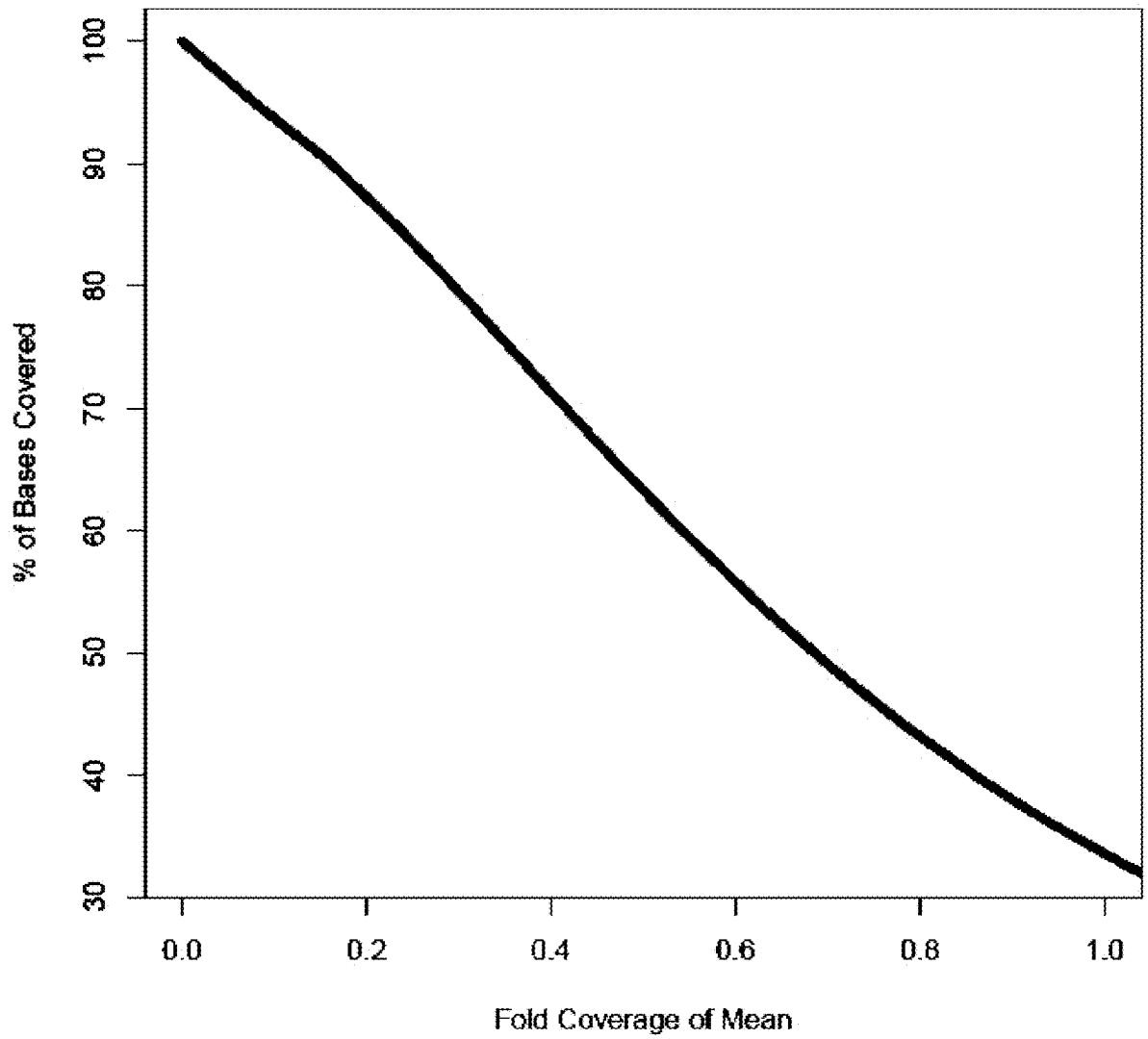
FIG. 27 is a plot of base coverage for a second library generated against a human genome sample.

A plot of Base Coverage is given in FIG. 27.

The sequencing statistics are given in Table 10.

TABLE 10

| | |
| --- | --- |
| GENOME TERRITORY | 2864785223 |
| MEAN COVERAGE | 12.733176 |
| SD COVERAGE | 16.096758 |
| MEDIAN COVERAGE | 8 |
| MAD COVERAGE | 5 |
| MEAN COVERAGE NON ZERO | 13.409253 |
| SD COVERAGE NON ZERO | 16.241838 |
| MEDIAN COVERAGE NON ZERO | 9 |
| PCT EXC MAPQ | 0.107178 |
| PCT EXC DUPE | 0.101811 |
| PCT EXC UNPAIRED | 0.006743 |
| PCT EXC BASEQ | 0.06195 |
| PCT EXC COVERLAP | 0.02208 |
| PCT EXC CAPPED | 0.032156 |
| PCT EXC TOTAL | 0.331918 |
| PCT 1X | 0.949581 |
| PCT 5X | 0.718924 |
| PCT 10X | 0.43937 |

TABLE 10-continued

| | |
|---|---|
| PCT 15X | 0.270991 |
| PCT 20X | 0.176921 |
| PCT 25X | 0.122192 |
| PCT 30X | 0.088253 |
| PCT 40X | 0.050574 |
| PCT 50X | 0.031369 |
| PCT 60X | 0.020419 |
| PCT 70X | 0.13785 |
| PCT 80X | 0.009552 |
| PCT 90X | 0.006777 |
| PCT 100X | 0.004909 |

In summary, using only 400M reads or about 60 Gbp of sequence (an average of 13× coverage) 95% coverage of the human reference sequence was obtained.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

population comprises at least one mismatch between said random primer sequence and said sample nucleic acid sequence, wherein at least a first molecule of said population comprises a first independent target sequence comprising a first subset of said sample nucleic acid sequence, and wherein at least a second molecule of said population comprises a second independent target sequence that comprises a second subset of said sample nucleic acid sequence.

2. The composition of claim 1, wherein said first sequencer specific adapter of each first strand of said population is identical.

3. The composition of claim 1, wherein said molecular tag sequence of each molecule of said population comprises at least 6 nucleotide bases.

4. The composition of claim 1, wherein a first member of said population and a second member of said population comprise non-identical molecular tag sequences.

5. The composition of claim 1, wherein each first strand comprises a 3'-deoxynucleotide base at its 3' end.

6. The composition of claim 1, wherein each first strand comprises a molecular ligand at its 5' end.

7. The composition of claim 1, wherein each first strand comprises a molecular ligand attached at a non-terminal position.

8. The composition of claim 1, wherein each first strand comprises a molecular ligand at its 3' end.

---

---

I claim:

1. A composition comprising a population of nucleic acid molecules, wherein each molecule of said population independently comprises:
   a first strand comprising
      a first sequencer specific adapter sequence,
      a molecular tag sequence comprising a barcode, and
      an independent target sequence,
      wherein each independent target sequence comprises a random primer sequence and a subset of a sample nucleic acid sequence, wherein at least one of said 9. The composition of claim 8, wherein said molecular ligand is biotin.

10. The composition of claim 1, wherein each molecule of said population comprises a second strand comprising:
   a second sequencer specific adapter sequence, and
   a second molecular tag sequence comprising a barcode.

11. The composition of claim 10, wherein said second strand of at least one molecule of said population is annealed to a first strand via at least partial base pairing of a second molecular tag sequence of said second strand to the independent target sequence of said first strand.

12. The composition of claim 1, wherein at least one molecule of said population is bound to a molecular ligand binder.

13. The composition of claim 1, wherein said composition comprises unincorporated nucleic acid triphosphates.

14. The composition of claim 1, wherein said composition comprises molecular ligand binder wash buffer.

15. The composition of claim 1, wherein said composition comprises polymerase extension buffer.

16. The composition of claim 1, wherein said composition comprises nucleic acid polymerase.

17. The composition of claim 16, wherein said composition comprises nucleic acid polymerase possessing nucleic acid helicase activity.

18. The composition of claim 16, wherein said composition comprises nucleic acid polymerase possessing nucleic acid strand displacement activity.

19. The composition of claim 16, wherein said composition comprises nucleic acid comprising SEQ ID NO: 1 and SEQ ID NO: 2.

20. The composition of claim 1, wherein the composition is contained in a single tube.

\* \* \* \* \*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aatgatacgg cgaccaccga                                               20

<210> SEQ ID NO 2
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
caagcagaag acggcatacg agat                                          24
```